US011513123B2

(12) United States Patent
Ivancic et al.

(10) Patent No.: US 11,513,123 B2
(45) Date of Patent: Nov. 29, 2022

(54) METHODS FOR DETECTION AND TREATMENT OF COLORECTAL CANCER

(71) Applicant: Wisconsin Alumni Research Foundation, Madison, WI (US)

(72) Inventors: Melanie Mae Ivancic, Madison, WI (US); Michael Richard Sussman, Cross Plaines, WI (US); William Franklin Dove, Madison, WI (US); Amy Ann Irving, Madison, WI (US); Jennifer Kathleen Pleiman, Madison, WI (US); Edward Lee Huttlin, Somerville, MA (US); Xiaodi Chen, Madison, WI (US); Adrian Daniel Hegeman, Saint Paul, MN (US); Mark Reichelderfer, Madison, WI (US); Gregory D. Kennedy, Madison, WI (US); Perry J. Pickhardt, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 422 days.

(21) Appl. No.: 15/532,437

(22) PCT Filed: Dec. 10, 2015

(86) PCT No.: PCT/US2015/065049
§ 371 (c)(1),
(2) Date: Jun. 1, 2017

(87) PCT Pub. No.: WO2016/094692
PCT Pub. Date: Jun. 16, 2016

(65) Prior Publication Data
US 2017/0269089 A1    Sep. 21, 2017

Related U.S. Application Data

(60) Provisional application No. 62/090,800, filed on Dec. 11, 2014.

(51) Int. Cl.
| | |
|---|---|
| *A61K 31/00* | (2006.01) |
| *G01N 33/574* | (2006.01) |
| *G01N 30/02* | (2006.01) |
| *G01N 30/72* | (2006.01) |
| *G01N 33/50* | (2006.01) |

(52) U.S. Cl.
CPC ....... *G01N 33/57419* (2013.01); *G01N 30/02* (2013.01); *G01N 30/72* (2013.01); *G01N 33/5005* (2013.01); *G01N 2030/027* (2013.01); *G01N 2333/00* (2013.01); *G01N 2800/60* (2013.01)

(58) Field of Classification Search
CPC .. G01N 33/57419; G01N 30/02; G01N 30/72; G01N 33/5005; G01N 2030/027; G01N 2333/00; G01N 2800/60
See application file for complete search history.

(56) References Cited

U.S. PATENT DOCUMENTS

2012/0295815 A1\* 11/2012 Lindahl ............... C12Q 1/6886
                                                                506/9

FOREIGN PATENT DOCUMENTS

| WO | WO2010042228 | | 4/2010 | |
|---|---|---|---|---|
| WO | WO2011087865 | \* | 7/2011 | |
| WO | WO2012018613 | | 2/2012 | |
| WO | WO2012083338 | | 6/2012 | |
| WO | WO2012174282 | | 12/2012 | |
| WO | WO2013152989 | | 10/2013 | |
| WO | WO2014085826 | | 6/2014 | |
| WO | WO-2014085826 A2 \* | | 6/2014 | ....... G01N 33/57419 |
| WO | WO2014183777 | | 11/2014 | |
| WO | WO-2014183777 A1 \* | | 11/2014 | ......... G01N 33/6893 |

OTHER PUBLICATIONS

Ivancic et al (Cancer Prov Res 7:1160-69, published online Sep. 2014, item #11, IDS filed on Jul. 5, 2017 (Year: 2014).\*
Orntoft et al (Mole Cell Proteiomics 1: 37-45, 2002 (Year: 2002).\*
Lange et al. (Mole Sys Biol 4:222, 2008, #45 in IDS filed on Jul. 5, 2017 (Year: 2008).\*
Amos-Landgraf, J.M., et al, Proc. Natl. Acad. Sci, 104(10), 4036-41 (2007).
Brazma, A., et al., Nat. Genet, 29(4), 365-71 (2001).
Edgar, R., et al, Nucleic Acids Res, 30(1), 207-10 (2002).
Vogelstein, B., et al., Science, 339(6127), 1546-58 (2013).
Altschul, S.F., et al., J. Mol. Biol, 215(3) 403-10 (1990).
Yang, F., et al., Expert Rev Proteomics, 9(2) 129-34 (2012).
Deutsch, et al., EMBO Rep, 9(5) 429-34 (2008).
Tuck, et al., J. Proteome Res, 8(1) 113-7 (2009).
Serang, O., et al., J. Proteome Res., 12(10) 4556-65 (2013).
Grund, et al., Curr Opin HIV AIDS, 5(6) 473-9 (2010).
Ivancic, M., et al., Cancer Prev Res, 55, 7(11) 1160-9 (2014).
Wexner, S.D., et al., Gastrointest Endosc, 63(7) 894-909 (2006).
Hsieh, S.Y., et al., Proteomics, 6(10) 3189-98 (2006).
MacLean, B., et al., Bioinformatics, 26(7) 966-8 (2010).
Abbatiello, S.E., et al., Clin Chem, 56(2) 291-305 (2010).
International Search Report and Written Opinion for PCT/US2015/065049 dated May 17, 2016, pp. 1-20.
Jemal, et al., CA Cancer J. Clin, 61(2), 69-90 (2011).
Hopchik, Gastroenterol Nurs, 36(4), 289-90 (2013).
Kriza, et al., Eur J. Radiol., 82(11), e629-36 (2013).
Leng, et al,. J. Gerontol A. Biol Sci Med Sci, 63(8), 879-84 (2008).
Burt, et al., J. Natl Compr Canc Netw, 11(12), 1538-75 (2013).

(Continued)

*Primary Examiner* — Lei Yao
(74) *Attorney, Agent, or Firm* — McDonnell Boehnen Hulbert & Berghoff LLP

(57) ABSTRACT

This invention provides methods, reagents, and diagnostic and prognostic markers useful for minimally invasive identification, diagnosis, and therapeutic intervention in individuals with colorectal cancers, or individuals who may be susceptible to developing colorectal cancers.

12 Claims, 24 Drawing Sheets
Specification includes a Sequence Listing.

(56) References Cited

OTHER PUBLICATIONS

Gunderson, L.L, et al. J. Clin Oncol, 28(2), 264-71 (2010).
Greene, F.L., Bull Am Coll Surg, 87(7), 13-15 (2002).
Dukes, C.E., Journal of Pathological Bacteriology, 35:323 (1932).
Astler, V.B., Ann Surg, 139:846 (1954).
Chen, L., et al., J. Biol Chem, 269(45), 28282-7 (1994).
Misra, S., et al. Connect Tissue Res, 49(3), 219-24 (2008).
Chong, P.K., et al., J. Proteome Res, 9(7) 3671-9 (2010).
Lieto, E., et al., Ann Surg Oncol, 15(1), 69-79 (2008).
Foell, D., et al., Gut, 58(6), 859-68 (2009).
Ward, et al., Br J. Cancer, 94(12), 1898-905 (2006).
Hsu, S.J., et al., Genome, 47(5), 931-46 (2004).
Shirai, R., et al, Biochem Biophys Res Commun, 382(4), 776-9 (2009).
Hung, K.E., et al., Cancer Prev Res (Phila), 2(3), 224-33 (2009).
Ladd, J., et al., Cancer Prev Res (Phila), 5(4), 655-64 (2012).
Ivancic, M.M., et al., J. Proteome Res, 12(9), 4152-66 (2013).
Serada, S., et al., Inflamm Bowel Dis., 18(11) 2169-79 (2012).
Wang, X., et al., Nature, 499(7458), 306-11 (2013).
Hanahan, D., et al., Cell, 144(5), 646-74 (2011).
Surinova, S., et al., EMBO Mol Med., 7, 1153-1165 (2015).
Surinova, S., et al., EMBO Mol Med., 7, 1166-1178 (2015).
Real, F., et al., Int J. Cancer, 51(2), 173-81 (1992).
Young, G.P., et al., J. Gastroenterol Hepatol, 7(4), 347-54 (1992).
Sim, L., J. Mol. Biol., 375(3), 782-92 (2008).
Sengupta, P., et al,. J. Biol. Chem, 280(22), 21004-14 (2005).
Medici, D., et al., Matrix Biol, 29(3), 161-5 (2010).
Davie, E.W., et al., Biochemistry, 30(43) 10363-70 (1991).
Falanga, A., et al., J. Thromb Haemost, 11(2), 223-33 (2013).
Alcalay, A., et al., J. Clin Oncol, 24(7), 1112-8 (2006).
Paspatis, G.A., et al. Pathophysiol Haemost Thromb, 32(1), 2-7 (2002).
Vossen, C.Y., et al., J Clin Oncol 29(13), 1722-7 (2011).
Felding-Habermann, B., et al., Curr Opin Cell Biol, 5(5), 864-8 (1993).
Milis, L., et al., Clin Exp Immunol., 92(1), 114-9 (1993).
Caruso, M., et al., Virchows Arch, 454(3), 291-302 (2009).
Cavallo-Medved, D., et al., Neoplasia, 5(6), 507-19 (2003).
Shibata, M., et al., Eur. J. Biochem, 270(6), 1189-98 (2003).
Mason, R.W., Arch Biochem Biophys, 273(2), 367-74 (1989).
Yocum, A.K., et al., Brief Funci Genomic Proteomic, 8(2), 145-57 (2009).
Gerber, S.A., et al., Proc Natl. Acad Sci, 100(12), 6940-5 (2003).
Kaiser, S.E., et al. Nat Methods, 8(8), 691-6 (2011).
Lange,V., et al., Mol. Syst. Biol, 4, pp. 222 (2008).
Picotti, P., et al., Nature, 494, 266-70 (2013).
Elias, J.E., et al., Nat Methods 2(9), 667-75 (2005).
Kirkpatrick, D.S., et al., Methods, 35(3), 265-73 (2005).
Banack, S.A., et al., Toxicon, 56(6), 868-79 (2010).
Mantovani, A., et al., Nature, 454(7203), 436-44 (2008).

\* cited by examiner

Tier 1—
Criteria that must be met

Peptide uniqueness within species
(BLAST searching http://blast.ncbi.nlm.nih.gov/Blast.cgi)

Relative hydrophobicity
Sequence specific retention time (SSRCalc)

Peptide length
Peptides must be longer than 6 amino acids and less than 21 amino acids

Known posttranslational modifications
(glycosylation, phosphorylation, oxidation, etc.)

Tier 2—
Improve chances of observing the target peptide with a priori knowledge of a peptide's mass spectrometry performance

Presence in of peptide in untargeted experiments
Untargeted Discovery data (e.g. LTQ-Orbitrap results)

Presence of peptide in MS results from other laboratories (especially blood)
PeptideAtlas mass spectrometry data repository (Has builds for Mouse, Yeast, and Human)

Missed cleavage analysis
Missed cleavages identified by untargeted mass spectrometry

Assessment of good SRM peptides
SRM Atlas (Mouse, Yeast and Human)

Tier 3—
Cross species analysis for use of peptides in multiple translational targeted studies

Cross-species similarity
BLAST searching—Sequence alignment analysis of multiple species (e.g. try to find cross-species similarity between mice, rats, and humans)

Fig. 2

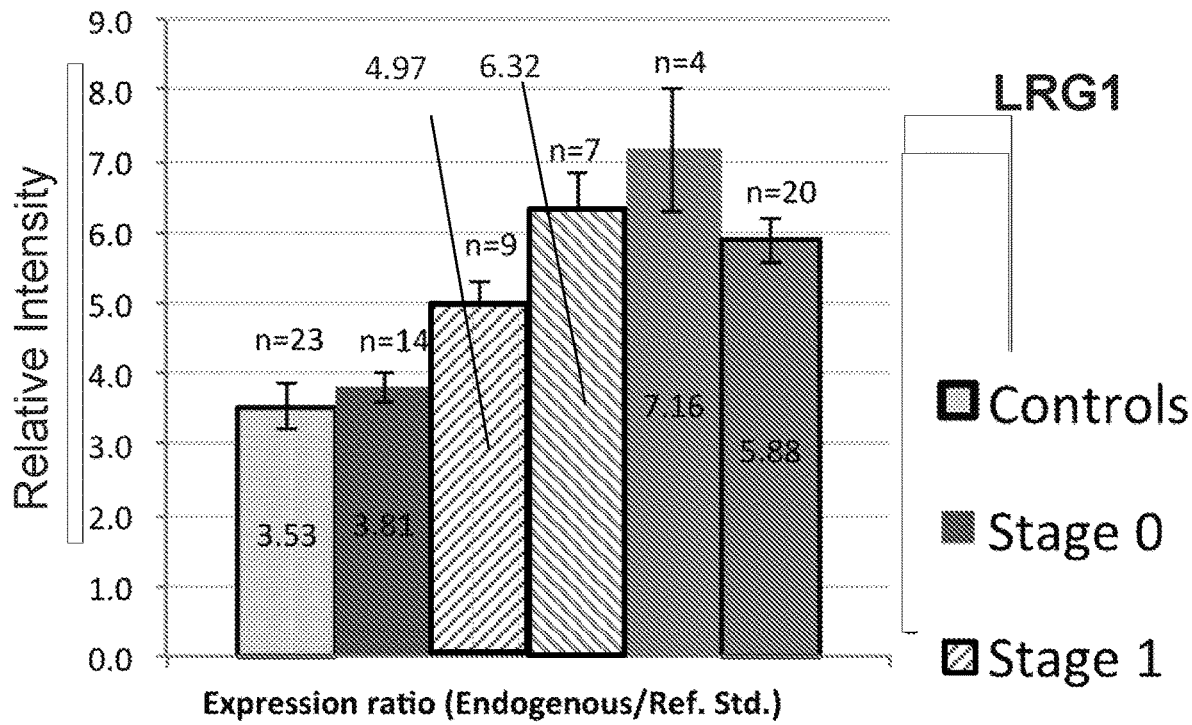
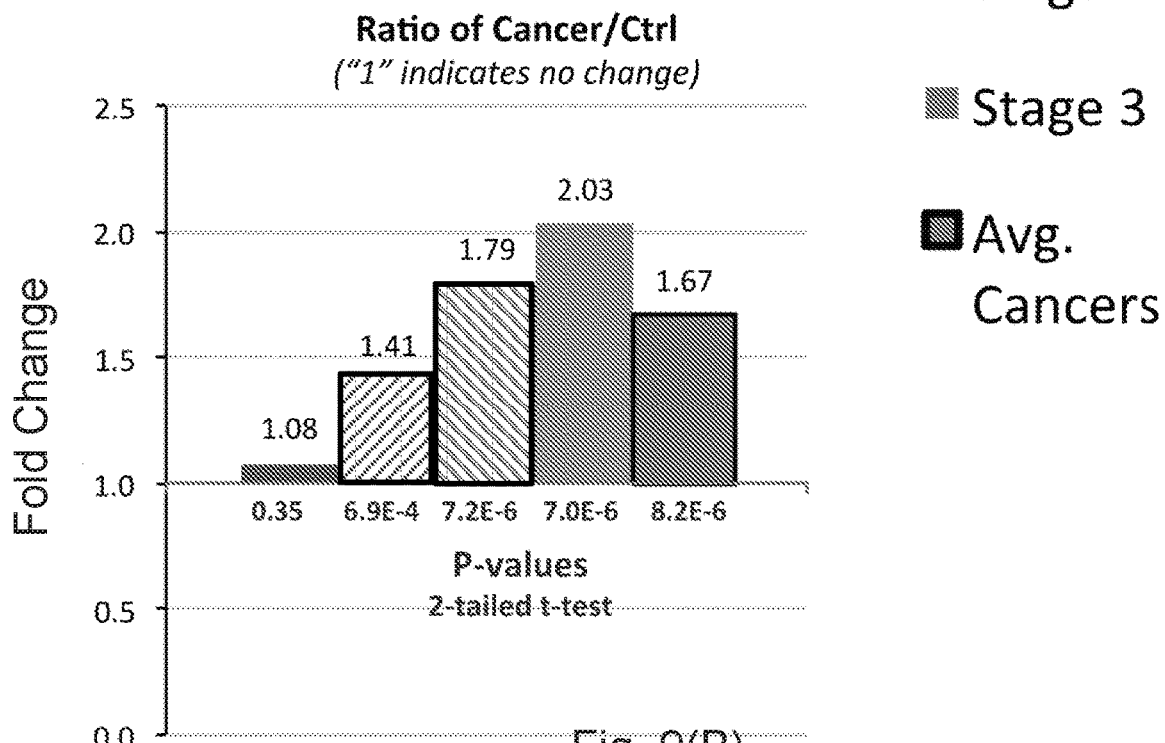
Fig. 9(B)

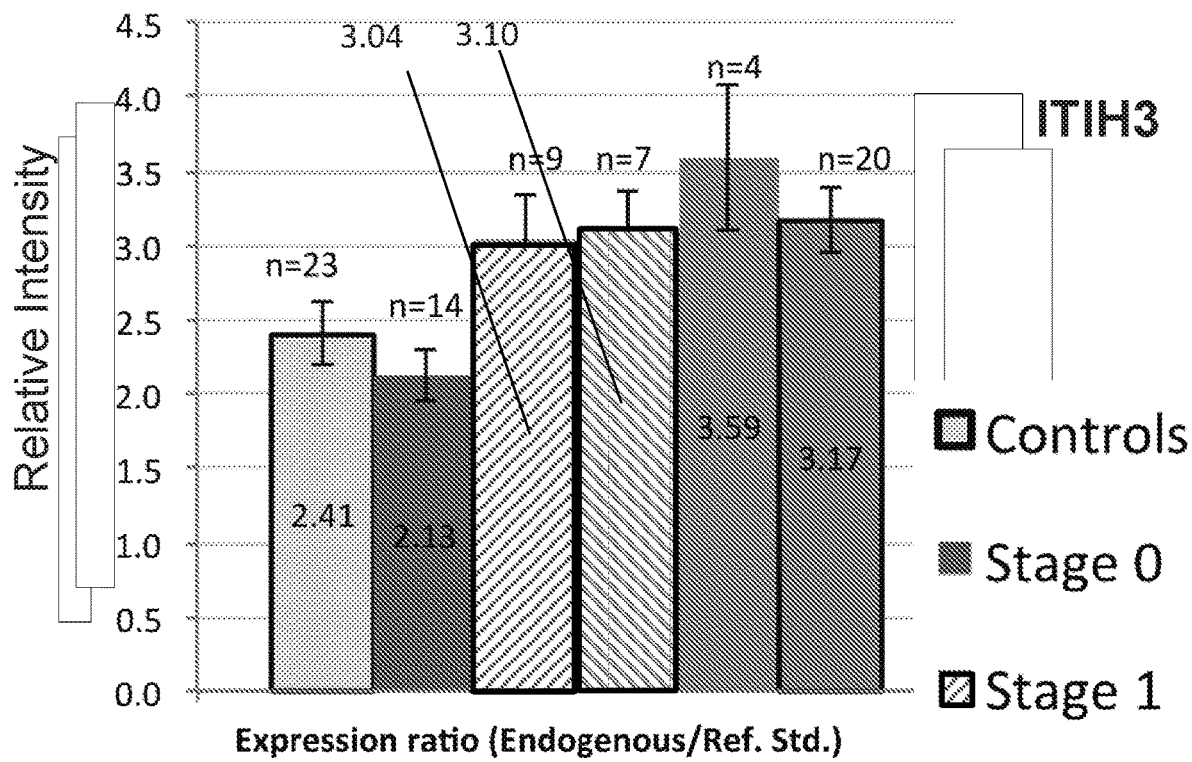
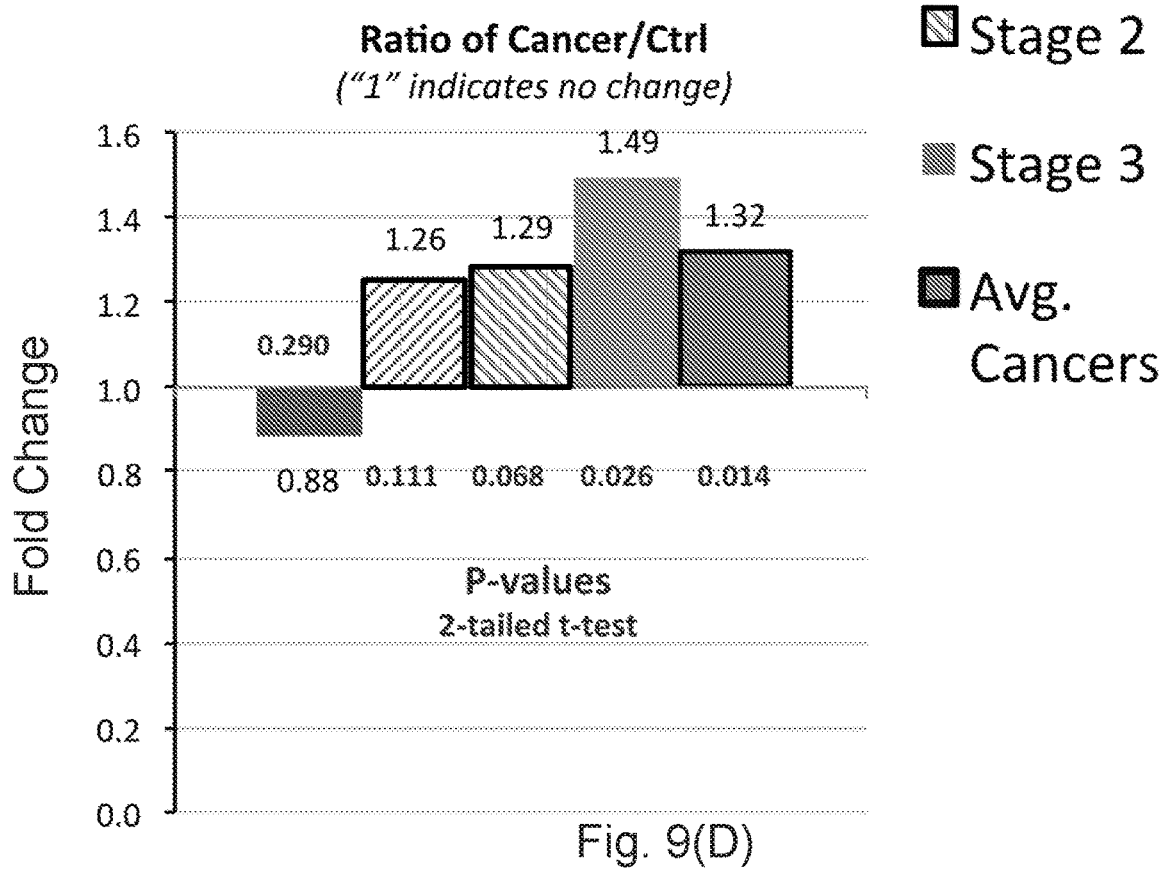
Fig. 9(D)

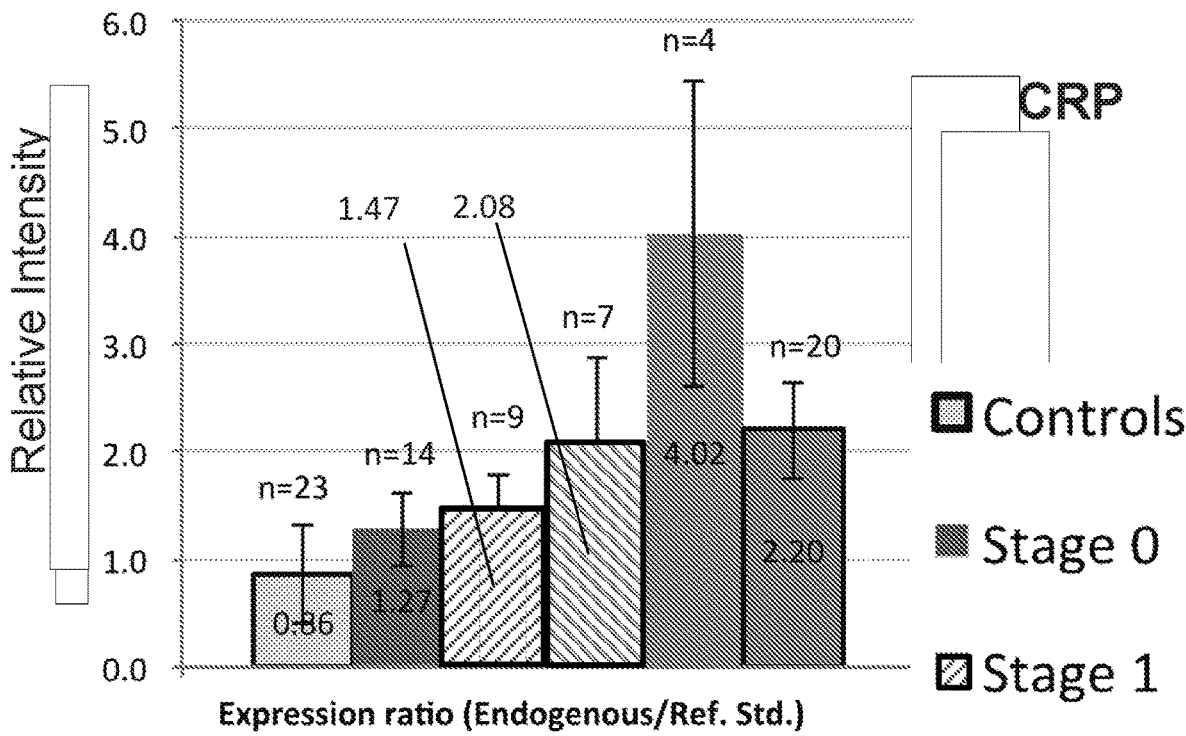
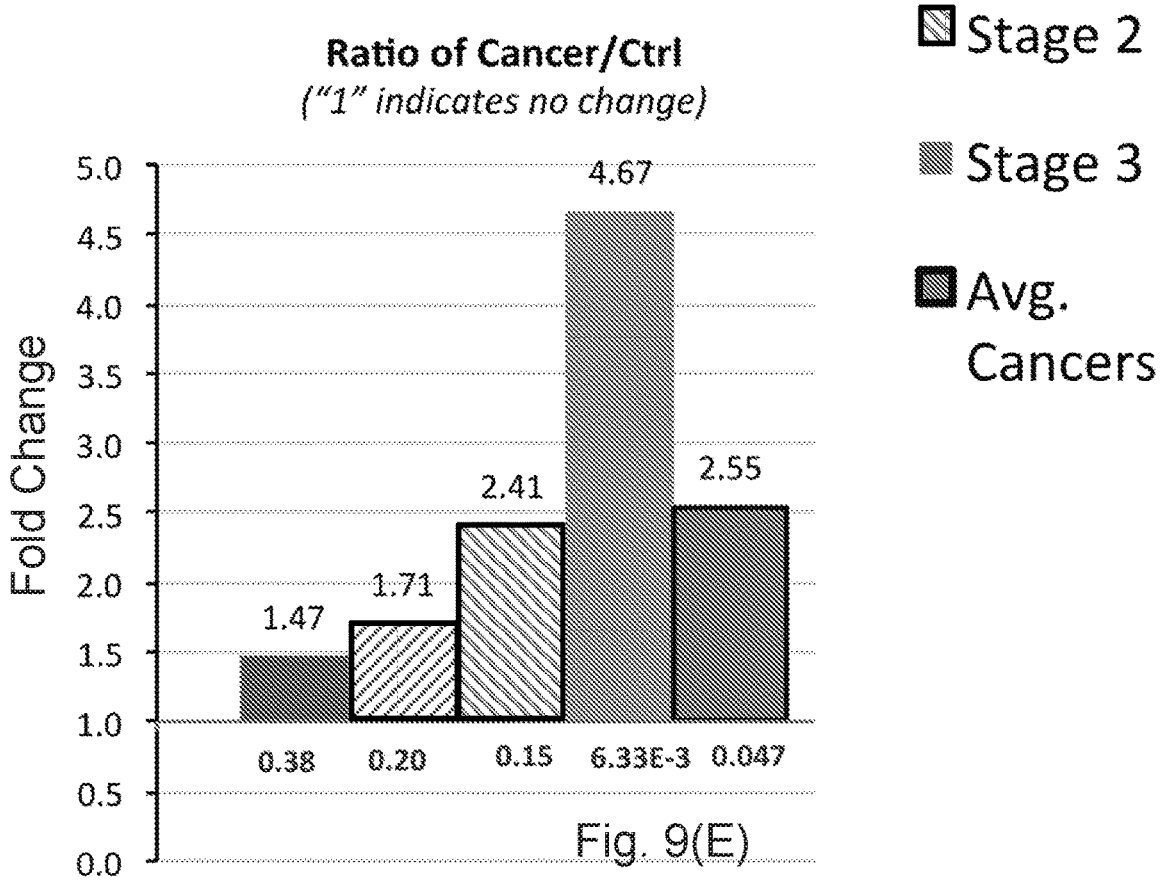
Fig. 9(E)

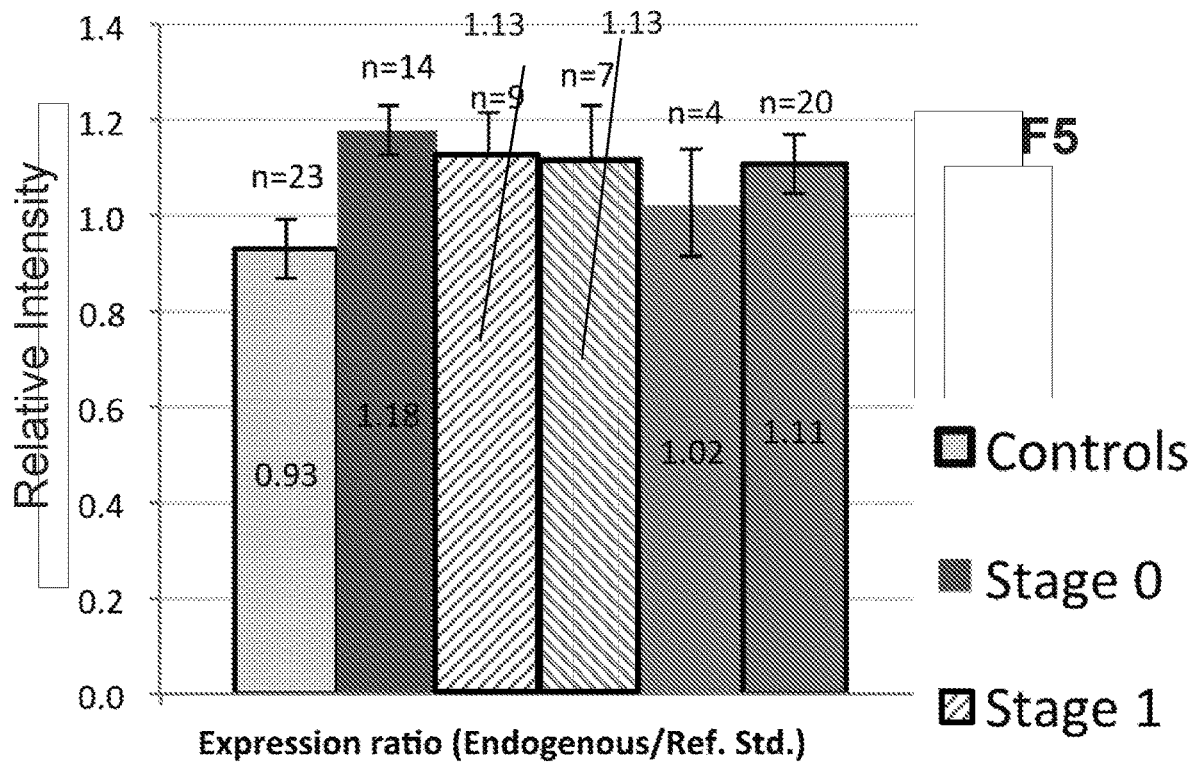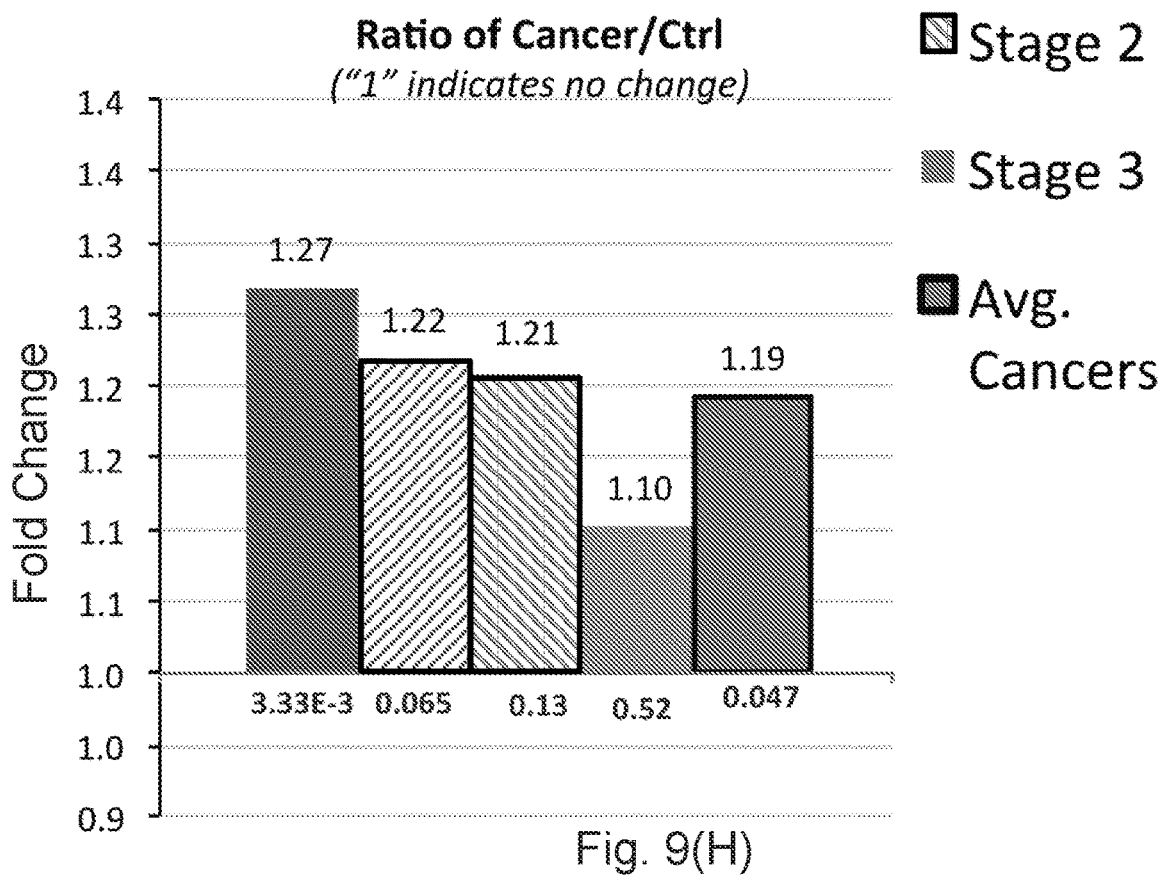
Fig. 9(H)

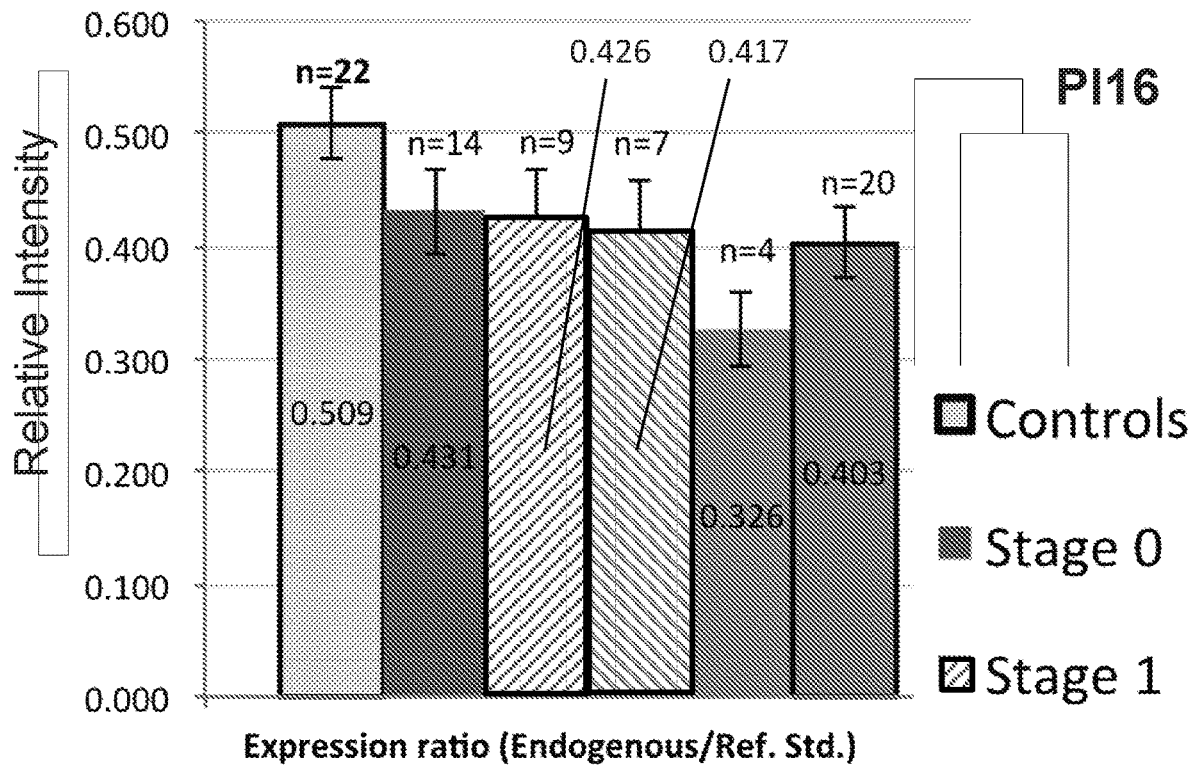
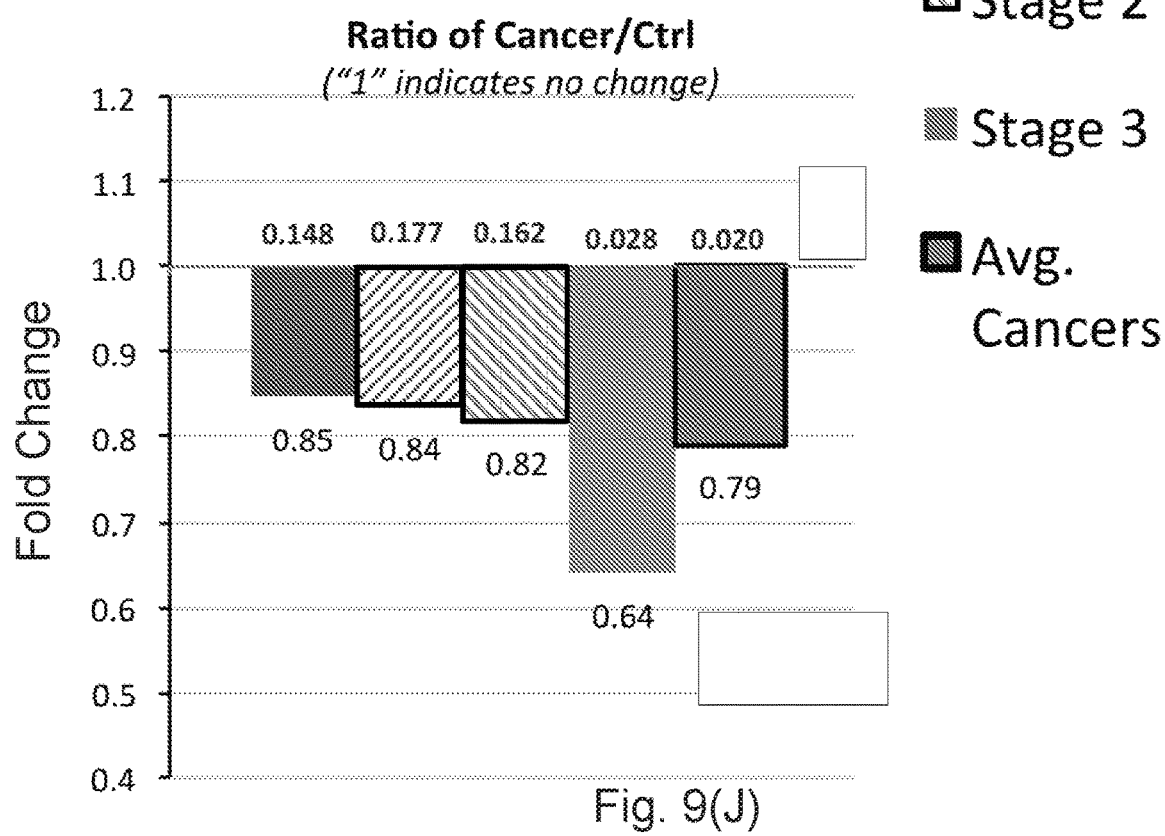
Fig. 9(J)

```
                            SEQUENCE LISTING

<160> NUMBER OF SEQ ID NOS: 91

<210> SEQ ID NO 1
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 1

Thr Ser Trp Gly Leu Glu Asn Glu Ala Leu Ile Val Arg
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic Biomarker Peptide

<400> SEQUENCE: 2

Phe Thr His Thr Glu Asn Gly Thr Asn Tyr Ile Val Thr Ala Thr Arg
1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 3

Ser Phe Thr Val Glu Glu Lys
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 4

Ala His Met Ser Tyr Leu Phe Ile Asp Lys
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic Biomarker Peptide

<400> SEQUENCE: 5

Phe Leu Val Asp Gln Ile Val Lys
1               5

<210> SEQ ID NO 6
<211> LENGTH: 10
<212> TYPE: PRT
<213> ORGANISM: Artificial Sequence
```

```
<220> FEATURE:
<223> OTHER INFORMATION: Synthetic Biomarker Peptide

<400> SEQUENCE: 6

Ile Val Ser Tyr Thr Thr Asp Leu Pro Arg
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic Biomarker Peptide

<400> SEQUENCE: 7

Thr Tyr Phe Phe Val Gly Asp Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 8

Thr Val Thr His Thr Leu Lys
1               5

<210> SEQ ID NO 9
<211> LENGTH: 15
<212> TYPE: PRT
<213> ORGANISM: Artificial Sequence
<220> FEATURE:
<223> OTHER INFORMATION: Synthetic Biomarker Peptide

<400> SEQUENCE: 9

Gln Asp His Ser Thr Met Asp Leu Ala Gln Gln Tyr Leu Glu Lys
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 10

Leu Asp Ser Asn Thr Val Glu Met Met His Lys Pro Arg
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Biomarker Peptide

<400> SEQUENCE: 11

Phe Leu Gly Leu Glu Met Thr Gly Lys
1               5

<210> SEQ ID NO 12
<211> LENGTH: 8
<212> TYPE: PRT
<213> ORGANISM: Artificial Sequence
<220> FEATURE:
```

```
<223> OTHER INFORMATION: Synthetic Biomarker Peptide

<400> SEQUENCE: 12

Ile Asp Ala Ala Val Phe Glu Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Biomarker Peptide

<400> SEQUENCE: 13

Gly Ser Gln Phe Trp Ala Val Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 14

Ser Asn Ser Trp Leu Leu Cys
1               5

<210> SEQ ID NO 15
<211> LENGTH: 20
<212> TYPE: PRT
<213> ORGANISM: Artificial Sequence
<220> FEATURE:
<223> OTHER INFORMATION: Synthetic Biomarker Peptide

<400> SEQUENCE: 15

Asp Asp Ala Phe Phe Ile Gly Ser Thr Leu Ala Thr Ile Ala Ser Thr
1               5                   10                  15

Val Tyr Ser Lys
            20

<210> SEQ ID NO 16
<211> LENGTH: 16
<212> TYPE: PRT
<213> ORGANISM: Artificial Sequence
<220> FEATURE:
<223> OTHER INFORMATION: Synthetic Biomarker Peptide

<400> SEQUENCE: 16

Glu Pro Thr Glu Thr Pro Asp Gln Phe Met Thr Ala Asp Glu Thr Arg
1               5                   10                  15

<210> SEQ ID NO 17
<211> LENGTH: 19
<212> TYPE: PRT
<213> ORGANISM: Artificial Sequence
<220> FEATURE:
<223> OTHER INFORMATION: Synthetic Biomarker Peptide

<400> SEQUENCE: 17

Thr Gln Trp Asn Pro Ile His Ser Asn Pro Glu Val Leu Leu Gln Thr
1               5                   10                  15

Thr Thr Arg

<210> SEQ ID NO 18
```

```
<211> LENGTH: 21
<212> TYPE: PRT
<213> ORGANISM: Artificial Sequence
<220> FEATURE:
<223> OTHER INFORMATION: Synthetic Biomarker Peptide

<400> SEQUENCE: 18

Ser Thr Pro Glu Gly Tyr Ile Leu His Thr Asp Leu Pro Thr Ser Gln
1               5                   10                  15

Pro Thr Gly Asp Arg
            20

<210> SEQ ID NO 19
<211> LENGTH: 11
<212> TYPE: PRT
<213> ORGANISM: Artificial Sequence
<220> FEATURE:
<223> OTHER INFORMATION: Synthetic Biomarker Peptide

<400> SEQUENCE: 19

Lys Pro Ser Glu Leu Asn Gly Glu Ala Ser Lys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Synthetic Biomarker Peptide

<400> SEQUENCE: 20

Asn Leu Gln Ser Val Asp Met Lys
1               5

<210> SEQ ID NO 21
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 21

Leu Val Ile Asn Ser Gly Asn Gly Thr Val Glu Asp Arg
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic Biomarker Peptide

<400> SEQUENCE: 22

Ala Phe Pro Ala Phe Val Leu Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 23

Leu Gly Thr Val Pro His Lys
1               5
```

<210> SEQ ID NO 24
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 24

Ala Ser Val Val Gln Val Gly Phe Pro Cys Leu Gly Lys
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic Biomarker Peptide

<400> SEQUENCE: 25

Tyr Gly Ala Ser Leu Met His Ala Pro Arg Pro Ala Gly Ala Gly Leu
1               5                   10                  15

Glu Arg

<210> SEQ ID NO 26
<211> LENGTH: 9
<212> TYPE: PRT
<213> ORGANISM: Artificial Sequence
<220> FEATURE:
<223> OTHER INFORMATION: Synthetic Biomarker Peptide

<400> SEQUENCE: 26

Thr Pro Gln Asn Ala Ile Phe Phe Lys
1               5

<210> SEQ ID NO 27
<211> LENGTH: 12
<212> TYPE: PRT
<213> ORGANISM: Artificial Sequence
<220> FEATURE:
<223> OTHER INFORMATION: Synthetic Biomarker Peptide

<400> SEQUENCE: 27

Thr Cys Gln Gln Ala Glu Cys Pro Gly Gly Cys Arg
1               5                   10

<210> SEQ ID NO 28
<211> LENGTH: 21
<212> TYPE: PRT
<213> ORGANISM: Artificial Sequence
<220> FEATURE:
<223> OTHER INFORMATION: Synthetic Biomarker Peptide

<400> SEQUENCE: 28

Ala Asp Ala Gly Gln Pro Pro Glu Glu Ser Leu Tyr Leu Trp Ile Asp
1               5                   10                  15

Ala His Gln Ala Arg
                20

<210> SEQ ID NO 29
<211> LENGTH: 12
<212> TYPE: PRT
<213> ORGANISM: Artificial Sequence
<220> FEATURE:
<223> OTHER INFORMATION: Synthetic Biomarker Peptide

<400> SEQUENCE: 29

```
Leu Trp Ser Ile Leu Pro Cys Leu Leu Leu Arg
1               5                   10
```

<210> SEQ ID NO 30
<211> LENGTH: 19
<212> TYPE: PRT
<213> ORGANISM: Artificial Sequence
<220> FEATURE:
<223> OTHER INFORMATION: Synthetic Biomarker Peptide

<400> SEQUENCE: 30

```
Val Val Gly Gly Lys Pro Ala Glu Met Gly Asp Tyr Pro Trp Gln Val
1               5                   10                  15

Ala Ile Lys
```

<210> SEQ ID NO 31
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 31

```
Leu Pro Tyr Gln Cys Pro Lys
1               5
```

<210> SEQ ID NO 32
<211> LENGTH: 8
<212> TYPE: PRT
<213> ORGANISM: Artificial Sequence
<220> FEATURE:
<223> OTHER INFORMATION: Synthetic Biomarker Peptide

<400> SEQUENCE: 32

```
Val Phe Cys Gln Pro Trp Gln Lys
1               5
```

<210> SEQ ID NO 33
<211> LENGTH: 9
<212> TYPE: PRT
<213> ORGANISM: Artificial Sequence
<220> FEATURE:
<223> OTHER INFORMATION: Synthetic Biomarker Peptide

<400> SEQUENCE: 33

```
Gly Tyr Pro Thr Tyr Cys His Leu Lys
1               5
```

<210> SEQ ID NO 34
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 34

```
Ser Phe Glu Cys Leu His Pro Glu Ile Lys
1               5                   10
```

<210> SEQ ID NO 35
<211> LENGTH: 8
<212> TYPE: PRT
<213> ORGANISM: Artificial Sequence
<220> FEATURE:
<223> OTHER INFORMATION: Synthetic Biomarker Peptide

```
<400> SEQUENCE: 35

Phe Asn Ile Pro Val Asn His Lys
1               5

<210> SEQ ID NO 36
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 36

Ile Asn Ser Thr Glu Cys Leu His Val Arg
1               5                   10

<210> SEQ ID NO 37
<211> LENGTH: 19
<212> TYPE: PRT
<213> ORGANISM: Artificial Sequence
<220> FEATURE:
<223> OTHER INFORMATION: Synthetic Biomarker Peptide

<400> SEQUENCE: 37

Phe Asn Val Ser Leu Ile Tyr Gly Ser Thr Asp Thr Glu Gly Ile Val
1               5                   10                  15

Gln Val Lys

<210> SEQ ID NO 38
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 38

Ile Ser His Glu Leu Glu Ser Ser Ser Ser Glu Val Asn
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic Biomarker Peptide

<400> SEQUENCE: 39

Ser Ile Ser Thr Ile Ile Asn Val Phe His Gln Tyr Ser Arg
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Synthetic Biomarker Peptide

<400> SEQUENCE: 40

Tyr Gly His Pro Asp Thr Leu Asn Lys
1               5

<210> SEQ ID NO 41
<211> LENGTH: 17
<212> TYPE: PRT
<213> ORGANISM: Artificial Sequence
<220> FEATURE:
<223> OTHER INFORMATION: Synthetic Biomarker Peptide
```

```
<400> SEQUENCE: 41

Leu Ser Thr Ser Trp Thr Glu Glu Asp Val Asn Asp Asn Thr Leu Phe
1               5                   10                  15

Lys

<210> SEQ ID NO 42
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 42

Ala Thr Cys Leu Leu Gly Arg
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Biomarker Peptide

<400> SEQUENCE: 43

Glu Glu Cys Cys Ser Thr Gly Arg
1               5

<210> SEQ ID NO 44
<211> LENGTH: 15
<212> TYPE: PRT
<213> ORGANISM: Artificial Sequence
<220> FEATURE:
<223> OTHER INFORMATION: Synthetic Biomarker Peptide

<400> SEQUENCE: 44

Trp Met Ile Phe Asn Gly Gly Ala Pro Asn Cys Ile Pro Cys Lys
1               5                   10                  15

<210> SEQ ID NO 45
<211> LENGTH: 9
<212> TYPE: PRT
<213> ORGANISM: Artificial Sequence
<220> FEATURE:
<223> OTHER INFORMATION: Synthetic Biomarker Peptide

<400> SEQUENCE: 45

Ser Ile Gly Leu Ala Tyr Glu Gly Lys
1               5

<210> SEQ ID NO 46
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 46

Glu Ala Ala Cys Ser Ser Gly Val Leu Leu Glu Val Lys
1               5                   10

<210> SEQ ID NO 47
<211> LENGTH: 12
<212> TYPE: PRT
<213> ORGANISM: Artificial Sequence
<220> FEATURE:
```

```
<223> OTHER INFORMATION: Synthetic Biomarker Peptide

<400> SEQUENCE: 47

Cys Ser Leu Cys Asp Glu Leu Cys Pro Asp Ser Lys
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic Biomarker Peptide

<400> SEQUENCE: 48

Ser Cys Glu Asp Ile Gln Cys Gly Gly Gly Lys
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 49

Glu Ala Cys Leu Asp Pro Glu Ala Pro Met Val Gln Lys
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 50

Leu Asp Gln Asn Gln Val Arg
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Biomarker Peptide

<400> SEQUENCE: 51

Met Ile Pro Met Ser Arg
1               5

<210> SEQ ID NO 52
<211> LENGTH: 15
<212> TYPE: PRT
<213> ORGANISM: Artificial Sequence
<220> FEATURE:
<223> OTHER INFORMATION: Synthetic Biomarker Peptide

<400> SEQUENCE: 52

Thr Leu Phe Leu Leu Ala Leu Leu Gly Gly Val Ser Gly Leu Arg
1               5                   10                  15

<210> SEQ ID NO 53
<211> LENGTH: 11
<212> TYPE: PRT
<213> ORGANISM: Artificial Sequence
<220> FEATURE:
<223> OTHER INFORMATION: Synthetic Biomarker Peptide
```

```
<400> SEQUENCE: 53

Ser Ser Ala Ala Leu Asn Thr Leu Val Leu Arg
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 54

Leu Leu Asp Val Ala Glu Leu Gly Thr Leu
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 55

Ser Leu Pro Pro Gly Leu Phe Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 56

Asp Leu Val Asp Leu Cys Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 57

Leu His Leu Glu Gly Asn Arg
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 58

Glu Asn Gln Leu Gln Glu Ala Ser Ala Arg
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic Biomarker Peptide
```

```
<400> SEQUENCE: 59

Asn Leu Tyr Leu Ser Cys Val Met Lys
1               5

<210> SEQ ID NO 60
<211> LENGTH: 11
<212> TYPE: PRT
<213> ORGANISM: Artificial Sequence
<220> FEATURE:
<223> OTHER INFORMATION: Synthetic Biomarker Peptide

<400> SEQUENCE: 60

Cys Leu Val Leu Ser Asp Pro Cys Glu Leu Lys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic Biomarker Peptide

<400> SEQUENCE: 61

Asp Gly Thr Pro Thr Leu Gln Leu Glu Ser Val Asp Pro Lys
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 62

Ser Leu Ser Gln Gln Ile Glu Asn Ile Arg
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 63

Ile Pro Leu Glu Asn Leu Gln Ile Ile Arg
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 64

Glu Val Ser Phe Asp Val Glu Leu Pro Lys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 65
```

Ala Tyr Val Ala Phe Pro Asp Phe Phe Arg
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 66

Asn Phe Phe Asn Pro Pro Ile Ile Ser Arg
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 67

Leu Trp Trp Leu Asp Leu Lys
1               5

<210> SEQ ID NO 68
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 68

Thr Ile Glu Ala Glu Ala Ala His Gly Thr Val Thr Arg
1               5                   10

<210> SEQ ID NO 69
<211> LENGTH: 16
<212> TYPE: PRT
<213> ORGANISM: Artificial Sequence
<220> FEATURE:
<223> OTHER INFORMATION: Synthetic Biomarker Peptide

<400> SEQUENCE: 69

Glu Ala Glu Ala Ala Ile Tyr His Leu Gln Leu Phe Glu Glu Leu Arg
1               5                   10                  15

<210> SEQ ID NO 70
<211> LENGTH: 7
<212> TYPE: PRT
<213> ORGANISM: Artificial Sequence
<220> FEATURE:
<223> OTHER INFORMATION: Synthetic Biomarker Peptide

<400> SEQUENCE: 70

Val Leu Glu Pro Thr Leu Lys
1               5

<210> SEQ ID NO 71
<211> LENGTH: 12
<212> TYPE: PRT
<213> ORGANISM: Artificial Sequence
<220> FEATURE:
<223> OTHER INFORMATION: Synthetic Biomarker Peptide

<400> SEQUENCE: 71

```
Phe Glu Asp Gly Val Leu Asp Pro Asp Tyr Pro Arg
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Synthetic Biomarker Peptide

<400> SEQUENCE: 72

Phe Ala His Thr Val Val Thr Ser Arg
1               5

<210> SEQ ID NO 73
<211> LENGTH: 12
<212> TYPE: PRT
<213> ORGANISM: Artificial Sequence
<220> FEATURE:
<223> OTHER INFORMATION: Synthetic Biomarker Peptide

<400> SEQUENCE: 73

Tyr Gly Phe Ile Glu Gly His Val Val Ile Pro Arg
1               5                   10

<210> SEQ ID NO 74
<211> LENGTH: 9
<212> TYPE: PRT
<213> ORGANISM: Artificial Sequence
<220> FEATURE:
<223> OTHER INFORMATION: Synthetic Biomarker Peptide

<400> SEQUENCE: 74

Thr Leu Thr Leu Leu Ser Val Thr Arg
1               5

<210> SEQ ID NO 75
<211> LENGTH: 14
<212> TYPE: PRT
<213> ORGANISM: Artificial Sequence
<220> FEATURE:
<223> OTHER INFORMATION: Synthetic Biomarker Peptide

<400> SEQUENCE: 75

Leu Cys Gly Thr Phe Leu Gly Gly Pro Lys Pro Pro Gln Arg
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 76

Val Ala Ala Gly Ala Phe Gln Gly Leu Arg
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic Biomarker Peptide

<400> SEQUENCE: 77

Gly Tyr Val Ile Ile Lys Pro Leu Val Trp Val
```

<210> SEQ ID NO 78
<211> LENGTH: 11
<212> TYPE: PRT
<213> ORGANISM: Artificial Sequence
<220> FEATURE:
<223> OTHER INFORMATION: Synthetic Biomarker Peptide

<400> SEQUENCE: 78

```
Ile Phe Phe Glu Ser Val Tyr Gly Gln Cys Lys
1               5                   10
```

<210> SEQ ID NO 79
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 79

```
Glu Ser Asp Thr Ser Tyr Val Ser Leu Lys
1               5                   10
```

<210> SEQ ID NO 80
<211> LENGTH: 9
<212> TYPE: PRT
<213> ORGANISM: Artificial Sequence
<220> FEATURE:
<223> OTHER INFORMATION: Synthetic Biomarker Peptide

<400> SEQUENCE: 80

```
Asp Leu Pro His Ile Thr Val Asp Arg
1               5
```

<210> SEQ ID NO 81
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 81

```
Val Phe Ser Leu Gln Trp Gly Glu Val Lys
1               5                   10
```

<210> SEQ ID NO 82
<211> LENGTH: 15
<212> TYPE: PRT
<213> ORGANISM: Artificial Sequence
<220> FEATURE:
<223> OTHER INFORMATION: Synthetic Biomarker Peptide

<400> SEQUENCE: 82

```
Phe Thr Val Asp Arg Pro Phe Leu Phe Leu Ile Tyr Glu His Arg
1               5                   10                  15
```

<210> SEQ ID NO 83
<211> LENGTH: 17
<212> TYPE: PRT
<213> ORGANISM: Artificial Sequence
<220> FEATURE:
<223> OTHER INFORMATION: Synthetic Biomarker Peptide

<400> SEQUENCE: 83

```
Ser Ser Val Tyr Ala Asn Ala Phe Pro Ser Thr Pro Val Asn Pro Leu
1               5                   10                  15
```

Arg

<210> SEQ ID NO 84
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 84

Leu Ala Gly Ala Pro Ser Glu Asp Pro Gln Phe Pro Lys
1               5                   10

<210> SEQ ID NO 85
<211> LENGTH: 15
<212> TYPE: PRT
<213> ORGANISM: Artificial Sequence
<220> FEATURE:
<223> OTHER INFORMATION: Synthetic Biomarker Peptide

<400> SEQUENCE: 85

Ala Glu Glu Tyr Glu Phe Leu Thr Pro Val Glu Glu Ala Pro Lys
1               5                   10                  15

<210> SEQ ID NO 86
<211> LENGTH: 10
<212> TYPE: PRT
<213> ORGANISM: Artificial Sequence
<220> FEATURE:
<223> OTHER INFORMATION: Synthetic Biomarker Peptide

<400> SEQUENCE: 86

Trp Asp Glu Glu Leu Ala Ala Phe Ala Lys
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Synthetic Biomarker Peptide

<400> SEQUENCE: 87

Gly Pro Phe Pro Gln Glu Leu Val Arg
1               5

<210> SEQ ID NO 88
<211> LENGTH: 11
<212> TYPE: PRT
<213> ORGANISM: Artificial Sequence
<220> FEATURE:
<223> OTHER INFORMATION: Synthetic Biomarker Peptide

<400> SEQUENCE: 88

Trp Glu Tyr Tyr Asp Ser Val Tyr Thr Glu Arg
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Synthetic Biomarker Peptide

<400> SEQUENCE: 89

Val Thr Gly Val Val Leu Phe Arg

```
<210> SEQ ID NO 90
<211> LENGTH: 17
<212> TYPE: PRT
<213> ORGANISM: Artificial Sequence
<220> FEATURE:
<223> OTHER INFORMATION: Synthetic Biomarker Peptide

<400> SEQUENCE: 90

Asp Val Asp Ile Asp Ser Tyr Pro Asp Glu Glu Leu Pro Cys Ser Ala
1               5                   10                  15

Arg

<210> SEQ ID NO 91
<211> LENGTH: 13
<212> TYPE: PRT
<213> ORGANISM: Artificial Sequence
<220> FEATURE:
<223> OTHER INFORMATION: Synthetic Biomarker Peptide

<400> SEQUENCE: 91

Gly Phe Gly Pro Pro Ala Thr Asn Gln Phe Thr Thr Lys
1               5                   10
```

METHODS FOR DETECTION AND TREATMENT OF COLORECTAL CANCER

This application is a national stage application under 35 U.S.C. § 371 of International Application No. PCT/US2015/065049, filed Dec. 10, 2015, which claims the benefit of U.S. Provisional Patent Application Ser. No. 62/090,800, filed Dec. 11, 2014 the disclosures of which are explicitly incorporated by reference herein.

STATEMENT OF GOVERNMENT RIGHTS

This invention was made with government support under CA063677 awarded by the National Institutes of Health. The government has certain rights in the invention.

The contents of the text file submitted electronically herewith are incorporated herein by reference in their entirety: A computer readable format copy of the Sequence Listing (filename: 14-1895-WO_SeqList_ST25.txt, date recorded: Dec. 10, 2015, file size 21 KB).

BACKGROUND OF THE INVENTION

Field of the Invention

This invention provides methods, reagents, and diagnostic and prognostic markers useful for minimally invasive identification, diagnosis, and therapeutic intervention in individuals with colorectal cancers, or individuals who may be susceptible to developing colorectal cancers. Particular embodiments of the invention employ serum biomarkers present in proteomic and transcriptome screens that identify individuals likely to develop colorectal cancer and provide a basis for making decisions regarding more invasive diagnostic methods (such as colonoscopies), particularly in individuals without other indicators for such procedures. Additional particular embodiments provide a panel of serum biomarkers for use in the methods provided herein.

Description of Related Art

Colorectal cancer is a major cause of cancer-related morbidity and mortality in modernized nations, and is increasing in frequency in the developing world (Jemal et al., *CA Cancer J Clin* 2011, 61, (2), 69-90.). While early detection of localized colorectal cancer often leads to complete cure by polypectomy or surgery, the modalities for early detection are currently limited in sensitivity and specificity, have low patient adherence to screening recommendations, and place a strain on the capacity of clinical gastroenterologists (Hopchik, *Gastroenterol Nurs* 2013, 36, (4), 289-90, 331; Kriza et al., *Eur J Radiol* 2013, 82, (11), e629-36). The current recommended screening procedures (colonoscopy, CT scan, or Fecal Occult Blood Test) can be non-specific, insensitive for the earliest operable lesions, or highly invasive (Leng et al., *J Gerontol A Biol Sci Med Sci* 2008, 63, (8), 879-84; Burt et al., *J Natl Compr Canc Netw* 2013, 11, (12), 1538-75). By contrast, a detection modality based upon blood or serum samples can achieve much broader patient compliance and clinical coverage.

SUMMARY OF THE INVENTION

This invention provides methods, reagents, and diagnostic and prognostic markers useful for minimally invasive identification, diagnosis, and therapeutic intervention in individuals with colorectal cancers, or individuals who may be susceptible to developing colorectal cancers. In certain embodiments the invention provides serum biomarkers, and methods of using those serum biomarkers, including methods of screening, detection, monitoring, treatment, and prognostic evaluation of colorectal cancers. Other embodiments provide synthetic peptides useful for minimally invasive identification, diagnosis, and therapeutic intervention in patients with colorectal cancers, or those patients who may be susceptible to developing colorectal cancers.

In one aspect, provided herein are methods for identifying a subject with cancerous or pre-cancerous lesions in the colon, the method comprising: (a) assaying a biosample from the subject for one or a plurality of protein biomarkers, wherein the protein biomarkers are epidermal growth factor receptor, leucine-rich alpha-2 glycoprotein, inter-alpha trypsin inhibitor heavy chain 3, inter-alpha trypsin inhibitor heavy chain 4, dipeptidyl peptidase 4, peptidase inhibitor 16, coagulation factor V, C-reactive protein, Rho-GDP dissociation inhibitor 1 isoform A, hemopexin, extracellular superoxide dismutase[Cu—Zn], thrombospondin-4, collagen alpha-1(l) chain, cadherin-2, or vitronectin; (b) determining the level of one or a plurality of the protein biomarkers in the biosample; and (c) identifying the subject as having a lesion of the colon when the level of one or a plurality of the protein biomarkers is different than a level detected in a subject without polyp formation in the colon.

In particular embodiments, the lesion identified and treated by the presently disclosed methods comprises a pre-cancerous condition in the colon. For example, embodiments of the present disclosure provide methods of identifying dysplasia, an aberrant crypt, or a benign polyp in the colon.

In some embodiments, the lesion identified by the presently disclosed methods comprises polyp formation. In particular embodiments, the polyp is an adenoma or a carcinoma. In other embodiments, the carcinoma is classified as stage 1, stage 2, stage 3, or stage 4. In still other embodiments, methods of the present disclosure are useful for identifying a carcinoma as stage 1, stage 2, stage 3, or stage 4 carcinoma.

In particular embodiments, the methods are performed on biosamples such as, without limitation, blood, plasma, or serum.

In other embodiments, the biosample is assayed by a method comprising: (a) selecting one or more synthetic peptides with homology to one or a plurality of the protein biomarkers; (b) combining the synthetic peptides with the biosample; and (c) subjecting the combination to a physical separation method. In particular embodiments the physical separation method is liquid chromatography. In other particular embodiments, the synthetic peptides are isotopically labeled. In yet other particular embodiments the assaying step comprises an immunologic assay such as enzyme-linked immunosorbent assay.

In other embodiments the determining step comprises mass spectrometry.

In other embodiments, the method further comprises the step of administering treatment to a subject identified as having polyp formation in the colon. In yet other embodiments, the method further comprises the step of performing a colonoscopy to a subject identified as having a having polyp formation in the colon. In other embodiments, the method is non-invasive.

In another aspect, provided herein is a method for screening individuals to determine a need for a colonoscopy comprising (a) assaying a biosample from the subject for one or a plurality of protein biomarkers, wherein the protein biomarkers are epidermal growth factor receptor, leucine-rich alpha-2 glycoprotein, inter-alpha trypsin inhibitor heavy chain 3, inter-alpha trypsin inhibitor heavy chain 4, dipeptidyl peptidase 4, peptidase inhibitor 16, coagulation factor V, C-reactive protein, Rho-GDP dissociation inhibitor 1 isoform A, hemopexin, extracellular superoxide dismutase [Cu—Zn], thrombospondin-4, collagen alpha-1(l) chain, cadherin-2, and vitronectin; (b) determining the level of one or a plurality of the protein biomarkers in the biosample; and (c) identifying the individual as needing a colonoscopy when the level of one or a plurality of the protein biomarkers is different than the level detected in a subject without polyp formation in the colon.

In still other embodiments, methods are provided for identifying individuals who would benefit from further clinical assessment or treatment, including but not limited to, further assessment or treatment by colonoscopy or polypectomy procedures. In other embodiments, post-surgical or post-polypectomy patient monitoring is provided. In still other embodiments, the disclosed methods are useful for monitoring responsiveness of a patient to chemopreventative or chemotherapeutic agents.

In addition, methods are provided that are capable of enhancing utility of currently existing colorectal screening, diagnosis, prognosis and treatment methodologies Accordingly, certain embodiments disclosed here are useful in combination with other techniques known to the art, including, without limitation, colonoscopy, sigmoidoscopy, CT scan, or Fecal Occult Blood Test, Fecal Immunochemical Test, and other Fecal-based screening or diagnostic techniques.

Also provided here are protein biomarkers with clinical application, including without limitation application to screening, diagnosis, prognosis, and treatment of colorectal cancers and precancerous conditions. In certain embodiments, protein biomarkers comprise epidermal growth factor receptor, leucine-rich alpha-2 glycoprotein, inter-alpha trypsin inhibitor heavy chain 3, inter-alpha trypsin inhibitor heavy chain 4, dipeptidyl peptidase 4, peptidase inhibitor 16, coagulation factor V, C-reactive protein, Rho-GDP dissociation inhibitor 1 isoform A, hemopexin, extracellular superoxide dismutase[Cu—Zn], thrombospondin-4, collagen alpha-1(l) chain, cadherin-2, or vitronectin or any combination thereof useful for prognosis, diagnosis or treatment.

In certain embodiments, a panel of protein biomarkers is provided comprised of a subset of the protein biomarkers disclosed herein. In particular embodiments, methods are provided comprising (a) assaying a biosample from the subject for the levels of a panel of protein biomarkers; (b) determining the levels of the panel of protein biomarkers in the biosample; and (c) identifying the individual as needing a colonoscopy when the level of one or a plurality of the protein biomarkers in the panel is different than the levels detected in a subject without polyp formation in the colon. In some embodiments, a panel of protein biomarkers is provided comprising at least the protein biomarkers: LRG1, F5, VTN, MMP7, MMP10, CD44, ITIH3, ITIH4, HPX, CFI, SOD3, and COL1A1. In other embodiments, a panel of protein biomarkers is provided comprising at least the protein biomarkers: EGFR, LRG1, ITIH4, and F5. In still other embodiments, a panel of protein biomarkers is provided comprising at least the protein biomarkers: DPP4, LRG1, ITIH4, VTN, HPX, EGFR and F5. In yet further embodiments, a panel of protein biomarkers is provided comprising at least the protein biomarkers: EGFR, LRG1, ITIH3, ITIH4, DPP4, PI16, F5, CRP, and ARHGDIA.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

FIG. 2 presents the criteria for the selection of peptides for targeted analyses. "Tier 1" criteria must be met in order to use a peptide for a targeted analysis. "Tier 2" criteria maximize chances that the endogenous peptide is visible in the targeted mass spectrometry assay. "Tier 3" criteria should be considered for targeted analysis in multiple species.

FIGS. 9A-9J present the results for the indicated biomarkers studied in a human population comprised of a healthy ("control") group, and individuals with precancerous (stage 0) or cancerous (stage 1-3) colon lesions. Top panels show bar plots of the observed biomarker levels in patient groups assessed relative to synthetic reference standards. Data are expressed as a ratio of endogenous to the synthetic peptide reference standards. Patient groups comprise healthy subjects (control), or those with stage 0, stage 1, stage 2, or stage 3 lesions. Average ("Avg.") Cancers comprise stages 0-3 combined. The "n-" value denotes the number of patients in each group. Error bars represent average biological standard error. Bottom panels show bar plots of the ratio of observed biomarker expression levels in subjects with colon lesions (stages 0-3, and the combined average) relative to the same biomarker expression levels in healthy control subjects. Each bar shows the fold change of the indicated biomarkers between control subjects and those with colon lesions. Quantitated ratios are shown for each bar plot, along with P-values from 2-tailed t-tests for each ratio.

DETAILED DESCRIPTION OF THE INVENTION

Figure 1:
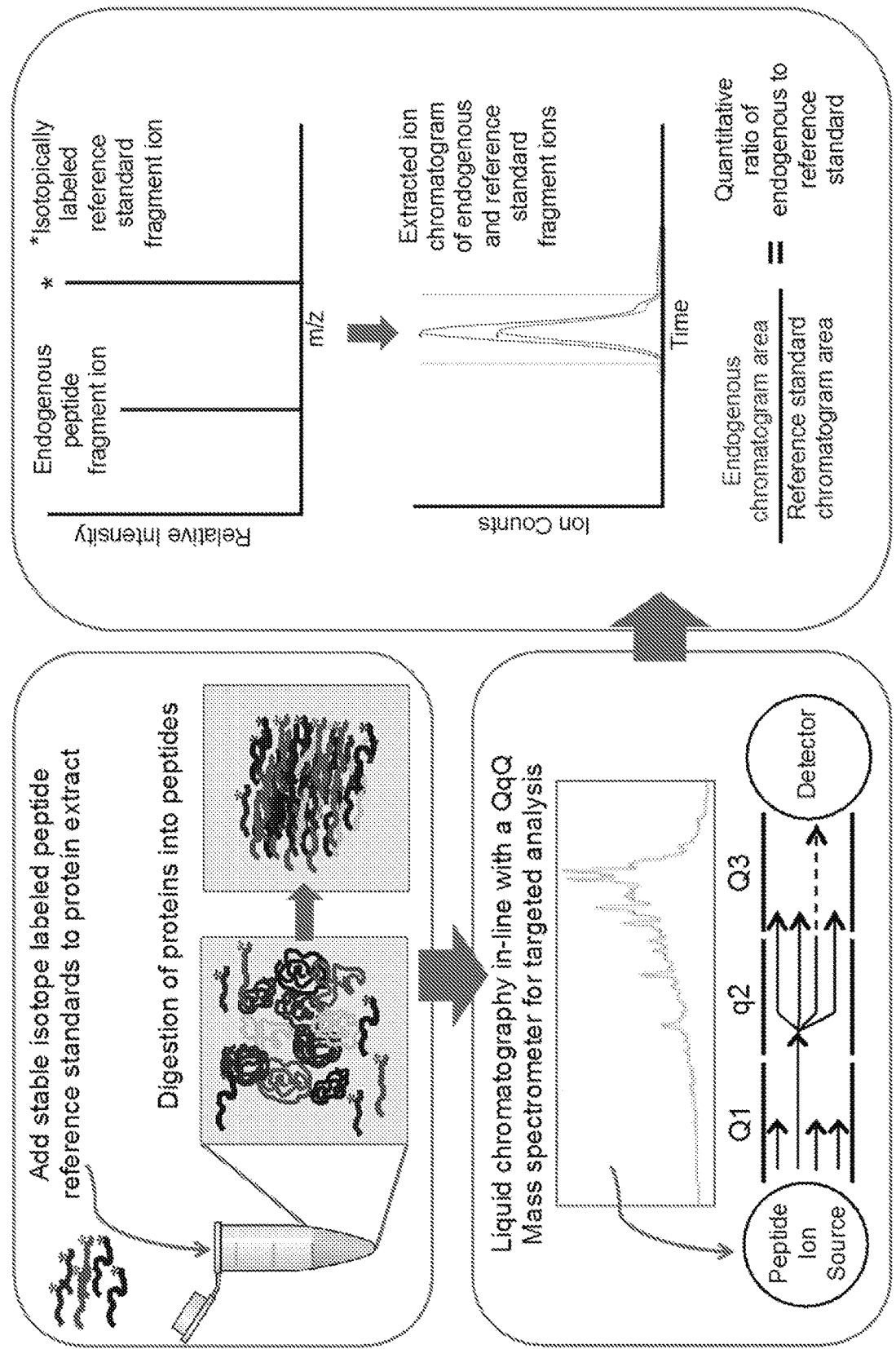
FIG. 1 illustrates the workflow of a targeted quantitative proteomics experiment. Stable isotope labeled reference standards are spiked into a protein extract prior to enzymatic digestion. Peptides are chromatographically separated by reversed-phase chromatography followed by analysis in-line with a triple quadrupole mass spectrometer (QQQ-MS) where targeted precursor and fragment ion masses (transitions) are selected. Quantification occurs by comparing the extracted ion chromatogram areas of the endogenous and reference standard fragment ions. Such a targeted quantitative proteomics procedure is also known as a selected reaction monitoring (SRM), or multiple reaction monitoring (MRM), procedure.

All publications, patents and patent applications cited herein are hereby expressly incorporated by reference for all purposes.

Provided herein are non-invasive methods for identifying and treating subjects with cancerous or pre-cancerous lesions of the colon. A "lesion" as used herein refers to an abnormal region of the colon, and includes dysplasia, aberrant crypts, as well as benign or cancerous polyps.

A "polyp" as used herein refers to a polyp present in any of the four stages of colorectal cancer, or to a polyp of a precancerous condition. As used herein, "colorectal cancer" refers to a malignant condition comprised of any of the 4 stages, ranging from stage 1 to stage 4, classified by the American Joint Committee on Cancer (AJCC) according to the TNM system (which evaluates histological properties (T), tumor presence in nearby lymph nodes (N), and metastatic spread (M)) (Gunderson, L. L. et al., *J Clin Oncol* 2010, 28, (2), 264-71.; Greene, F. L., *Bull Am Coll Surg* 2002, 87, (7), 13-5). (Table 1.)

TABLE 1

TNM staging system by the American Joint Committee on Cancer (AJCC), 6th Edition

| AJCC Stage | TNM Stage | TNM staging criteria |
|---|---|---|
| Stage 0 | Tis N0 M0 | Tis: Tumor is confined to mucosal layer. Cancer-in-situ |
| Stage I | T1 N0 M0 | T1: Tumor invades submucosa |
| Stage I | T2 N0 M0 | T2: Tumor invades muscle layer |
| Stage II-A | T3 N0 M0 | T3: Tumor invades serosa or beyond without metastasis to other organs |
| Stage II-B | T4 N0 M0 | T4: Tumor invades adjacent organs or perforates the visceral peritoneum |
| Stage III-A | T1-2 N1 M0 | N1: Metastasis to 1-3 lymphnodes. T1 or T2 |
| Stage III-B | T3-4 N1 M0 | N1, and T3 or T4 |
| Stage III-C | any T, N2 M0 | N2: Metastasis to 4 or more regional lymphnodes. Any T |
| Stage IV | any T, any N, M1 | M1: Distant metastases, Any T, any N |

A "pre-cancerous condition" as used herein refers to a patient with a pre-invasive, pre-metastatic lesion that disposes a person to colon cancer. Examples include dysplasia, the presence of aberrant crypts, and the presence of adenomas. The AJCC formally characterizes adenomas as pre-cancerous polyps ("Stage 0") by a T-stage of "Tis", where the "is" stands for carcinoma in situ. Tis adenomas are characterized by a polyp sitting in the large intestinal mucosa, with no invasion of the intestinal wall. (Table 1.)

In some embodiments, methods are provided for analyzing the clinical stage of lesions in the colon of a subject. As used herein, "stage" or "staging" refers to one or more clinical classification systems used to describe the progression and severity of cancerous or pre-cancerous lesions in the colon. Colorectal tumor stage describes the location and level of tumor invasion into the intestinal wall, regional lymph nodes, and adjacent tissues.

A nonexclusive example of a tumor staging system used in connection with embodiments of the present disclosure is the TNM system (Gunderson, L. L. et al., *J Clin Oncol* 2010, 28, (2), 264-71.; Greene, F. L., *Bull Am Coll Surg* 2002, 87, (7), 13-5) (Table 1). In the TNM system, stages 1 and 2 have T-stages of T1 or T2 and T3 or T4, respectively, with no invasion of lymph nodes or metastasis (N0 M0). Stage 1 lesions have passed into the submucosa and possibly the muscle layer. Stage 2 lesions have invaded the serosa and may have grown through the intestinal wall but has not invaded any nearby lymph nodes. Stage 3 lesions are very complex with three sub classifications, but can broadly be characterized by having any T-stage and the invasion of some or many nearby lymph nodes. Stage 4, constituting malignant, metastatic colon cancer, can have any T or any N classification but has metastasized other organs, most commonly the liver. (Table 1.)

Those skilled in the art will recognize alternative staging systems useful in connection with the presently disclosed methods. Examples of other staging systems include the Duke's classification system (Dukes, C. E., *Journal of Pathological Bacteriology* 1932, 35:323), and the Astler-Coller classification system (Astler V. B. and Coller F. A., *Ann Surg* 1954, 139:846).

In some embodiments, methods are provided for analyzing the clinical grade of lesions in the colon of a subject. As used herein, "tumor grade" refers to a histological assessment that describes the degree to which the tumor cells have differentiated into normal colon tissue cells. Current tumor grade classifications are part of the TNM guidelines of colon cancer classification and range from G1 to G4. Cells rated G1 histologically look the most like healthy colon tissue cells. G2 rated cells are moderately differentiated, G3 rated cells are poorly differentiated, and G4 cells are undifferentiated. Higher-grade cells tend to grow more rapidly and can influence the method of cancer treatment. In some embodiments, the protein biomarkers and methods provided herein can be used to assess the level of cellular differentiation (tumor grade) and influence patient treatment strategies.

In one particular aspect, provided herein are methods for identifying a subject with polyp formation in the colon, the method comprising (a) assaying a biosample from the subject for one or a plurality of protein biomarkers; (b) determining the level of one or a plurality of the protein biomarkers in the biosample; and (c) identifying the subject as having polyp formation in the colon when the level of one or a plurality of the protein biomarkers is different than a level detected in a subject without polyp formation in the colon. Suitable protein biomarkers include epidermal growth factor receptor, leucine-rich alpha-2 glycoprotein, inter-alpha trypsin inhibitor heavy chain 3, inter-alpha trypsin inhibitor heavy chain 4, dipeptidyl peptidase 4, peptidase inhibitor 16, coagulation factor V, C-reactive protein, Rho-GDP dissociation inhibitor 1 isoform A, hemopexin, extracellular superoxide dismutase[Cu—Zn], thrombospondin-4, collagen alpha-1(l) chain, cadherin-2, vitronectin, maltase glucoamylase, isocitrate dehydrogenase, pyruvate kinase m2, vitamin D binding protein, CD44 antigen, CEACAM5, cathespin B, serum amyloid P, fetuin B, matrilysin, complement factor 1, heparin cofactor 2, sulfhydryl oxidase 1, thrombospondin 4, and receptor-type tyrosine-protein phosphastase mu.

Non-Exclusive NCBI Accession Data for Certain Exemplary Biomarkers Presented Herein In addition, epidermal growth factor receptor (EGFR) is provided as a biomarker useful to practice the present methods. EGFR is implicated in poor tumor prognosis (Lieto, E. et al., *Ann Surg Oncol* 2008, 15, (1), 69-79).

Certain enzymes implicated in the inflammation response are provided as biomarkers useful to practice the present methods. Alpha-1-antitrypsin 1-5 is a protease inhibitor that helps protect tissues from the release of inflammatory enzymes and often rises in concentration during acute inflammation reactions (Foell, D. et al., *Gut* 2009, 58, (6), 859-68). This protein has been identified at increased levels in stool samples and in serum from human colon cancer patients (Foell, D. et al., *Gut* 2009, 58, (6), 859-68; Ward, D. G. et al., *Br J Cancer* 2006, 94, (12), 1898-905). Leucine-rich alpha-2-glycoprotein (LRG1) and fetuin-B are thought to play a role in acute phase response and inflammation (Hsu, S. J. et al., *Genome* 2004, 47, (5), 931-46.; Shirai, R. et al. *Biochem Biophys Res Commun* 2009, 382, (4), 776-9). LRG1 has shown upregulation in multiple mouse studies and has been shown to be upregulated in the plasma of human colon cancer patients (Hung, K. E. et al., *Cancer Prev Res (Phila)* 2009, 2, (3), 224-33.; Chong, P. K. et al., *J Proteome Res* 2010, 9, (7), 3671-9; Shirai, R. et al. *Biochem Biophys Res Commun* 2009, 382, (4), 776-9); Ladd, J. J. et al., *Cancer Prev Res (Phila)* 2012, 5, (4), 655-64).

LRG1 is an acute phase response protein that is upregulated in the blood of humans and murine models of colon cancer (Ivancic, M. M. et al., *J Proteome Res* 2013, 12, (9), 4152-66; Chong, P. K. et al., *J Proteome Res* 2010, 9, (7), 3671-9; Ladd, J. J. et al., *Cancer Prev Res (Phila)* 2012, 5, (4), 655-64; Ivancic, M. M. et al., *Cancer Prev Res* 2014, 55,

| Protein Name | Protein Symbol | NCBI RefSeq Number (Mouse/Rat/Human) |
|---|---|---|
| epidermal growth factor receptor | EGFR | NP_997538.1/NP_113695/NP_958439 |
| leucine-rich alpha-2-glycoprotein | LRG1 | NP_084072/NP_001009717/NP_443204 |
| inter-alpha-trypsin inhibitor heavy | ITIH3 | NP_032433/NP_059047/NP_002208 |
| inter alpha-trypsin inhibitor, heavy | ITIH4 | NP_061216/NP_062242/NP_001159921 |
| Dipeptidyl peptidase-4 | DPP4 | NP_034204/NP_036921/NP_001926 |
| Peptidase inhibitor 16 | PI16 | NP_076223/NP_001163952/NP_699201 |
| coagulation factor V | F5 | NP_032002.1/NP_001041343/NP_000121 |
| C-reactive protein | CRP | NP_031794.3/NP_058792/NP_000558 |
| rho GDP-dissociation inhibitor 1 | ARHGDIA | NP_598557.3/NP_001007006/NP_004300 |
| hemopexin | HPX | NP_059067.2/NP_445770/NP_000604 |
| Extracellular superoxide dismutase [Cu—Zn] | SOD3 | NP_035565/NP_037012/NP 003093 |
| Thrombospondin-4 | THBS4 | NP_035712/NP_058829/NP_003239 |
| collagen alpha-1(I) chain | COL1A1 | NP_031768.2/NP_445756/NP_000079 |
| Cadherin-2 | CDH2 | NP_031690/NP_112623/NP_001783 |
| vitronectin | VTN | NP_035837/NP_062029/NP_000629 |

In another aspect, Inter-alpha-trypsin inhibitors, heavy chain H3 (ITIH3) and heavy chain 4, isoform 1 (ITIH4) are provided as biomarkers useful to practice the present methods. The inter-alpha trypsin inhibitors are involved in the covalent binding and stabilization of hyaluronic acid on the extracellular matrix (Chen, L. et al., *J Biol Chem* 1994, 269, (45), 28282-7). Hyaluronan is a large epithelial glycosaminoglycan complex known to increase in size with the growth of colonic polyps and tumors (Misra, S. et al., *Connect Tissue Res* 2008, 49, (3), 219-24). In addition, ITIH3 has previously been identified as upregulated in the plasma of human gastric cancer patients and has a predicted role in the prevention of metastasis and tumor invasion activities in colon cancer (Misra, S. et al., *Connect Tissue Res* 2008, 49, (3), 219-24; Chong, P. K. et al., *J Proteome Res* 2010, 9, (7), 3671-9).

7(11); 1160-9). Studies have shown that this protein is also upregulated in the serum of patients with ulcerative colitis, suggesting that LRG1 may also be a systemic indicator of intestinal disease (Serada, S. et al., *Inflamm Bowel Dis* 2012, 18, (11), 2169-79). One study showed that LRG1 promotes endothelial cell formation via signaling by the TGF-β pathway through interactions with ALK1-SMAD 1, 5, and 8, thus inducing an angiogenic state (Wang, X. et al., *Nature* 2013, 499, (7458), 306-11). Angiogenesis, one of the fundamental attributes of tumor invasion and metastasis, can be triggered very early in tumor formation (Hanahan, D. et al., *Cell* 2011, 144, (5), 646-74). Other studies have shown that circulating levels of LRG1 in blood plasma may be useful to diagnose colorectal cancer and identify regional tumor localization within the colon, rectosigmoid junction, and the rectum (Surinova, S. et al., *EMBO Mol Med* 2015, 7, 1153-1165; Surinova, S. et al., *EMBO Mol Med* 2015, 7, 1166-1178).

Maltase-glucoamylase (MGAM) is also provided as one of the biomarkers useful to practice the present methods. MGAM is an intestinal protein necessary for catalyzing the final steps in starch catabolism (Real, F. X. et al., *Int J Cancer* 1992, 51, (2), 173-81; Young, G. P. et al., *J Gastroenterol Hepatol* 1992, 7, (4), 347-54). An immunohistochemical study that compared MGAM expression on human colonic epithelium to normal epithelium showed reduced expression of this enzyme (Real, F. X. et al., *Int J Cancer* 1992, 51, (2), 173-81; Young, G. P. et al., *J Gastroenterol Hepatol* 1992, 7, (4), 347-54). MGAM, while quite specific to the intestine, is a very large protein (1827 amino acids) with a single transmembrane pass and a very small domain inside the cell (Sim, L. et al., *J Mol Biol* 2008, 375, (3), 782-92). The brush border activity of the enzyme is localized completely external to the cell. Thus, this protein may be released into the blood.

In addition, Collagen-1 type 1(I) alpha 1 (COL1A1) is provided as one of the biomarkers useful to practice the present methods. Downregulated COL1A1 has been previously reported in cancer studies, and it is thought to play a role as part of oncogenic transformation (Sengupta, P. et al. *J Biol Chem* 2005, 280, (22), 21004-14). Among its many functions, COL1A1 is a positive regulator of the canonical WNT signaling pathway, the pathway that is constitutively active in early stages of colon cancer (Medici, D. et al., *Matrix Biol* 2010, 29, (3), 161-5). COL1A1 and LRP5 expression are commonly linked in bone matrix formation and are misregulated in bone disease. LRP5 is a co-receptor with the frizzled receptor in the WNT signaling pathway.

Coagulation factor V (F5) is also provided as one of the biomarkers useful to practice the present methods. F5 is a cofactor for activated coagulation factor X (Xa) which assists in cleaving prothrombin to form an active thrombin protein which is vital for blood clotting (Davie, E. W. et al., *Biochemistry* 1991, 30, (43), 10363-70). Perturbation in hemostasis is a commonly observed side effect of cancer, with venous thromboembolism as a documented complication in colon cancer patients (Falanga, A. et al., *J Thromb Haemost* 2013, 11, (2), 223-33; Alcalay, A. et al., *J Clin Oncol* 2006, 24, (7), 1112-8). Coagulants such as fibrinogen, F5, and other coagulation factors have increased levels in colon cancer patients (Paspatis, G. A. et al., *Pathophysiol Haemost Thromb* 2002, 32, (1), 2-7; Vossen, C. Y. et al., *J Clin Oncol* 2011, 29, (13), 1722-7). In addition, F5 is most known for its association with the Factor V Leiden coagulation disease. Factor V Leiden is caused by a single nucleotide polymorphism (SNP) involving an R506Q mutation. This mutation reduces the ability of the activated protein C anticoagulant protein from binding F5. Normal interactions between activated protein C and F5 lead to the degradation of F5. However, in the absence of this interaction, F5 levels increase and cause excessive coagulation. Patients homozygous for the factor V Leiden mutation show a nearly 6-fold increased risk for colorectal cancer (Vossen, C. Y. et al., *J Clin Oncol* 2011, 29, (13), 1722-7). A recent biomarker study has indicated that F5 may be a blood plasma marker to distinguish localized versus metastatic colorectal cancers (Surinova, S. et al., *EMBO Mol Med* 2015, 7, 1153-1165).

In another aspect, Vitronectin (VTN) is provided as one of the biomarkers useful to practice the present methods. Vitronectin has been shown to promote cell adhesion and spreading, and is indicated in tumor malignancy (Felding-Habermann, B. et al., *Curr Opin Cell Biol* 1993, 5, (5), 864-8). This protein also inhibits the membrane-damaging effect of some proteins involved in the terminal cytolytic complement pathway through binding to several serpin serine protease inhibitors (Milis, L.; Morris, C. A. et al., *Clin Exp Immunol* 1993, 92, (1), 114-9). Large and consistent upregulation of several complement factors in murine models, including complement factor B, complement C5, and complement C4-B, suggests that vitronectin could partially mitigate the damaging effects of these upregulated proteins. Vitronectin may also be a marker for regional tumor localization within the colon, rectosigmoid junction and the rectum (Surinova, S. et al., *EMBO Mol Med* 2015, 7, 1153-1165).

Additionally, Cathepsins B and E are provided as biomarkers useful to practice the present methods. Cathepsin E is a gastric aspartyl protease that is found at highest levels on the mucosal producing epithelial cells of the stomach (Caruso, M. et al., *Virchows Arch* 2009, 454, (3), 291-302). It is commonly upregulated in gastric cancers. Cathepsin B has been identified in elevated amounts on the surface of colon tumor cells, in plasma, and has previously been linked to negative colon cancer prognosis (Hung, K. E. et al., *Cancer Prev Res (Phila)* 2009, 2, (3), 224-33; Cavallo-Medved, D. et al., *Neoplasia* 2003, 5, (6), 507-19). Alpha-2-macroglobulin, a protease inhibitor (and a biomarker useful to practice the present methods), has been shown to interact with these two cathepsins (Shibata, M. et al., *Eur J Biochem* 2003, 270, (6), 1189-98.; Mason, R. W., *Arch Biochem Biophys* 1989, 273, (2), 367-74).

Certain aspects of the invention provide assaying the biosample for protein biomarkers wherein the assaying step comprises extracting a desired peptide from a biosample and separating the extracted peptide mixture. In particular embodiments, the protein is extracted from a biological material of interest and the isolated proteins are enzymatically digested with a protease to generate peptide fragments. The complex peptide mixture is chromatographically separated using reversed-phase chromatography. In a particular embodiment the reversed phase chromatography is high pH reversed phase chromatography. Alternatively, the complex peptide mixture is chromatographically separated using offline ion exchange chromatography or high pH reversed-phase chromatography. Furthermore, those of skill in the art will recognize that other extraction and separation techniques are suitable for practicing embodiments of the present methods.

In particular embodiments, a stable isotope labeled standard is spiked into the protein extract prior to an enzymatic digest. The reference standard can be used for relative or absolute quantification (Yocum, A. K. and Chinnaiyan, A. M., *Brief Funct Genomic Proteomic* 2009, 8, (2), 145-57). A common absolute quantification method is known as AQUA (standing for Absolute QUAntification). AQUA peptides are identical in sequence to the endogenous peptide with the exception of a heavy stable isotope amino acid spiked into a sample at a known concentration. Thus, the exact concentration of the endogenous peptide, when compared to the AQUA peptide, can be determined (Gerber, S. A. et al., *Proc Natl Acad Sci USA* 2003, 100, (12), 6940-5). When the exact concentration of stable isotope-labeled peptide is unknown, the peptide can be spiked into the sample at a known ratio and used for relative quantification. Reference standards can also be made as whole proteins or synthetic concatenated tryptic peptides in vivo using stable isotope labeled proteins (PSAQ) or concatemers (QconCAT), respectively (Kaiser, S. E. et al., *Nat Methods* 2011, 8, (8), 691-6, 130).

Particular embodiments disclosed herein employ reversed-phase chromatography that is optimized to resolve low-level endogenous peptides and optimize peak shapes for quantitative peak integration. For example, in certain embodiments the HPLC system is an Eksigent Nano 2D LC equipped with a Nanoflex cHiPLC system. The Nanoflex system is optionally equipped with C18 microfluidic chips that are used for trapping and chromatographically eluting peptides in a reversed-phase gradient. In addition, the Nanoflex system is optionally equipped with a column heater to optimize the effect of temperature on peak resolution.

In particular embodiments, the methods provided herein use optimized chromatography gradient lengths to identify low abundance endogenous peptides by shifting the number of co-eluting species and reducing localized sample complexity. Accordingly, in a particular embodiment the methods herein provide an effective gradient length of 90-minutes for chromatographic separations.

To achieve high specificity, the peptide amino acid sequence of the reference standard is unique to the protein biomarker (Lange, V. et al., *Mol Syst Biol* 2008, 4, 222). Peptide length is kept between approximately 6-20 amino acids to achieve good chromatographic peak shape, proper ionization, and optimal fragmentation (Picotti, P. et al., *Nature* 2013, 494, (7436), 266-70; Elias, J. E. et al., *Nat Methods* 2005, 2, (9), 667-75; Kirkpatrick, D. S. et al., *Methods* 2005, 35, (3), 265-73). In certain embodiments, peptide collision energies are optimized to provide the most intense fragment ions, and a scheduling method is implemented so that only a limited number of transitions are analyzed over a given cycle time. Those skilled in the art will recognize that scheduling has the capacity to increase dwell times (length of time a transition is analyzed) in order to maximize signal for a particular ion. In one embodiment, a scheduling window of 5-7 minutes is chosen resulting in dwell times of at least 20 ms or more within a 1.5-second cycle time for peptides used in the present methods. Alternatively, scheduling windows of different lengths are also contemplated.

The use of a stable isotope as reference standard provides the ability to directly compare two or more samples within the same analysis, thus eliminating problems associated with the run-to-run variability observed in label-free methods. These standards, unique to the target protein biomarker, contain a heavy stable isotope labeled amino acid to differentiate it from the target endogenous peptide biomarker. Further, these reference standards also have the ability to assist in identifying the correct peptide isomer of interest when multiple similar peptide sequences exist in a complex protein digest, thus contributing to the specificity of the assay (Banack, S. A. et al., *Toxicon* 2010, 56, (6), 868-79).

In certain embodiments, the levels of the one or plurality of the protein biomarkers in the biosample are determined using mass spectrometry. In particular embodiments, the levels of protein biomarkers are determined using selected reaction monitoring mass spectrometry (SRM-MS). In other embodiments, the levels of the one or plurality of the protein biomarkers in the biosample are determined using other quantitative mass spectrometry techniques, including, without limitation, spectral counting, isobaric mass tagging, or ion mobility mass spectrometry.

In further embodiments, the absolute concentration of the one or a plurality of protein biomarkers is determined. In some embodiments, absolute concentration of the one or a plurality of protein biomarkers is determined using SRM-MS in combination with the AQUA method.

In other embodiments, the determining step of the claimed methods employs alternatives to mass spectrometry. For example, in certain embodiments, a level of protein biomarker is determined using routine immunoassay techniques known to the art. Such immunoassay techniques include, without limitation, Enzyme-Linked immunosorbent assay (ELISA), protein arrays, Western blotting, flow cytometry cell sorting, immunohistochemistry, immunocytochemistry, or immunocytometry. In some embodiments of the presently disclosed methods, the determining step comprises variations on routine immunoassay techniques, including, without limitation, microfluidic chip-based ELISAs or Westerns.

In still other embodiments, the determining step of the presently disclosed methods employ quantification by electrophoresis. For example, in some embodiments, the determining step comprises, without limitation, one- or two-dimensional electrophoresis, or capillary electrophoresis. Those skilled in the art will recognize still further quantitative electrophoresis methods suitable for practicing the present disclosure.

In still further embodiments, the levels of the one or plurality of the protein biomarkers in the biosample are determined by traditional protein quantification techniques. For example, in certain embodiments the levels of one or a plurality of biomarkers are determined using, without limitation, UV-VIS spectroscopy, Bradford, BCA, or Lowry Assays. In some embodiments, determining the levels of one or a plurality of biomarkers is accomplished after the biomarker is purified from the biosample.

In other embodiments, the determining step of the present disclosure comprises subjected the biosample to one or more chromatographic quantitation techniques. Examples of liquid chromatography methods include cation exchange, anion exchange, reversed-phase, and size exclusion chromatography. Those skilled in the art recognize that the area under a chromatographic peak is representative of the relative amount of a biomarker present in a biosample.

A subject is identified as having polyp formation in the colon when the expression level of one or a plurality of the protein biomarkers is different than an expression level detected in a subject without polyp formation in the colon. In certain embodiments, levels of a subject without a polyp formation in the colon are derived from a database of protein markers from previously tested subjects who did not have polyp formation or colon cancer. Alternatively, the levels of differentially expressed biomarkers in the biosample of a subject are measured relative to a biosample from a subject without cancer or precancer.

"Differentially expressed" as used herein refers to a comparison between a biomarker determined in two or more biosamples, or between a biomarker determined in a biosample and a biomarker reference standard, wherein expression levels of a measured biomarker are different between the compared biosamples, or between the biosample and the reference standard. In some embodiments, differential expression comprises an increase in a compared biomarker level. In other embodiments, differential expression comprises a decrease in a compared biomarker level. In still other embodiments, differential expression comprises a change in a compared biomarker over time. In yet other embodiments, differential expression comprises a change in a compared biomarker between different stages of polyps or tumors present in the colon of a subject. In still other embodiments, differential expression comprises a change in a compared biomarker during treatment of a lesion present in the colon of a subject.

In embodiments, differential expression of one or a plurality of biomarkers of the present disclosure is used to determine the presence, or stage, of lesions in the colon of a subject. In particular embodiments, differential expression comprises a deviation in the level of one or a plurality of biomarkers in a biosample from a reference biosample, or from a biomarker reference standard. In some embodiments, a deviation in one or a plurality of biomarkers of about 10%, about 20%, about 30%, about 40% about 50%, about 60%, about 70%, about 80%, or about 90%, from the corresponding reference amount, is indicative of the presence or stage of a lesion in the colon of a subject. In alternative embodiments, a deviation in one or a plurality of biomarkers of about 2-fold, about 4-fold, about 8-fold, about 10-fold, about 20-fold, about 40-fold, about 80-fold, or about 100-fold, from the corresponding reference amount, is indicative of the presence or stage of a lesion in the colon of a subject.

Methods are provided to determine the level of one or a plurality of protein biomarkers in a biosample collected from a human, non-human primate, mouse, rat, dog, cat, horse, or cow. As used herein, a "biosample" is comprised of biologic material isolated from a subject and includes, without limitation, blood, serum, tissue, plasma or blood cells.

Notably, the biomarkers useful for the presently disclosed methods comprise a bodily response at times occurring distant from the tumor or adenoma or polyp cells. Major examples include hepatically produced acute-phase and inflammatory response proteins. Acute phase, inflammatory and immune responses have been identified as a common response to tumor presence (Mantovani, A. et al., Nature 2008, 454, (7203), 436-44; 215), and cell adhesion represents an important function related to cancer metastasis. Hyaluronan-binding proteins such as the inter-alpha-trypsin inhibitors provide vital transport of this glycosaminoglycan to growing tumors. These are just a few examples presented here relating to the systemic response to cancer. Accordingly, one of skill in the art will recognize that the biosamples of the present invention are derived from both tumor and non-tumor cells. Furthermore, one of skill in the art will recognize that the biosamples of the present invention are optionally isolated from a broad range of materials, including without limitation blood, serum, plasma, tissue, ascites fluid, urine, and fecal matter.

Embodiments of the present disclosure provide a biosample-based test for colorectal cancer that has the sensitivity and specificity to provide an alternative to routine screening using colonoscopy as a primary diagnostic mechanism. Embodiments of the method of screening use a high-throughput targeted mass spectrometry procedure, which multiplexes many protein markers into a single quantitative screening assay.

In particular embodiments, the biosample-based test for colorectal cancer using SRM-MS advantageously provides a reduced cost per biomarker, potential for increased throughput in a biomarker panel analysis, and increased sensitivity and specificity.

Certain embodiments provide methods for routine screening of populations for the presence of pre-cancerous or cancerous conditions. These methods include routine collection of blood and other materials useful for diagnostic purposes. In addition, in certain embodiments the biosample of the present invention is obtained during, or coincident to, a colonoscopy or polypectomy procedure. In still further embodiments, the biosample of embodiments of the present invention is obtained periodically following colonoscopy or polypectomy. In still further embodiments, the biosample is obtained prior to colonoscopy and levels of protein biomarkers determined to identify patients requiring colonoscopy.

Embodiments of the present methods are useful for routine screening of patient populations. The present methods are particularly advantageous in cases where compliance of eligible subjects with existing screening recommendations is low, primarily because existing screening methods can be invasive, expensive, and unavailable in rural areas. In addition, embodiments of the present methods are useful for screening of patient populations that do not present elevated risk factors for colorectal cancer (e.g. family history), or would not otherwise be indicated for currently existing screening or diagnostic methods.

In still other embodiments, methods are provided for identifying individuals who would benefit from further clinical assessment or treatment, including but not limited to, further assessment or treatment by colonoscopy or polypectomy procedures. In other embodiments, post-surgical or post-polypectomy patient monitoring is provided. In still other embodiments, the present methods are useful for monitoring responsiveness of a patient to chemopreventative or chemotherapeutic agents.

In addition, methods are provided that are capable of enhancing the diagnostic and prognostic utility of currently existing colorectal screening, diagnostic, prognostic and treatment techniques. Accordingly, certain embodiments disclosed here are useful in combination with other techniques known to the art, including colonoscopy, CT scan, or Fecal Occult Blood Test.

In a further aspect, the disclosure is directed to a kit for the determination of colorectal lesions in a subject. The kit includes one or more detecting reagents for detecting the one or a plurality of biomarkers of the present disclosure, and optionally includes a set of standard values for one or a plurality of protein biomarkers associated with the presence or absence of cancerous or pre-cancerous colorectal lesions.

Moreover, the present disclosure relates to a kit adapted for carrying out methods of the present disclosure referred to above comprising; a) means for determining the amounts of the one or a plurality of biomarkers in a biosample of the present disclosure, b) means for comparing the amounts determined in step a) with reference amounts, whereby the presence or stage of lesions present in the colon of a subject are to be determined. In some embodiments, the kit comprises instructions for carrying out methods of the present disclosure.

The term "kit" as used herein refers to a collection of the aforementioned means, suitably, provided separately or within a single container. The container, also suitably, comprises instructions for carrying out methods of the present disclosure.

The present disclosure also relates to the use of a kit or kits as cited beforehand, for: identifying a subject with cancerous or pre-cancerous lesions in the colon; or for identifying a colorectal carcinoma as stage 1, stage 2, stage 3, or stage 4 carcinoma; or for determining and administering a course of treatment to a subject identified as having polyp formation in the colon; or for screening individuals to determine a need for a colonoscopy.

The invention will be further described in the following examples, which do not limit the scope of the invention described in the claims.

The examples that follow are illustrative of specific embodiments of the invention and various uses thereof.

They are set forth for explanatory purposes only and are not to be taken as limiting the invention.

EXAMPLES

Example 1: $Apc^{Pirc/+}$ Rat Microarray and Longitudinal Analysis

Animal Breeding and Maintenance.

Only male rats were utilized for the microarray and proteomics studies to eliminate potential confounding by estrus cycling in female rats. A 12:12 hour light:dark cycle was maintained throughout the experiments, and rats were all dissected within a four-hour window to control for any variation due to circadian cycles. $F_1$ generation (ACIxF344)-$Apc^{Pirc/+}$ rats were generated by breeding female ACI $Apc^{+/+}$ rats (Harlan) to male F344N/Tac coisogenic $Apc^{Pirc/+}$ (Pirc) rats (developed in the laboratory of WFD and now commercially available through Taconic) (Amos-Landgraf, J. M. et al., Proc Natl Acad Sci USA 2007, 104, (10), 4036-41). These "$F_1$-Pirc" rats show an increased tumor multiplicity and decreased time to tumor emergence compared to the standard coisogenic F344N/Tac-Pirc rat. One group of 97-day old $F_1$-Pirc rats was used for the microarray study. An additional two groups, an $F_1$-Pirc and a (ACI X F344) $F_1$ $Apc^{+/+}$ "$F_1$-wildtype" cohorts, were followed longitudinally from 60 to 135 days of age for the proteomics study.

The Microarray Rat Cohort.

The microarray experiments follow the nomenclature, descriptions, and data sharing recommended by the MIAME Guidelines (Brazma, A. et al., Nat Genet 2001, 29, (4), 365-71). Data have been deposited in NCBI's Gene Expression Omnibus (Edgar, R. et al., Nucleic Acids Res 2002, 30, (1), 207-10) and are accessible through GEO Series accession number GSE54035. To measure the levels of transcripts that were differentially expressed in tumors, RNA was isolated from 10 colonic tumor samples and 4 matched normal tissue samples from four $F_1$-Pirc rats. Tumor samples were obtained by harvesting one-quarter of the tumor. For the collection of normal intestinal tissue, a scalpel blade was used to gently scrape the luminal surface of the distal colon. A minimum 2 mm barrier surrounding any tumor was required for normal tissue collection.

Total RNA (100 ng) was labeled with a Low Input Quick Amp kit with Cy3 dye (Agilent Technologies) according to the manufacturer's instructions. RNA collected from normal tissue from a cohort of rats was labeled with Cy5 dye. Samples were evenly distributed and hybridized to Agilent 4×44 k Whole Genome microarrays. Following incubation, arrays were scanned on an Agilent High-Resolution Microarray Scanner at 3 μm resolution with a 20 bit data format. Files were extracted using Agilent Feature Extraction version 10.7. Data were then imported into Genome Suite software for analysis (Partek). A list of genes differentially expressed between normal colonic tissue and tumor tissue was generated using the criterion of differential expression equal to or greater than 5-fold with a false discovery rate (FDR) equal to or less than 5%.

The Longitudinal Rat Cohorts.

14 $F_1$-Pirc and 10 $F_1$-wildtype rats underwent endoscopy at 60 and 90 days of age to determine the multiplicity and growth pattern of colonic tumors in vivo. Rats were then sacrificed at 135 days to determine total intestinal tumor multiplicity. Blood was collected from each animal at 60, 90 and 135 days of age. For endoscopy, the animal was anesthetized with 3% isoflurane and placed on a sterile surgical field, ventral side down. The colon was flushed with warm saline to remove any fecal material and to provide lubrication. Tumors were examined at each of the two endoscopy visits and any tumor that was seen at both visits was given one of three scores: growing, static, or regressing. A consensus score was generated for each tumor based on agreement between at least two of three blinded observers. After sacrifice at 135 days of age, formalin-fixed tumors in the small intestine and colon were counted at 10× magnification on an Olympus dissecting microscope.

Example 2: Liquid Chromatography Selected Reaction Monitoring Mass Spectrometry Protein Candidate Selection.

Serum proteins for targeted mass spectrometry analysis were chosen using two strategies. First, protein candidates were chosen corresponding to transcripts up-regulated in colon tumors in the microarray study. These candidates were nominated using three criteria: those with RNA levels up-regulated at least 5-fold in colonic neoplasms compared to normal tissue after filtering to a 0.05 false discovery rate; proteins predicted or known to be secreted (Edgar, R. et al., Nucleic Acids Res 2002, 30, (1), 207-10); and proteins with potential biological significance to colon cancer (Vogelstein, B. et al., Science 2013, 339, (6127), 1546-58). The second strategy of candidate selection used quantitative proteomic data from the serum of the $Apc^{Min/+}$ mouse compared to wildtype, as previously described (Ivancic, M. M. et al., J Proteome Res 2013, 12, (9), 4152-66). Two protein candidates that arose in both detection strategies were chosen, to increase the chance of identifying differentially expressed blood proteins.

Synthetic Peptides for Targeted Analysis.

Peptides were designed and synthesized using a three tiered selection process. (FIG. 2.) Tier 1 selection criteria included sequence uniqueness (Altschul, S. F. et al., J Mol Biol 1990, 215, (3), 403-10), length, relative hydrophobicity (Yang, F. et al., Expert Rev Proteomics 2012, 9, (2), 129-34), and absence of known post-translational modification (unless that modification is targeted for analysis).

Tier 2 selection criteria included empirical mass spectrometry data indicating suitability of proteotypic peptide sequence, including untargeted data collected from in-house shotgun proteomics studies, and data found in open-source mass spectrometry repositories such as PeptideAtlas, which stores proteomic data from yeast, mice, and humans (Deutsch, E. W. et al., EMBO Rep 2008, 9, (5), 429-34). Peptides routinely identified within these databases have a greater chance of being identified in a targeted analysis. These mass spectrometry data resources can also identify proteins with peptides that are prone to missed cleavage during enzymatic digestion. Tier 2 criteria also comprised predictive algorithms to identify peptides that are good for targeted SRM analyses on triple quadrupole instruments. For example, SRMAtlas uses the predictive algorithm PABST to assist in selecting proteotypic peptides for SRM analyses. PABST uses both theoretical and empirical data to score peptides for their usability in an SRM-MS experiment for yeast, mice, or humans.

Tier 3 criteria are relevant to designing peptides that have cross-species significance. The peptides targeted must be unique within the proteome of the experimental model species, but must also be identical to the orthologous protein in humans, thus facilitating extrapolation of animal data to methods and reagents useful in humans.

In a first iteration, 61 peptides were selected from rat transcriptome candidates (Example 3, infra). Of the 61 tested, 9 peptides satisfied additional screening criteria. In a second round of screening, 30 peptides were selected and tested and 27 satisfied additional screening criteria. A complete list of peptides is provided in Table 2.

TABLE 2

| Peptide Number | Peptide Sequence (*indicates 13C15N amino acid in reference standard unless notes otherwise) | Name | Gene symbol | Percent Purity of standard | Sequence Homology | Discovery study (rat and/or mouse) | Endogenous Observed in SRM assay | Dominant Charge State | Collision Energy | Top Peptide ions monitored (Qtrap 5500) | Peptide Ion quantified |
|---|---|---|---|---|---|---|---|---|---|---|---|
| 1 | TSWGLENEALV*R | Interlukin 1 receptor-like 1 | IL1RL1 | 95.6 | Rat | Transcriptome (Rat) | No | +2 | 38.2 | y8, y9, y10, b8 | N/A |
| 2 | FTHTENGTNYIV*TATR | | | 100 | Rat | | No | +3 | 26.0 | y6, b8, b9, b10 | N/A |
| 3 | SFTV*EEK | | | 97.6 | Mouse and rat | | No | +2 | 19.7 | y4, y5, b2, b3 | N/A |
| 4 | AHMSYLFICK* | | | 96.1 | Rat | | No | +2 | 30.7 | y7, y8, b6, b7 | N/A |
| 5 | FLVDQIV*K | Matrix Metalloproteinase-7 (Matrilysin) | MMP7 | 100 | Rat | Transcriptome (Rat) | Yes | +2 | 23.2 | y6, y7, b7 | y6 |
| 6 | IVSYTTDLP*R | | | 96.1 | Rat | | No | +2 | 29.0 | y6, y7, y9 | N/A |
| 80 | DLPHTVD*R | | | 83 | Human | | No | +3 | 20.9 | y8, y9 y4, y5, b4 | Monitoring y5 |
| 7 | TYPFVGDK* | Matrix Metalloproteinase-10 | MMP10 | 99.5 | Mouse and Rat | Transcriptome (Rat) | No | +2 | 23.6 | y5, y6, y7 | N/A |
| 8 | TVTHTLK* | | | 91.3 | Rat | | No | +2 | 18.5 | y6, y7, b8 | N/A |
| 9 | QDHSTMCKAQQYL*EK | | | 99.1 | Rat | | No | +3 | 25.8 | y3, y4, y5, b5 | N/A |
| 10 | LDSNTEMMHKP*R | | | 99 | Rat | | No | +4 | 19.2 | y5, y6, y7, y8 | N/A |
| 11 | FLGLE<TGK* | | | 97.7 | Mouse MMP3/10 Rat | | No | +2 | 24.1 | y5, y7, y8 | N/A |
| 12 | IDAAV*FEK | | | 96.9 | Mouse and Rat | | Yes | +2 | 21.2 | y4, y5, y6, y7 | Too low to quantify |
| 13 | GSQFWAV*R | | | 99.9 | Mouse and Rat | | Yes | +2 | 22.9 | y4, y5, y6 | Too low to quantify |
| 14 | SNSWLL*C | | | 98.8 | Mouse and Rat | | Yes | +2 | 20.8 | b4, b5, b6 | b5 |
| 15 | DDAFFIGSTLATIASTV*YSK | CD44 antigen | CD44 | 100 | Rat | Transcriptome (Rat) | Yes | +2 | 28.9 | y7, y9, b5 | Too low to quantify |
| 16 | EPTETPDQFMTADET*R | | | 100 | Rat | | No | +2 | 49.0 | y8, y9, b5 | N/A |

TABLE 2-continued

| Peptide Number | Peptide Sequence (*indicates 13C15N amino acid in reference standard unless notes otherwise) | Gene symbol | Name | Percent Purity of standard | Sequence Homology | Discovery study (rat and/or mouse) | Endogenous Observed in SRM assay | Dominant Charge State | Collision Energy | Top Peptide ions monitored (Qtrap 5500) | Peptide Ion quantified |
|---|---|---|---|---|---|---|---|---|---|---|---|
| 17 | TQWMPIHSNPEVLLQTT*R | | | 100 | Rat | | No | +3 | 30.2 | y7, y8, b9 | N/A |
| 18 | STPEGYILHTDLPTSQP*TGDR | | | 100 | Rat | | Yes | +3 | 30.7 | y5, y8, y9 | Too low to quantify |
| 19 | KPSELNGEASK* | | | 90.7 | Mouse and Rat | | No | +3 | 19.1 | y4, y5, b4, b5 | N/A |
| 20 | NLQSVDMK* | | | 98.2 | Mouse and Rat | | Yes | +2 | 22.4 | y8, y9, y10, b5 | Too low to quantify |
| 21 | LVINSGNGTV*EDR | | | 86.1 | Rat | | No | +2 | 34.9 | y8, y9, y10, y11 | N/A |
| 73 | YGFIGHVVIP*R | | | 82 | Rat and human | | Yes | +3 | 22.8 | y4, y5, y6 | y4 |
| 22 | AFPAFVL*R | Wit1 | Wnt Inhibitory Factor 1 | 95 | Rat | Transcriptome (Rat) | Yes | +2 | 22.0 | y4, y5, y6 | y6 |
| 23 | LGTVPHK* | | | 100 | Mouse rat and human | | No | +2 | 17.2 | y4, b4, b5 | N/A |
| 24 | ASVVQVGFPCL*GK | | | 99.2 | Mouse rat and human | | No | +2 | 34.6 | y7, y8, y9 | N/A |
| 25 | YGASLMHAPRPAGAGL*ER | | | 100 | Mouse and rat | | No | +3 | 26.3 | y10, b9, b10 | N/A |
| 26 | TPQNAI*FFK | | | 100 | Mouse rat and human | | No | +2 | 26.1 | y5, y6, y7 | N/A |
| 27 | TCQAECP*GGCR | | | 95.2 | Mouse rat and human | | No | +2 | 35.3 | y5, y7, y8 | N/A |
| 28 | ADAGQPPEESLYLWI*DAHQAR | | | 100 poor peak shape | Mouse and rat | | No | +3 | 31.6 | y7, y8, y9 | N/A |
| 29 | LWSILPCLLLL*R | | | 97.6 | Mouse rat | | Yes | +2 | 38.4 | y7, y8, y10 | Too low to quantify |
| 30 | VVGGKPAEMGDYPWQVAI*K | CFI | Complement Factor I | 99.3 | Rat | Transcriptome | Yes | +3 | 28.2 | y7, y8, b11, b12 | y7 |

TABLE 2-continued

| Peptide Number | Peptide Sequence (*indicates $^{13}C^{15}N$ amino acid in reference standard unless notes otherwise) | Name | Gene symbol | Percent Purity of standard | Sequence Homology | Discovery study (rat and/or mouse) | Endogenous Observed in SRM assay | Dominant Charge State | Collision Energy | Top Peptide ions monitored (Qtrap 5500) | Peptide Ion quantified |
|---|---|---|---|---|---|---|---|---|---|---|---|
| 31 | LPYQCP*K | | | 96.3 | Rat and human | and Proteome | Yes | +2 | 21.6 | y4, y5, y6 | y8 |
| 32 | VFCQP*WQK | | | 99.9 | Rat | | Yes | +2 | 26.9 | y5, y6, y7 | y6 |
| 33 | GYPTYCHLK* | | | 98.8 | Rat | | Yes | +2 | 28.2 | y5, y6, y7 | y7 |
| 34 | SFECLHPEIK* | | | 99.6 | Mouse and rat | | Yes | +2 | 31.7 | y7, 78, b6 | b6 |
| 35 | FNIPVNHK* | | | 100 | Rat | | Yes | +3 | 17.1 | y3, y4 y5, b3 | y5 |
| 36 | INSTECLHVR* | | | 99.8 | Rat | | Yes | +3 | 30.8 | y6, y7, y8 | N/A |
| 37 | FNVSLIYGSTDTEGIVQV*K | | | 95.4 | Rat | | Yes | +2 | 28.5 | y8, y9 y10, y12 | N/A |
| 81 | VFSLQWGEV*K | | | 75 | Human | | Yes | +2 | 28.3 | y5, y6, y7, y8 | y5 |
| 38 | ISHELESSSSEV*N | Secreted Phosphoprotein-1 | SPP1 | 94.9 | Mouse and rat | Transcriptome | No | +2 | 36.2 | b6, b7, b9, b11 | N/A |
| 39 | SISTINVPHQY*SR | S100 calcium binding protein A9 | S100A9 | 100 | Rat | Transcriptome | Yes | +3 | 24.3 | y6, y7 y8, b7 | Too low to quantify |
| 40 | YGHPDTLNK* | | | 94.5 | Rat | | No | +3 | 17.9 | y4, y5, y6, b6 | N/A |
| 41 | LSTSWTEEDNVDNTL*FK | Follistatin | FST | 96.8 | Mouse rat and human | Transcriptome | Yes | +3 | 27.8 | y7, y8, y9, y10 | |
| 42 | ATCLL*GR | | | 100 | Mouse rat and human | | No | +2 | 18.3 | y4, y5, b4 | N/A |
| 43 | EECCST*GR | | | 100 | Mouse rat and human | | No | +2 | 24.2 | y5, y6, y7 | N/A |
| 44 | WMIFNGGAPNCIP*CK | | | 100 | Mouse rat and human | | No | +2 | 46.1 | y3, y9, y10, y11 | N/A |
| 45 | SIGLAYEGK* | | | 100 | Mouse rat and human | | No | +2 | 22.5 | y4, y5, y6, y7 | N/A |

TABLE 2-continued

| Peptide Number | Peptide Sequence (*indicates $^{13}C^{15}N$ amino acid in reference standard unless notes otherwise) | Name | Gene symbol | Percent Purity of standard | Sequence Homology | Discovery study (rat and/or mouse) | Endogenous Observed in SRM assay | Dominant Charge State | Collision Energy | Top Peptide ions monitored (Qtrap 5500) | Peptide Ion quantified |
|---|---|---|---|---|---|---|---|---|---|---|---|
| 46 | EAACSSGVLLEV*K | | | 95.1 | Mouse rat and human | | No | +2 | 34.6 | y7, y8, y9 | N/A |
| 47 | CSLCDELCPDSK* | | | 100 | Mouse rat and human | | No | +2 | 38.0 | y7, y8, y9 | N/A |
| 48 | SCEDIQCGGGK* | | | 100 | Mouse and rat | | No | +2 | 30.3 | y7, y8, y9 | N/A |
| 49 | EACLDPEAPMV*QK | Chemokine (C-X-C motif) ligand 1 | Cxcl1 | 99.2 | Rat | Transcriptome | No | +2 | 34.6 | y6, y9, y10 | N/A |
| 50 | LDQNQV*R | Chemokine (C-C motif) ligand 2 | Ccl2 | 100 | Rat | Transcriptome | No | +2 | 20.6 | y4, y5, y6, b5 | N/A |
| 51 | MI*PMSR | | | 100 | Mouse and rat | | Yes | +2 | 16.7 | y3, y4, y5 | Too low to quantify |
| 52 | TLFLLALLGGVSGL*R | Leucine-Rich alpha-2-glycoprotein | Lrg1 | 95.6 | Rat | Transcriptome and Proteome | Yes | +2 | 39.4 | y10, y11, y12, b9 | Too low to quantify |
| 53 | SSAALNTLVL*R | | | 97.7 | Rat | | Yes | +2 | 28.4 | y6, y7, y8, y9 | y6 |
| 54 | LLDVAELGT*L | | | 98.2 | Rat | | No | +1 | 55.2 | b6, b7, b8 | N/A |
| 55 | SLPPGL*FR | | | 99.4 | Rat | | Yes | +2 | 21.0 | y4, y5, y6 | Too low to quantify |
| 56 | DLVDL*CR | | | 100 | Rat | | No | +2 | 21.1 | y4, y5, b4 | N/A |
| 57 | LHL*EGNR | | | 96.1 | Mouse and rat | | No | +2 | 19.7 | y4, y5, y6, b4 | N/A |
| 58 | ENQL*QEASAR | | | 95.8 | Rat | | No | +2 | 26.4 | y6, y7, y8, b5 | N/A |
| 76 | VAAGAFQGL*R (13C labeled only) | | | 83 | Human | | Yes | +2 | 26.7 | y5, y7, y8, y9 | y8 |
| 59 | NLYLSCV*MK | Interleukin-1 beta | Il1b | 99 | Mouse and rat | Transcriptome | No | +2 | 27.9 | b8, b9, b10 | N/A |

TABLE 2-continued

| Peptide Number | Peptide Sequence (*indicates 13C15N amino acid in reference standard unless notes otherwise) | Name | Gene symbol | Percent Purity of standard | Sequence Homology | Discovery study (rat and/or mouse) | Endogenous Observed in SRM assay | Dominant Charge State | Collision Energy | Top Peptide ions monitored (Qtrap 5500) | Peptide Ion quantified |
|---|---|---|---|---|---|---|---|---|---|---|---|
| 60 | CLVLSDPCEL*K | | | 99 | Rat | | No | +2 | 33.8 | y5, y6, y7 | N/A |
| 61 | DGTPTLQESV*DPK | | | 100 | Mouse and rat | | Yes | +2 | 38.5 | y8, y9, y11, b3 | Too low to quantify |
| 62 | SLSQQIENI*R (13C labeled only) | Collagen alpha-1(I) chain | Col1a1 | 86 | Mouse rat and human | Proteome | Yes | +2 | 34.3 | y6, y7, y8, y9 | y6 |
| 63 | IPLENLQII*R (13C labeled only) | Epidermal Growth Factor Receptor | EGFR | 96 | Mouse rat and human | Proteome | Yes | +2 | 34.6 | y5, y6, y7, y8 | y7 |
| 92 | NVVTDHGSCV*R | | | 70 | Mouse rat and human | | Yes | +3 | 23.1 | y6, y7, y8 | y6 |
| 64 | EVSFDVEL*PK (13C Labeled only) | Inter-alpha-trypsin inhibitor heavy chain H3 | Itih3 | 92 | Mouse rat and human | Proteome | Yes | +2 | 29.8 | y5, y6, y7, y8 | y5 |
| 65 | AYVAFPD*FFR | Maltase Glucomylase | Mgam | 88 | Mouse and human | Proteome | Yes, mouse, no human | +2 | 34.1 | y5, y6, y7, y8 | y5 |
| 83 | SSVYANAFPSTPVNPL*R (13C Labeled only) | | | 82 | Human | Proteome | No | +2 | 38.6 | y3, y6, y9, b8 | N/A |
| 66 | NFNPPII*SR (13C labeled only) | Coagulation factor V | F5 | 93 | Mouse rat and human | Proteome | Yes | +2 | 30.6 | y6, y7, y8, b8 | y6 |
| 67 | LWWLDL*K (13C labeled only) | Hemopexin | Hpx | not determined | Mouse rat and human | Proteome | Yes | +2 | 26.4 | y4, y5, y6, b5 | y5 |
| 68 | TIEAEAAHGTV*TR | Isocitrate dehyrogenase [NADP], mitochondrial | Idh2 | 98 | Mouse rat and human | Proteome | No | +3 | 22.2 | y5, y6, y7, y8 | N/A |

TABLE 2-continued

| Peptide Number | Peptide Sequence (*indicates 13C15N amino acid in reference standard unless notes otherwise) | Name | Gene symbol | Percent Purity of standard | Sequence Homology | Discovery study (rat and/or mouse) | Endogenous Observed in SRM assay | Dominant Charge State | Collision Energy | Top Peptide ions monitored (Qtrap 5500) | Peptide Ion quantified |
|---|---|---|---|---|---|---|---|---|---|---|---|
| 69 | EAEAAIYHLQLFEEL*R (13C labeled only) | Pyruvate Kinase, M2 | Pkm2 | 85 | Mouse rat and human | Proteome | No | +3 | 37.7 | y5, y6, y7, y8 | N/A |
| 70 | VLEPTL*K | Vitamin D-binding protein | Gc | 94 | Mouse and human | Proteome | Yes | +2 | 23.3 | y4, y5, y6 | y4 |
| 71 | FEDGVLDPDYP*R | Vitronectin | VTN | 99 | Rat and human | Proteome | Yes | +2 | 34.5 | y5, y6, y7, y8 | y5 |
| 72 | FAHTVVT*SR | Inter-alpha-trypsin inhibitor, Heavy chain 4 | ITIH4 | 88 | Mouse rat and human | Proteome | Yes | +3 | 16.1 | y3, y4, b3, b4 | y3 |
| 74 | TLTLLSV*TR | CEACAM5 | CEA | 77 | Human, No Murine homologs | N/A Human Prognostic marker | No | +2 | 27.9 | y5, y6, y8, b5 | Monitoring y5 |
| 75 | LCGTFLGGPKPP*QR | Cathepsin B | Ctsb | 98 | Human | Proteome | Yes | +3 | 26.3 | y5, y6, y7, y8 | y8 |
| 77 | GYVIKPL*VWV (13C labeled only) | Serum Amyloid P | APCS | 87 | Human | Proteome | Yes | +2 | 27.0 | y6, y7, y8, b9 | b9 |
| 78 | IFFESVYGQC*K | Fetuin B | FetuB | 77 | Human | Proteome | Yes | +2 | 31.7 | y6, y7, y8, y9 | y9 |
| 79 | ESDYSVVSL*K (13C labeled only) | C-reactive protein | Crp | 99 | Human | Proteome | Yes | +2 | 28.2 | y5, y6, y8 | y6 |
| 82 | FTVDRPFLFLIY*EHR | heparin cofactor 2 | SerpinD1 | 87 | Human | Proteome | Yes | +3/+4 | 30.0/24.2 | y5, y6, y7, b8 | y5 |
| 84 | LAGAPSEDPQFP*K | Sulfhydryl Oxucase 1 | QSOX1 | 92 | Human | Proteome | Yes | +2 | 31.3 | y5, y7, y9, b4 | y9 |

TABLE 2-continued

| Peptide Number | Peptide Sequence (*indicates $^{13}C^{15}N$ amino acid in reference standard unless notes otherwise) | Name | Gene symbol | Percent Purity of standard | Sequence Homology | Discovery study (rat and/or mouse) | Endogenous Observed in SRM assay | Dominant Charge State | Collision Energy | Top Peptide ions monitored (Qtrap 5500) | Peptide Ion quantified |
|---|---|---|---|---|---|---|---|---|---|---|---|
| 85 | AEEYEFLTPVEEAP*K | Rho-GDP Dissociation Inhibitor 1, Isoform a (RhoGDI) | Arhgdia | 88 | Human | Proteome | Yes | +2 | 38.4 | y7, y9, y10 | y7 |
| 86 | WDEELAAFA*K | Peptidase inhibitor 16 | PI16 | Peak 1 is 21% and Peak 2 is 66% | Human | Proteome | Yes | +2 | 29.1 | y6, y8, y9 | y8 |
| 87 | GPFPQEL*VR (13C Labeled only) | Cadherin-2 (N-Cadherin) | Cdh2 | 90 | Mouse rat and human | Proteome | Yes | +2 | 25.6 | y6, y7, b3 | y6 |
| 88 | WEYYDSVY*TER | Dipeptidyl peptidase 4 | DPP4 | 75 | Mouse rat and human | Proteome | Yes | +2 | 37.1 | y7, y8, y9, b5 | y9 |
| 89 | VTGVVL*FR (13C Labeled only) | extra-cellular superoxide dismutase [Cu-Zn] | Sod3 | 93 | Human | Proteome | Yes | +2 | 23.9 | y4, y5, y6, y7 | y6 |
| 90 | DVDIDSYPDEELPCSA*R | Thrombo-spondin-4 | Thbs4 | 92 | Mouse rat and human | Proteome | Yes | +2 | 41.5 | y5, y9, y10, b7 | y10 |
| 91 | GFGPPATN*QFTTK | receptor-type tyrosin-protein phosphatase mu | Ptprm | 98 | Mouse rat and human | Proteome | Yes | +2 | 37.5 | y7, y9, b4 | y9 |

After peptide selection, a synthetic form of each targeting peptide of interest, containing one heavy labeled stable isotope amino acid, was synthesized. This peptide can either be used for absolute quantitative analysis, or it can be used for relative quantitative analysis. The embodiments in the examples infra use relative quantification with unpurified synthetic reference standards spiked into the samples at known dilution factors. In complex mixtures such as serum, multiple isobaric peptides from different proteins will produce peaks at similar elution times. A heavy reference standard can assist in identifying the correct retention time and transition order of the endogenous peptide, thus preventing quantification of the incorrect peptide. An isotopically labeled peptide reference standard unique to each selected biomarker candidate was synthesized by the UW-Madison Biotechnology Center's peptide synthesis core facility, with the incorporation of at least one of $^{13}$C and $^{15}$N labeled amino acids in each reference peptide. (Table 2.)

Sample Collection.

Blood samples were collected, processed and stored following the standard operating procedure published by the Early Detection Research Network (Tuck, M. K. et al., *J Proteome Res* 2009, 8, (1), 113-7). Approximately 1.5 ml of blood was collected from the retro-orbital sinus into Protein LoBind tubes (Eppendorf). The time of day for blood collection was controlled across the study, with all blood samples collected within a 2-hour window. Blood was left to clot at room temperature for 30-60 minutes before centrifugation at room temperature for 20 minutes at 1,200 g (Eppendorf 5415c). The serum was then transferred to new Protein LoBind tubes using sterile LoRetention Dualfilter pipet tips (Eppendorf) and frozen at −80° C. until use.

Sample Preparation.

Serum was washed five times with 10 kDa MWCO Amicon Centriprep units with 5 mL of 20% acetonitrile/80% Milli-Q $H_2O$ at 1500 g for 1 h at 4° C. followed by lyophilization. For murine studies, the major blood proteins (albumin, transferrin, and IgG) were removed from a 2 mg aliquot of resolublized serum, using a 4.6 mm×100 mm mouse MARS column (Agilent Technologies) according to the manufacturer's protocol. (Human sample preparation described in Example 4, infra.) Proteins not retained by the column were collected, concentrated, and precipitated with trichloroacetic acid as previously described (Ivancic, M. M. et al., *J Proteome Res* 2013, 12, (9), 4152-66). A Pierce™ BCA protein concentration assay was performed on resolublized samples according to the manufacturer's instructions (Thermo Fisher Scientific).

A 100 μg aliquot of serum protein from each sample underwent reduction and alkylation of cysteine residues, followed by digestion using sequencing grade porcine trypsin (Promega) at a 1:50 trypsin-protein ratio. Prior to reduction and alkylation, the stable isotope labeled peptide reference standard of each target endogenous peptide was added to the serum protein sample. Trypsin digestions were performed at 37° C. overnight. The resultant peptides were desalted on SPEC C18 Pipette Tips (Agilent Technologies) according to manufacturer's instructions. Eluted peptides were dried using a vacuum centrifuge.

LC-SRM-MS Method.

Synthetic peptides were resolubilized in 0.1% formic acid, 5% acetonitrile, and water to a concentration of 1 μg/μl endogenous peptides. Liquid chromatography separation was achieved using a NanoLC ultra 2D (Eksigent) equipped with a nanoflex cHiPLC. The microfluidic chip was a 75 μm diameter 15 cm length column with C18 3 μm resin at a 120 Å pore size and the temperature of the cHiPLC system was set to 37° C. A 90 minute gradient at a flow rate of 300 nl/min was applied as follows: starting conditions were set at 97% 0.1% formic acid in water (buffer A) and 3% 0.1% formic acid in acetonitrile (buffer B) and increased linearly to 15% B by 30 minutes. Buffer B was increased linearly to 35% by 60 minutes and then a steeper gradient to 50% B was applied to 85 minutes. The gradient was switched back to starting conditions at 90 minutes. Peptides were eluted directly into a 5500 QTrap (AbSciex). Peptide precursors were selected in Q1 followed by fragmentation in q2 and subsequent monitoring of the top 3-4 transitions for each peptide in Q3. All Q1 and Q3 masses were measured at unit resolution. To maximize dwell times, a 5-minute scheduling window was applied with a 1.5 second cycle time. Method development and peak analysis was done using Skyline software.

Data Processing.

Mass spectrometry results were imported into Skyline and peaks integrated. Each peptide was evaluated using the average peak area of the most intense transition over three technical replicates. For each protein, an average ratio of $F_1$-Pirc/$F_1$-wildtype was calculated for each of the peptides. P-values were obtained using a two-tailed Student's t-test assuming a normal distribution.

The diagnostic capability of serum protein markers on an individual level and as a panel was determined by Receiver Operator Characteristic (ROC) analysis using the JROCFIT web-based calculator (see, Eng J., ROC analysis: web-based calculator for ROC curves, provided on the Johns Hopkins University School of Medicine website), using the same test set of 14 $F_1$-Pirc and 10 $F_1$-wildtype animals. Data format 2 (binary response with confidence rating) was used with a total of three rating categories: 1=low confidence; 2=intermediate confidence; and 3=high confidence. First, each protein was rated for its diagnostic capacity as an individual protein. Next, a group of four specific proteins, chosen on the basis of their individual ROC analyses, was evaluated for its diagnostic potential as a panel. More details of the ROC analysis of single proteins and a panel are described below.

In proteomics, relative quantification often relies on the use of fold changes derived from a comparison of one biological condition (e.g. cancer) to another biological condition (e.g. no cancer). Most researchers assign an arbitrarily defined threshold expression change for the data being analyzed. Recently, reasonable threshold assignments for protein upregulation were defined by Serang and colleagues (Serang, O. et al., *J Proteome Res* 2013, 12, (10), 4556-65). They determined that a 1.2-fold change is a reasonable cut-off to consider a quantified protein upregulated. Because ROC analysis relies on quantitative cutoffs to determine a positive or negative test, the guideline set by Serang et. al. as a framework for assigning positive and negative results in the ROC analysis was used.

Proteins were partitioned into those expected to be upregulated or downregulated based on the two discovery studies (transcriptome/proteome). Tables 3 and 4 show the confidence ratings assigned (1-3) for each protein expression ratio (required by analysis format 2, binary response with confidence rating, on www.jrocfit.org). It was expected that LRG1, F5, VTN, MMP7, MMP10, CD44, ITIH3, ITIH4, HPX, and CFI would be upregulated based on discovery data. Accordingly, their protein ratings were based off of the 1.2-fold threshold (Serang, O. et al., *J Proteome Res* 2013, 12, (10), 4556-65). While below the 1.2 expression threshold, proteins upregulated in the 1.16-1.19 category with low confidence were considered to reduce the possibility of false negatives in the ROC analysis.

TABLE 3

Confidence ratings for expected upregulated colon cancer biomarkers

| Fold change/ Confidence rating | Description of rating |
|---|---|
| 1.1 or less = 3 | Indicates high positivity that there are no tumors |
| 1.11-1.15 = 2 | Indicates fairly high positivity that there are no tumors |
| 1.16-1.19 = 1 | Indicates can't definitively tell whether or not there are tumors, marked as a pos. test |
| 1.20-1.29 = 2 | Indicates fairly high positivity that there are tumors present |
| 1.30 or greater = 3 | Indicates very positive that the are tumors present |

The work by Serang and colleagues did not set a fold-change value considered reasonably significant for downregulation. Therefore, an expression ratio of 0.86 or lower was set as the cutoff for reasonable downregulation. While above the 0.86 threshold, proteins with a 0.87-0.89 expression ratio were considered downregulated with a low level of confidence to avoid introducing false negatives into the analysis. The downregulation cutoffs presented below for proteins were used:

TABLE 4

Confidence ratings for expected downregulated colon cancer biomarkers

| Fold change/ Confidence rating | Description of rating |
|---|---|
| 0.95 or greater = 3 | Indicates high positivity that there are no tumors |
| 0.90-0.94 = 2 | Indicates fairly high positivity that there are no tumors |
| 0.87-0.89 = 1 | Indicates can't definitively tell whether or not there are tumors, marked as a pos. test |
| 0.80-0.86 = 2 | Indicates fairly high positivity that there are tumors present |
| 0.79 or less = 3 | Indicates very positive that the are tumors present |

ROC Analysis of Candidates as a Panel.

The murine models indicated that EGFR, LRG1, ITIH4, and F5 had the greatest diagnostic potential as determined by their individual ROC analyses and the low variance in their wildtype concentrations (see Example 3, infra.). Therefore, these 4 proteins were selected for ROC analysis as a panel. Three different analyses for EGFR, LRG1, ITIH4, and F5 as a panel were done based on the number of individual positives for these proteins using the rating system above. The first analysis was the least stringent, requiring that only 1 protein show differential expression of the four in the panel. The second and third analyses required at least 2 and 3 positive values, respectively. As with the analysis using single proteins, format 2 (binary response with confidence rating) on JROCFIT was used. Confidence ratings were assigned based on the number of positive markers in the panel. Tables 5-7 are the ratings used for each of the three stringency levels tested.

TABLE 5

Confidence ratings for a panel in which 1 of 4 proteins must be positive

| Confidence rating | Description of rating |
|---|---|
| 3 | At least 3 markers are positive (Pos diagnosis) or all are negative (neg. diagaosis) |
| 2 | 2 markers are positive (pos diagnosis) |
| 1 | 1 marker is positive (pos diagnosis) |

TABLE 6

Confidence ratings for a panel in which 2 of 4 proteins must be positive

| Confidence rating | Description of rating |
|---|---|
| 3 | At least 3 are positive (pos diagnosis), or all are negative (neg diagnosis) |
| 2 | 2 markers are positive (Pos diagnosis) |
| 1 | 1 is positive (neg diagnosis) |

TABLE 7

Confidence ratings for a panel in which 3 of 4 proteins must be positive

| Confidence rating | Description of rating |
|---|---|
| 3 | All are positive (pos diagnosis), or all are negative (neg. diagnosis) |
| 2 | 3 are positive, 1 is negative (Pos diagnosis) or 1 is positive (negative diagnosis) |
| 1 | 2 are positive (neg diagnosis) |

Example 3: Serum Biomarkers Predict Tumor Formation in a Murine Model of Colon Cancer Transcriptomic and Proteomic Discovery Studies Identified Protein Biomarker Candidates for Validation in $F_1$-Pirc Rats.

Figure 3:
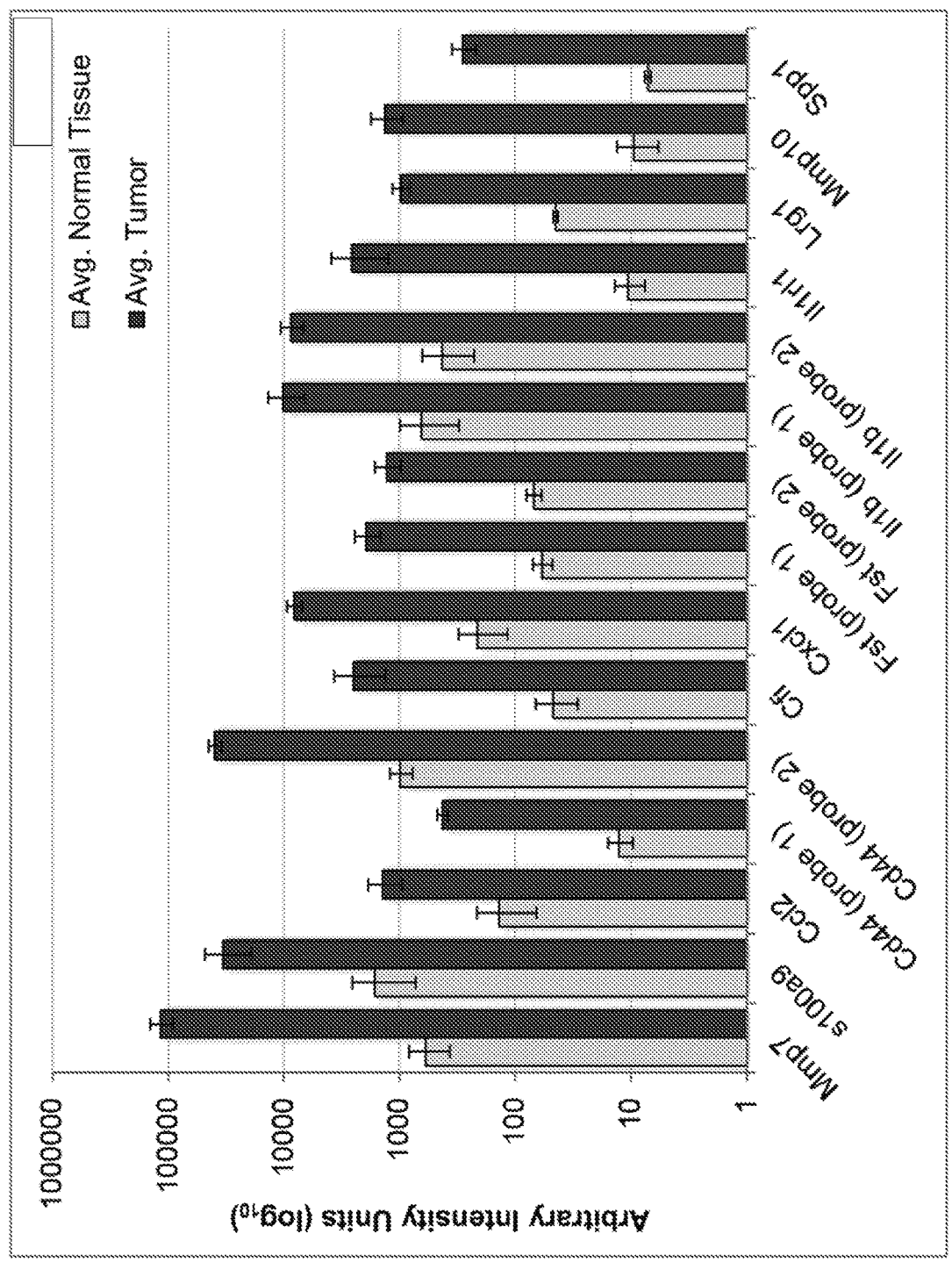
FIG. 3 illustrates selected results of gene expression profiling in normal colonic tissue and tumor tissue in an $Apc^{Pirc/+}$ rat model ("Pirc rats"). Gene transcripts upregulated in tumor compared to normal tissue were identified by Agilent Whole Genome Microarray. These candidates represent genes which: 1) show a 5-fold or greater upregulation in mRNA expression levels in tumors, 2) code for known or predicted secreted proteins, and 3) have some known biological significance to human colon cancer.
Figure 4:
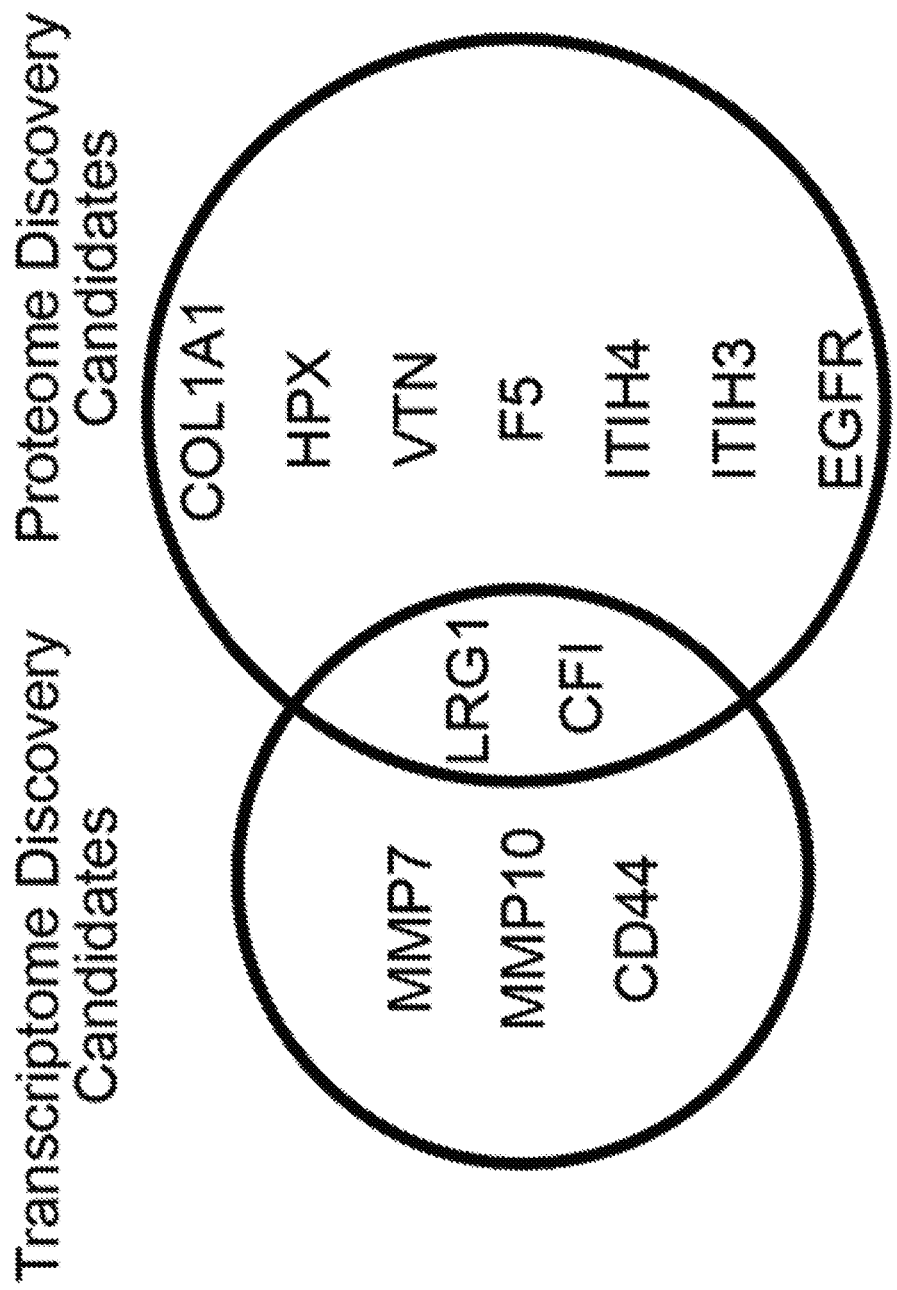
FIG. 4 presents a summary of candidates that were selected for selected reaction monitoring mass spectrometry experiment (SRM-MS) validation screening. Using SRM-MS, the endogenous forms of peptides from each of these proteins were successfully identified at quantifiable levels in the serum of $F_1$-Pirc rats.

A total of 928 microarray probes were differentially expressed by at least 5-fold between normal colonic tissue and tumors from $F_1$-Pirc rats. In total, 543 probes were more highly expressed in tumor tissue, while the remaining 415 probes were more highly expressed in normal tissue. For the purposes of this study, only those probes upregulated in tumor were considered. The list of probes was narrowed to 12 transcriptome candidates (15 total probes) by selecting those whose gene products are secreted and suggested to have potential biological significance to colon cancer based on published literature (FIG. 3). During SRM-MS method development, the endogenous proteins for 5 of the 12 transcriptome candidates and 9 of the 11 proteomic candidates were visible and quantifiable by mass spectrometry (see also Table 1). The final list of 12 proteins selected for validation included 3 candidates from the $F_1$-Pirc rat tumor transcriptome analysis, 7 from the $Apc^{Min/+}$ mouse serum proteomic study, with CFI and LRG1 shared between the two discovery strategies (FIG. 4).

Protein Expression Over Time Reveals Differential Expression Concordant with Increases in Tumor Multiplicity.

Figure 5A:
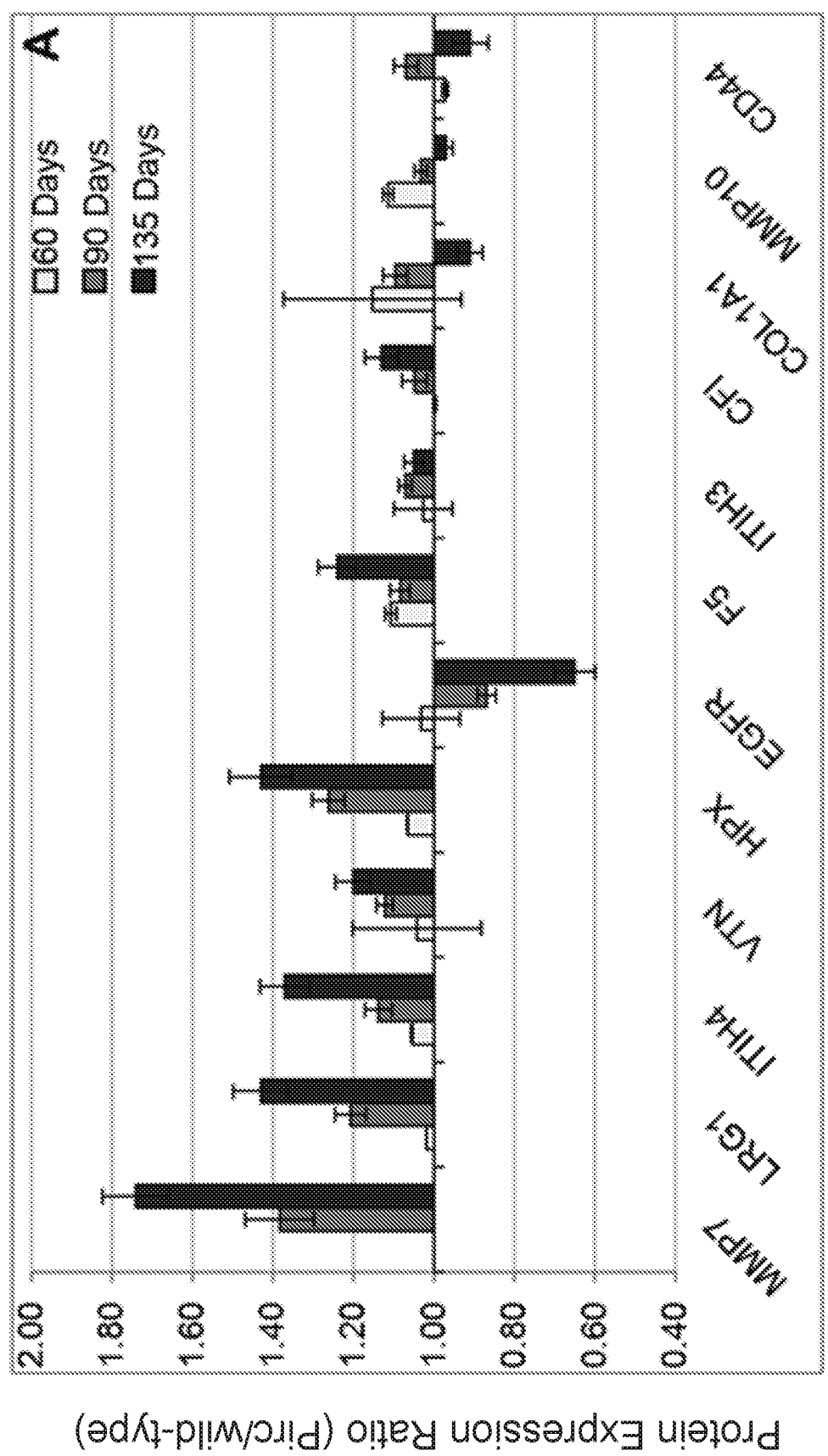
FIG. 5A presents protein biomarker expression in serum displayed over a time course.

Quantitative proteomics revealed that MMP7, LRG1, ITIH4, VTN, HPX and F5 proteins show increased levels in blood serum over time. (FIG. 5, Table 8.) Average EGFR expression in $F_1$-Pirc rats was significantly downregulated at 135 days, as observed in the prior proteomics discovery study (Ivancic, M. M. et al., *J Proteome Res* 2013, 12, (9), 4152-66). In all, seven proteins showed significant changes in levels of serum in tumor-bearing Pirc rats.

TABLE 8

Summary of protein expression and statistical analysis for individual biomarker candidates

| Protein name | Protein symbol | NCBI Number | Time point (days of age) | Average expression ratio (Pirc/WT) | p-value | Sensitivity | Specificity | AUC | $F_1$-Wildtype variance over time |
|---|---|---|---|---|---|---|---|---|---|
| Matrix metalloproteinase-7 | MMP7 | NP_036996 | 60 | 1.12 | 0.46 | ND$^a$ | ND$^a$ | ND$^a$ | 25.7% |
| | | | 90 | 1.38 | 0.04 | 57.1% | 80.0% | 0.664 | |
| | | | 135 | 1.74 | 0.004 | 85.7% | 80.0% | 0.843 | |
| Leucine-rich alpha-2 glycoprotein | LRG1 | NP_001009717 | 60 | 1.07 | 0.06 | 16.7% | 100.0% | 0.674 | 12.9% |
| | | | 90 | 1.21 | 0.03 | 64.3% | 90.0% | 0.857 | |
| | | | 135 | 1.43 | <0.001 | 92.9% | 90.0% | 0.907 | |
| Inter-alpha trypsin inhibitor, heavy chain 4 | ITIH4 | NP_062242 | 60 | 1.11 | 0.06 | 50.0% | 83.3% | 0.701 | 15.0% |
| | | | 90 | 1.14 | 0.03 | 28.6% | 100.0% | 0.649 | |
| | | | 135 | 1.37 | 0.001 | 78.6% | 90.0% | 0.871 | |
| Vitronectin | VTN | NP_062029 | 60 | 1.03 | 0.61 | 8.3% | 91.7% | 0.504 | 16.2% |
| | | | 90 | 1.12 | 0.001 | 35.7% | 100.0% | 0.821 | |
| | | | 135 | 1.20 | 0.02 | 71.4% | 90.0% | 0.854 | |
| Hemopexin | HPX | NP_445770 | 60 | 1.15 | 0.006 | 50.0% | 100.0% | 0.708 | 23.3% |
| | | | 90 | 1.26 | <0.001 | 78.6% | 100.0% | 0.882 | |
| | | | 135 | 1.43 | 0.0027 | 85.7% | 80.0% | 0.792 | |
| Epidermal growth factor receptor | EGFR | NP_113695 | 60 | 0.97 | 0.33 | 8.3% | 100.0% | 0.632 | 11.8% |
| | | | 90 | 0.87 | 0.002 | 50.0% | 100.0% | 0.832 | |
| | | | 135 | 0.65 | <0.001 | 100.0% | 80.0% | 0.939 | |
| Coagulation factor V | F5 | NP_001041343 | 60 | 1.00 | 0.94 | 8.3% | 100.0% | 0.545 | 11.5% |
| | | | 90 | 1.08 | 0.08 | 21.4% | 100.0% | 0.679 | |
| | | | 135 | 1.24 | 0.007 | 64.3% | 90.0% | 0.757 | |
| Inter-alpha trypsin inhibitor, heavy chain H3 | ITIH3 | NP_059047 | 60 | 1.03 | 0.57 | 25.0% | 91.7% | 0.615 | 16.3% |
| | | | 90 | 1.07 | 0.02 | 14.3% | 100.0% | 0.679 | |
| | | | 135 | 1.05 | 0.34 | 14.3% | 90.0% | 0.428 | |
| Complement Factor I | CFI | NP_077071 | 60 | 1.04 | 0.59 | 16.7% | 91.7% | 0.576 | 23.9% |
| | | | 90 | 1.08 | 0.26 | 21.4% | 90.0% | 0.867 | |
| | | | 135 | 1.13 | 0.24 | 50.0% | 80.0% | 0.820 | |
| Collagen, Type I Alpha 1 | COL1A1 | NP_445756 | 60 | 1.11 | 0.09 | 8.3% | 91.7% | 0.309 | 57.6% |
| | | | 90 | 1.1 | 0.11 | 7.1% | 80.0% | 0.371 | |
| | | | 135 | 0.91 | 0.18 | 42.9% | 70.0% | 0.592 | |
| Matrix Metalloproteinase 10 | MMP10 | NP_598198 | 60 | 1.02 | 0.81 | 8.3% | 83.3% | 0.462 | 12.0% |
| | | | 90 | 1.03 | 0.30 | 7.1% | 100.0% | 0.561 | |
| | | | 135 | 0.97 | 0.48 | 0.0% | 90.0% | 0.482 | |
| CD44 Antigen | CD44 | NP_037056 | 60 | 1.05 | 0.48 | 16.7% | 75.0% | 0.286 | 17.8% |
| | | | 90 | 1.07 | 0.25 | 21.4% | 90.0% | 0.755 | |
| | | | 135 | 0.91 | 0.33 | 7.1% | 80.0% | 0.672 | |

Figure 5B:
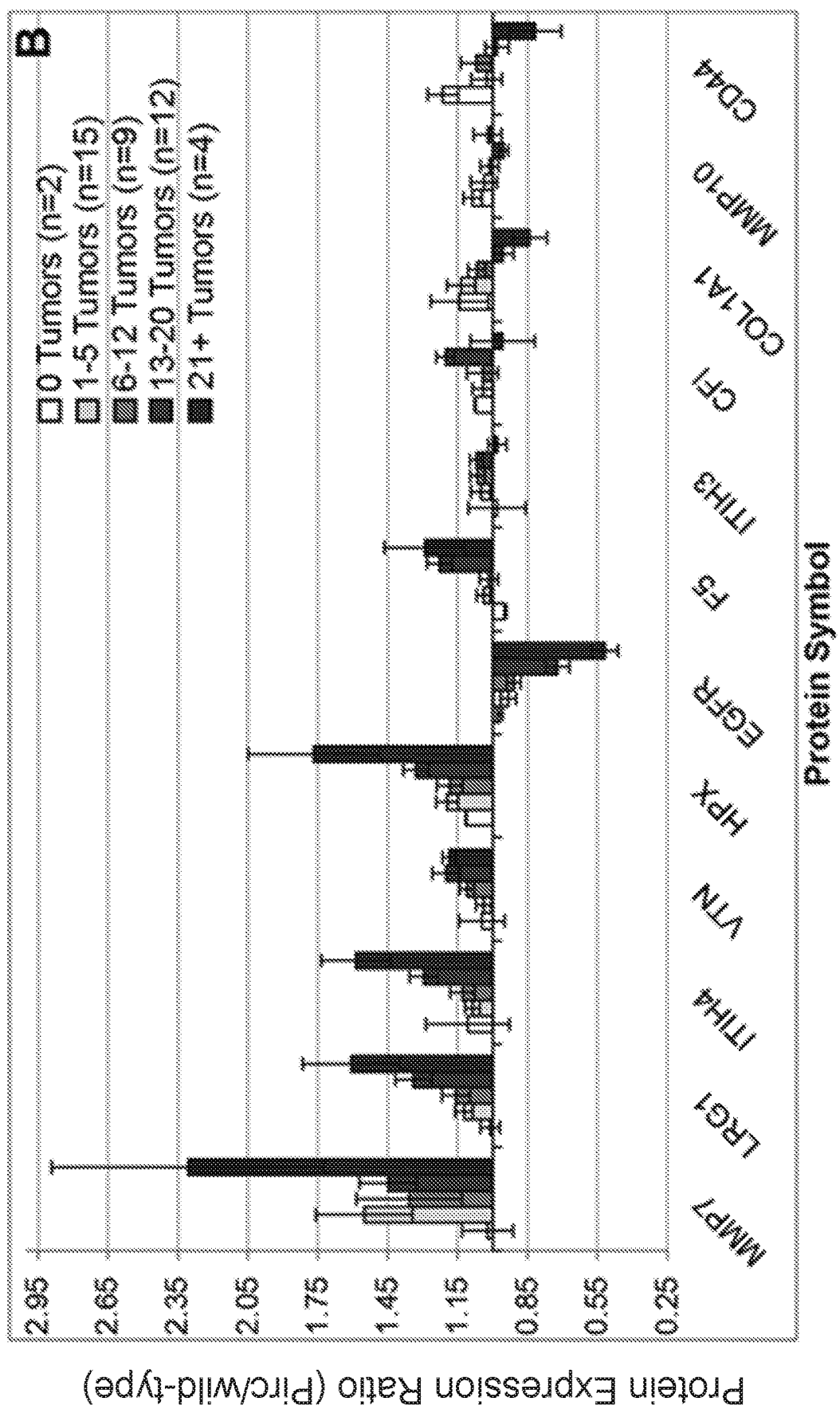
FIG. 5B presents protein biomarker expression in serum displayed as a function of large intestinal tumor burden.
Figure 6A:
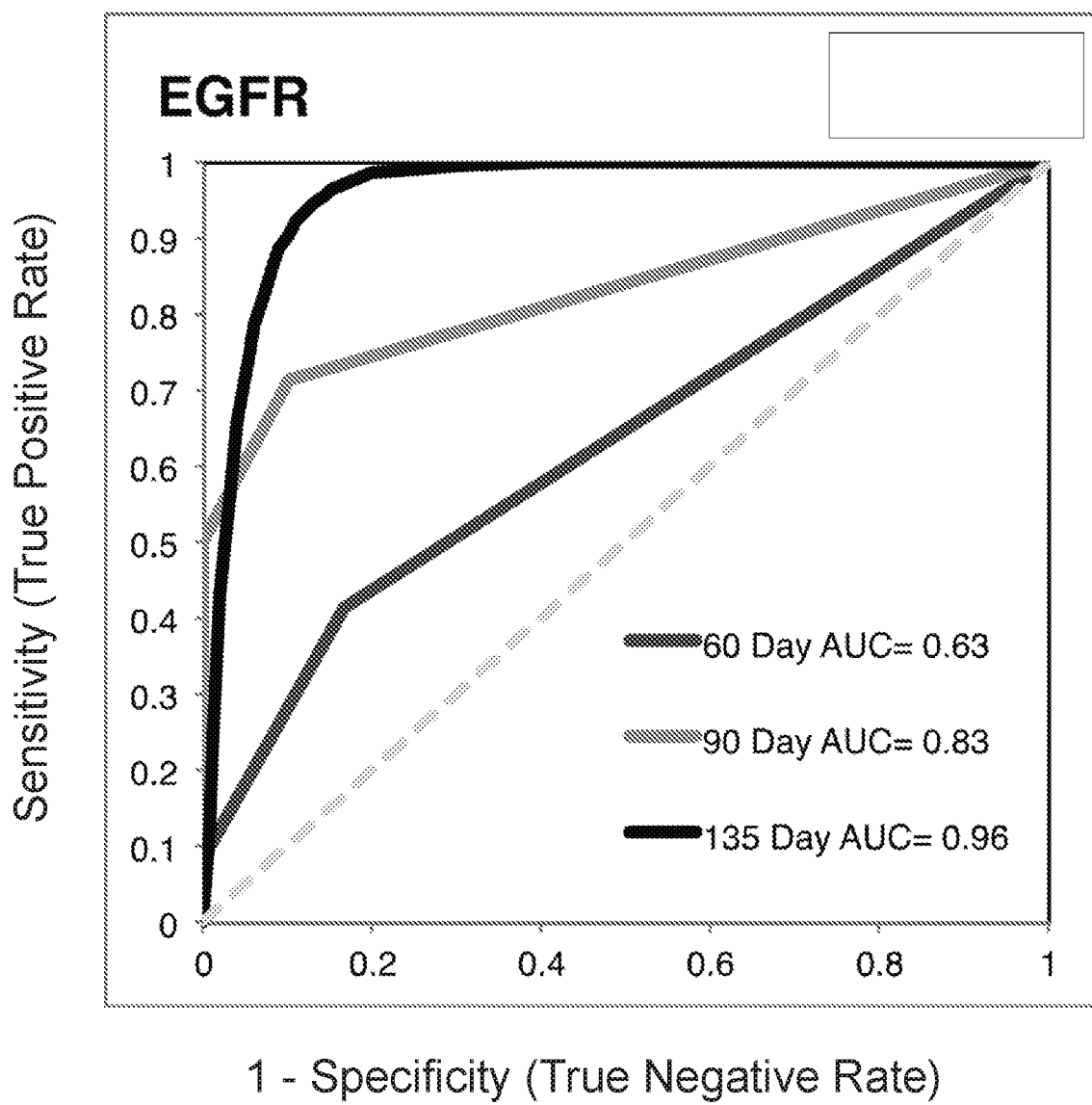
FIG. 6A present Receiver Operator Characteristic (ROC) analyses of biomarker EGFR indicating diagnostic utility as a protein biomarker to detect tumors in $F_1$-Pirc rat serum.
Figure 6B:
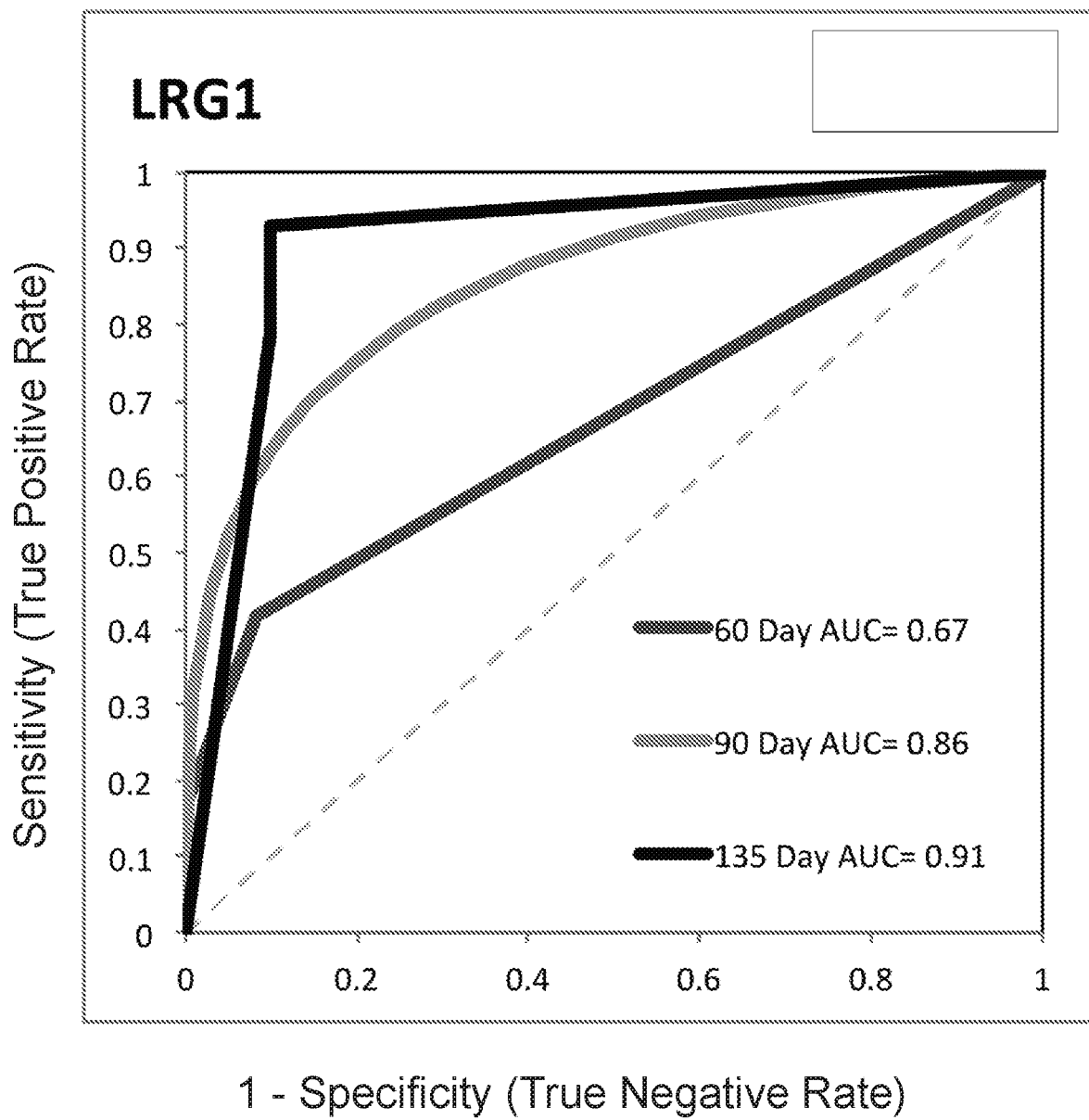
FIG. 6B present Receiver Operator Characteristic (ROC) analyses of biomarker LRG1 indicating diagnostic utility as a protein biomarker to detect tumors in $F_1$-Pirc rat serum.
Figure 6C:
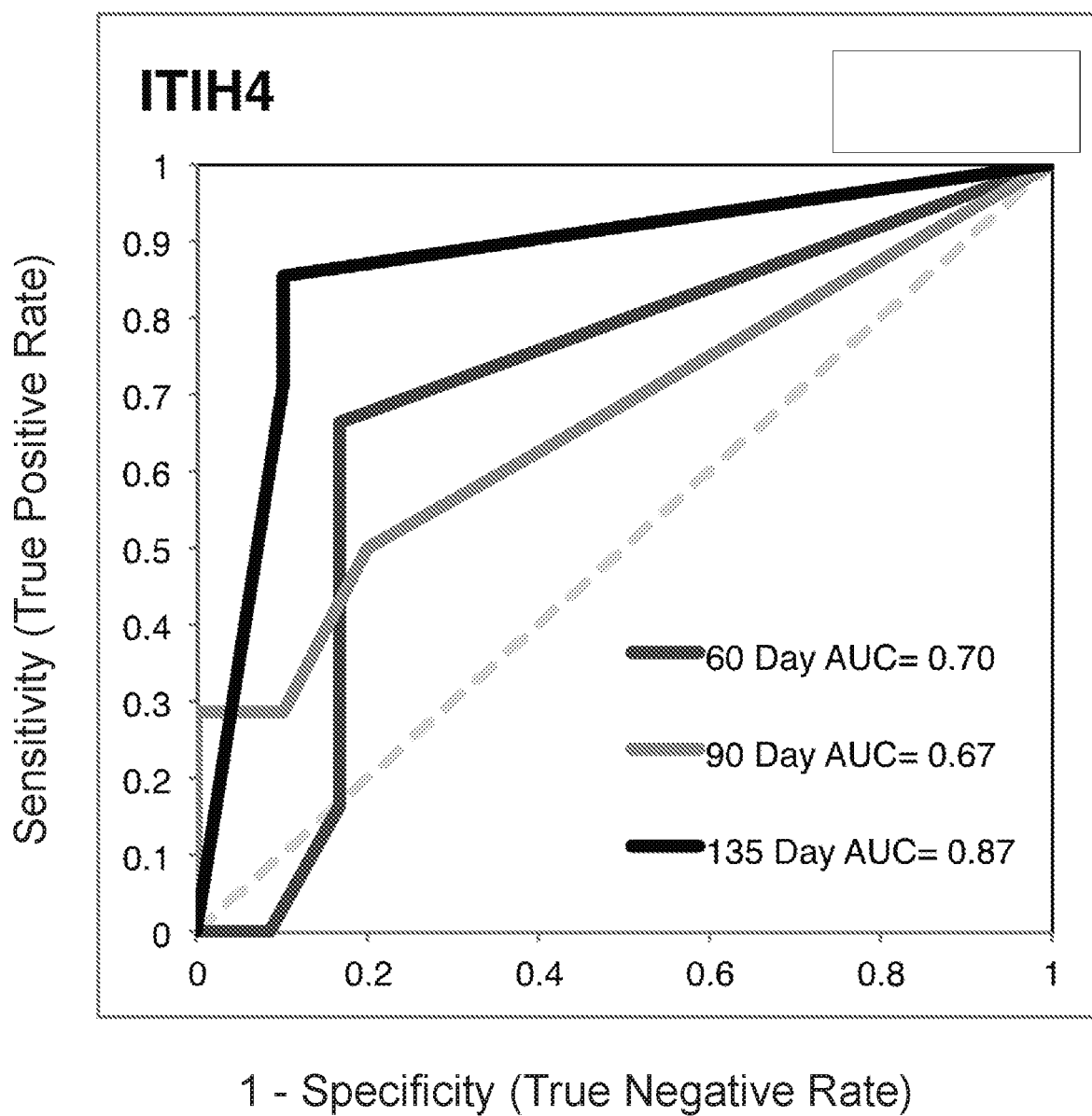
FIG. 6C present Receiver Operator Characteristic (ROC) analyses of biomarker ITIH4 indicating diagnostic utility as a protein biomarker to detect tumors in $F_1$-Pirc rat serum.
Figure 6D:
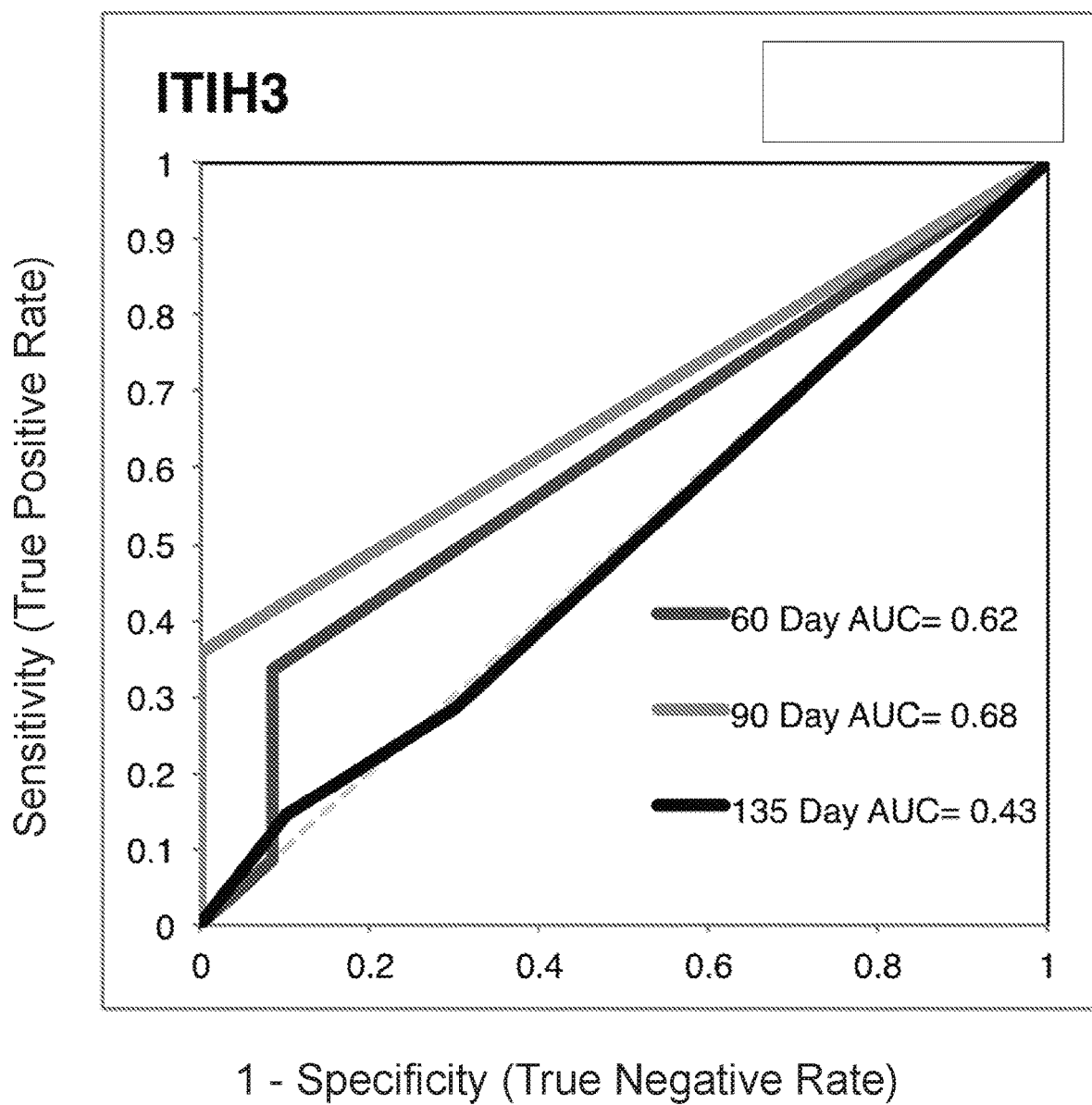
FIG. 6D present Receiver Operator Characteristic (ROC) analyses of biomarker ITIH3 indicating diagnostic utility as a protein biomarker to detect tumors in $F_1$-Pirc rat serum.

At the 60, 90, and 135-day time points, $F_1$-Pirc rats averaged 2±2, 7±4, and 19±5 colonic tumors, respectively. (Table 9.) Tumor counts for the small intestine could be obtained only upon dissection at the terminal time point of 135 days, and averaged 13±6 tumors. Of the 26 colonic tumors monitored by colonoscopy, 21 (81%) grew, 4 (15%) were static, and 1 regressed. The magnitude of expression change compared to wildtype rats was generally proportional to tumor burden. (FIG. 5B.)

TABLE 9

Tumor counts at the 60, 90, and 135-day time points

| Pirc Rat* | Large Intestine 60 days | Large intestine 90 days | Large intestine 135 days | Small intestine 135 days | Total intestine 135 days |
|---|---|---|---|---|---|
| 1 | 0 | 5 | 16 | 4 | 20 |
| 2 | 2 | 5 | 15 | 5 | 20 |
| 3 | 2 | 6 | 15 | 7 | 22 |
| 4 | 2 | 8 | 17 | 6 | 22 |
| 5 | 2 | 6 | 17 | 6 | 23 |
| 6 | 3 | 6 | 18 | 5 | 23 |
| 7 | 5 | 15 | 20 | 3 | 23 |
| 8 | 1 | 2 | 17 | 12 | 29 |
| 9 | 2 | 7 | 19 | 13 | 32 |
| 10 | 1 | 2 | 24 | 8 | 32 |
| 11 | 9 | 15 | 33 | 9 | 42 |

TABLE 9-continued

Tumor counts at the 60, 90, and 135-day time points

| Pirc Rat* | Large Intestine 60 days | Large intestine 90 days | Large intestine 135 days | Small intestine 135 days | Total intestine 135 days |
|---|---|---|---|---|---|
| 12 | 2 | 6 | 13 | 7 | 20 |
| 13 | 0 | 9 | 24 | 2 | 26 |
| 14 | 3 | 7 | 21 | 7 | 28 |

Protein Candidates have Diagnostic and Prognostic Utility for Detection of Colorectal Cancers and Precancerous Conditions.

The diagnostic ability of each biomarker to identify the presence of intestinal tumors was evaluated in two ways. First, the statistical significance of the ratio of average protein expression in $F_1$-Pirc rats compared to $F_1$-wildtype rats was determined. (Table 8.) The average area ratios of MMP7, LRG1, ITIH4, VTN, HPX, EGFR and F5 each changed significantly (p<0.05) by 135 days. Except for F5, each of these proteins also shows a significant change by 90 days. A published histological review of colon polyps from $F_1$-Pirc rats shows that the vast majority of tumors are noninvasive adenomas within the time range studied (Amos-Landgraf, J. M. et al., *Proc Natl Acad Sci USA* 2007, 104, (10), 4036-41), thus suggesting that the differentially expressed proteins can hold potential to identify polyps at the early adenoma stage. Further, the lack of protein expression changes at 60 days gives increased confidence that changes detected at the 90 and 135-day time points are directly or indirectly owing to the presence of the polyps and not due to an extra-tumoral effect of the Apc mutation.

ROC analysis was then used to evaluate the potential of each protein to diagnose early colonic neoplasia among the group of 14 $F_1$-Pirc and 10 $F_1$-wildtype rats. Table 8 summarizes the sensitivity, specificity, and area under the curve (AUC) of each protein biomarker at 60, 90 and 135 days. (See also FIG. 6.) As with the analysis by p-values, AUCs showed greater diagnostic potential at 90 and 135 days than at 60 days, with the sensitivity increasing as tumor burden increased. The most predictive proteins were LRG1 and EGFR, which had 1 and 0 false negatives, respectively, at 135 days. These proteins also had very few false positives (1 and 2, respectively), again indicating that their changes in expression in serum are tumor-specific. Among other proteins that show sensitivity and specificity at the 135-day time point are MMP7, ITIH4 and HPX, MMP10, and CD44.

A Protein Panel has High Sensitivity and Specificity for Identifying Early-Stage Colon Adenomas.

Figure 7:
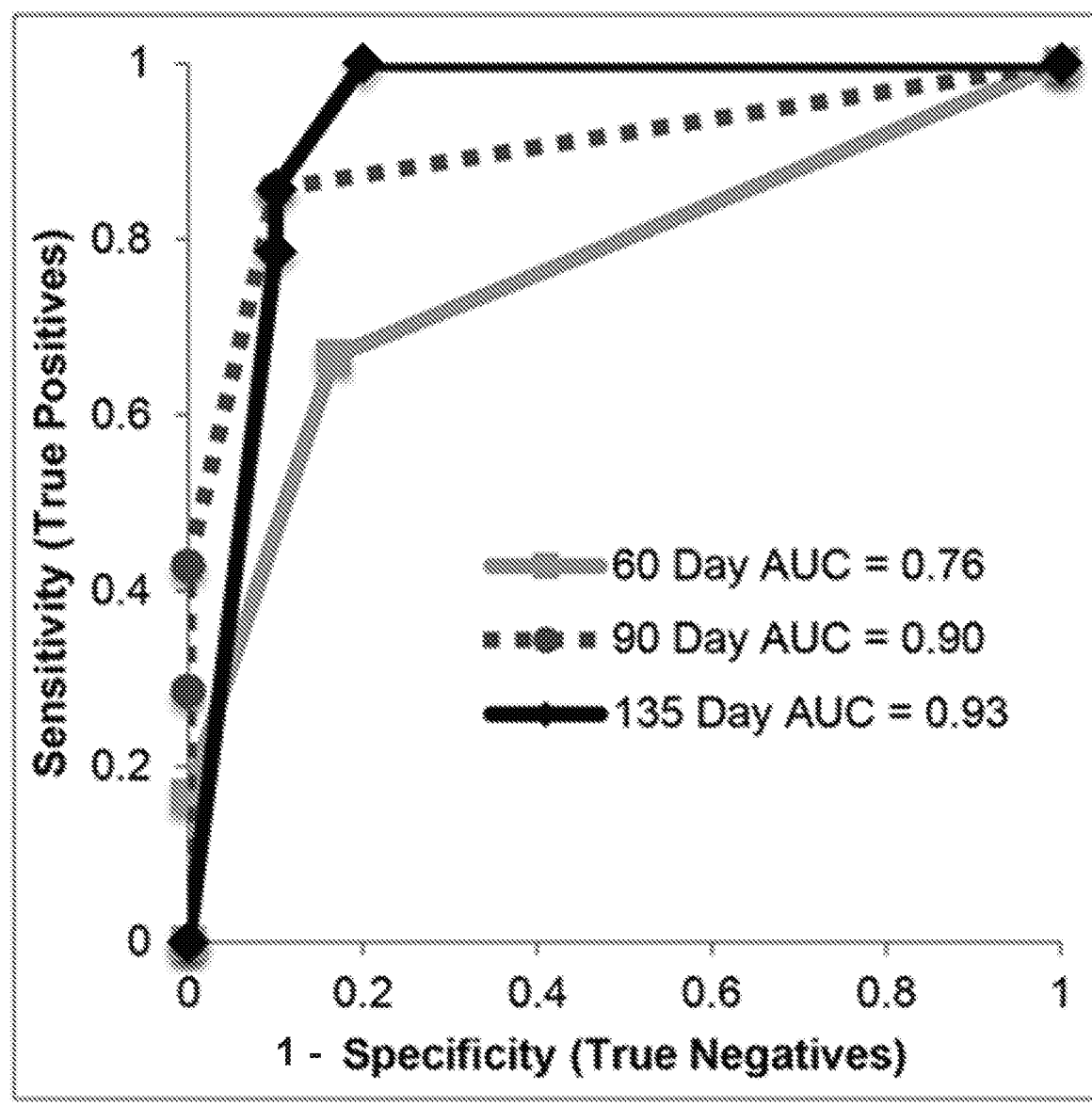
FIG. 7 presents an ROC analysis of a panel comprised of epidermal growth factor receptor (EGFR), Leucine-rich alpha-2-glycoprotein (LRG1), inter-alpha trypsin inhibitor, heavy chain H4 (ITIH4), and coagulation factor V (F5) for detecting tumors in $F_1$-Pirc rats from serum.

To improve the overall sensitivity for detecting the earliest adenomas, several of the proteins were analyzed for their predictive ability as a panel. LRG1, ITIH4, EGFR and F5 were chosen because they showed significant differential expression in $F_1$-Pirc rats and showed the least variance in $F_1$-wildtype protein concentration over time (15% or less). FIG. 7 and Table 10 highlight the sensitivity and specificity of this panel to identify rats with colonic polyps. Sensitivity was highest when the threshold for positive diagnosis was set to require only a single protein in the panel to show a positive result. Importantly, at 60 and 90 days the sensitivity increased using the four-protein panel. The panel reduced the number of false negatives from 6 (ITIH4 alone) to 4 at 60 days, and reduced it even further at 90 days from 5 (LRG1 alone) to 2. Maximally, 2/10 samples (20%) showed false positives at 60, 90, and 135 days.

TABLE 10

Summary of ROC analysis for a panel of four biomarkers (F5, EGFR, LRG1, and ITIH4)

| Minimum number of positive markers to make positive diagnosis | Time point | Sensitivity | Specificity | AUC |
|---|---|---|---|---|
| 1 Positive | 60 | 66.7% | 83.3% | 0.764 |
| | 90 | 85.7% | 90.0% | 0.900 |
| | 135 | 100% | 80.0% | 0.932 |

TABLE 10-continued

Summary of ROC analysis for a panel of four biomarkers (F5, EGFR, LRG1, and ITIH4)

| Minimum number of positive markers to make positive diagnosis | Time point | Sensitivity | Specificity | AUC |
|---|---|---|---|---|
| 2 Positives | 60 | 16.7% | 100% | 0.764 |
| | 90 | 42.9% | 100% | 0.843 |
| | 135 | 85.7% | 80.0% | 0.914 |
| 3 or more Positives | 60 | 0% | 100% | 0.764 |
| | 90 | 21.4% | 100% | 0.911 |
| | 135 | 78.6% | 90.0% | 0.904 |

A more stringent criterion for a positive diagnosis is that two or more proteins must show a positive result. With this criterion, the number of false positives decreased, as expected, and the number of false negatives increased significantly. Since the major goal is to detect the presence of colonic tumors with high sensitivity and no false negatives, it is counterproductive to require simultaneous changes in multiple positive markers. Therefore, the ROC analysis method was used to understand the sensitivity and specificity of each protein individually or in a panel, aiming to minimize the number of false negatives. The AUC value assumes that the sensitivity and specificity measurements are equally important (Grund, B. and Sabin, C., *Curr Opin HIV AIDS* 2010, 5, (6), 473-9). Accordingly, both sensitivity and specificity values (Table 10) are contemplated in the present methods to better assess the markers under consideration.

Example 4: Serum Biomarkers Predict Clinical Outcome in Human Colon Cancer Patients Biomarker Candidate and Selection.

The peptides identified and validated in animal models were used to conduct targeted proteomic analysis in humans. A list of more than 40 candidate proteins was identified by longitudinal study of blood proteins in tumor-bearing mice and rats (Example 3, supra) (Ivancic, M. M. et al., *J Proteome Res* 2013, 12, (9), 4152-66; Ivancic, M. M. et al., *Cancer Prev Res* 2014, 55, 7(11); 1160-9). Some of these markers overlap with other colon cancer biomarker discovery studies done in animals and humans (Hung, K. E. et al., *Cancer Prev Res (Phila)* 2009, 2, (3), 224-33; Chong, P. K. et al., *J Proteome Res* 2010, 9, (7), 3671-9; Ladd, J. J. et al., *Cancer Prev Res (Phila)* 2012, 5, (4), 655-64; Surinova, S. et al., *EMBO Mol Med* 2015, 7, 1153-1165). The candidate list of proteins from all of these studies was pared down to 30 proteins for biomarker screening in a human population. An emphasis was placed on selecting proteins with overlap across multiple biomarker studies and those with potential biological significance to colon cancer based on published literature. (Table 11.)

TABLE 11

List of candidate biomarkers selected for SRM-MS analysis

| Protein | Protein Symbol | Studies in which protein was indentified as a colon cancer biomarker in blood | Endogenous indentified in human serum during SRM method development? |
|---|---|---|---|
| Collagen alpha-1(I) chain | COL1A1 | Mouse, Rat | yes |
| Epidermal Growth Factor Receptor | EGFR | Mouse, Rat, Chong et. al. | yes |

TABLE 11-continued

List of candidate biomarkers selected for SRM-MS analysis

| Protein | Protein Symbol | Studies in which protein was indentified as a colon cancer biomarker in blood | Endogenous indentified in human serum during SRM method development? |
|---|---|---|---|
| Inter-alpha-trypsin inhibitor heavy chain H3 | ITIH3 | Mouse, Rat, Chong et. al. | yes |
| Maltase Glucoamylase | MGAM | Mouse | no |
| Coagulation factor V | F5 | Mouse, Rat, Hung et. al., Surinova et. al | yes |
| Hemopexin | HPX | Mouse, Rat | yes |
| Isocitrate dehydrogenase [NADP], mitochondrial | IGH2 | Mouse | no |
| Pyruvate Kinase, M2 | PKM2 | Mouse, Hung et. al. | no |
| Vitamin D-binding protein | GC | Mouse | yes |
| Vitronectin | VTN | Mouse, Rat, Surinova et. al. | yes |
| Inter-alpha-trypsin inhibitor heavy chain H4 | ITIH4 | Mouse, Rat, Surinova et. al. | yes |
| CD44 Antigen | CD44 | Rat, Surinova et. al | yes |
| CEACAM5 | CEA | Neither-Prognostic marker | no |
| Cathapsin B | CTSB | Mouse, Hung et. al. | yes |
| Leucine-rich alpha-2-glycoprotein | LRG1 | Mouse, Rat, Hung et. al. Ladd, et. al. and Chong et. al, Surinova et. al. | yes |
| Serum Amyloid P | APCS | Mouse, Chong et. al. | yes |
| Fetuin B | FETUB | Mouse, Surinova et. al. | yes |
| C-reactive protein | CRP | Mouse | yes |
| Matrilysin | MMP7 | Rat | no |
| Complement factor I | CFI | Mouse, Rat, Hung et. al. | yes |
| heparin cofactor 2 | SERPIND1 | Mouse | yes |
| Sulfhydryl Oxidase 1 | QSOX1 | Mouse | yes |
| Rho-GDP Dissociation Inhibitor 1, Isoform a (RhoGDI) | ARHGDIA | Mouse | yes |
| Peptidase inhibitor 16 | PI16 | Mouse | yes |
| Cadherin-2 (N-Cadherin) | CDH2 | Mouse | yes |
| Dipeptidyl peptidase 4 | DPP4 | Mouse | yes |
| extracellular superoxide dismulase [Cu—Zn] | SOD3 | Mouse | yes |
| Thrombospondin-4 | THBS4 | Mouse | yes |
| receptor-type tyrosine-protein phosphatase mu | PTPRM | Mouse | yes |

Patient Population.

Figure 8:
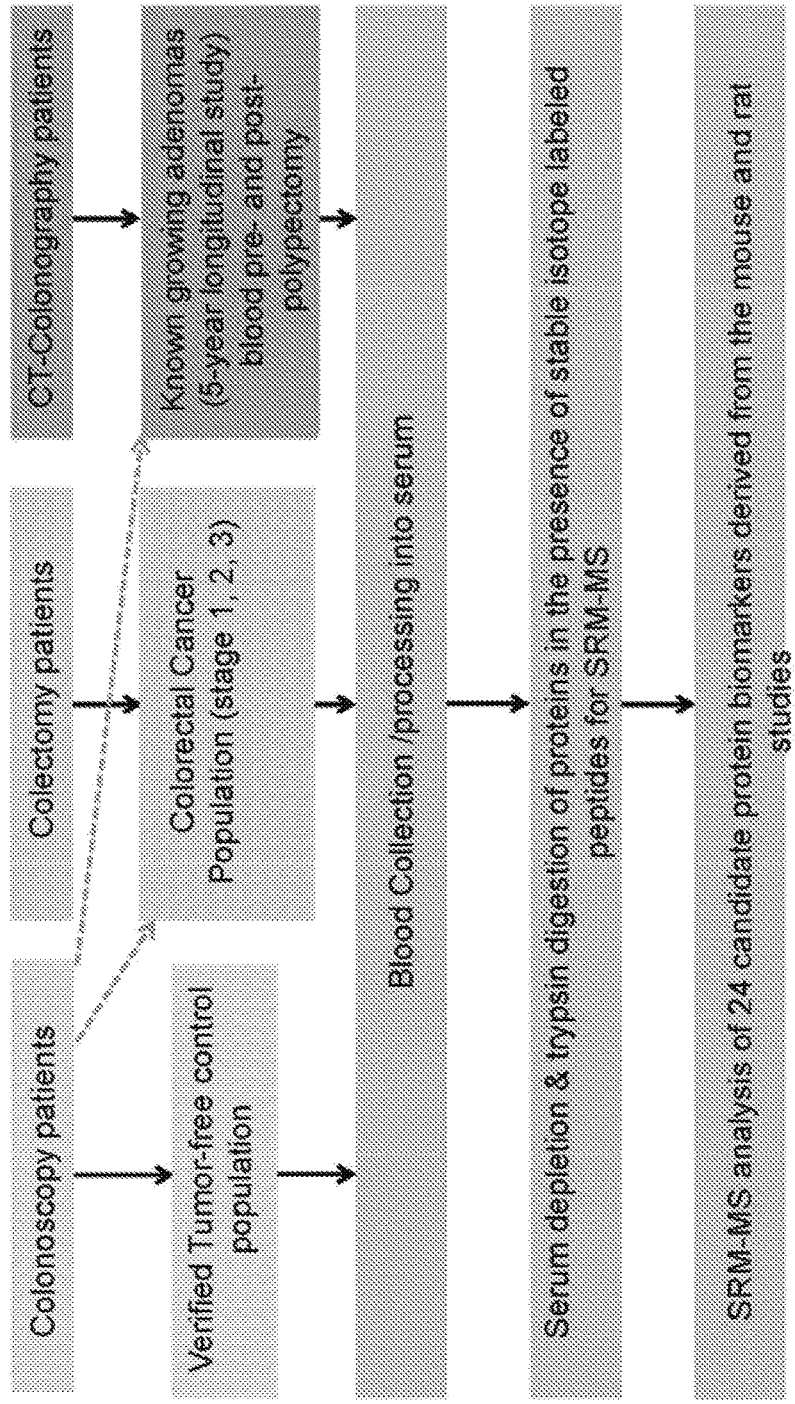
FIG. 8 presents the design of a human clinical study to determine the ability of biomarkers identified in animal models to predict, diagnose, and determine prognosis for humans with colorectal cancer, or those with precancerous stages of colon cancer.
Figure 9A:
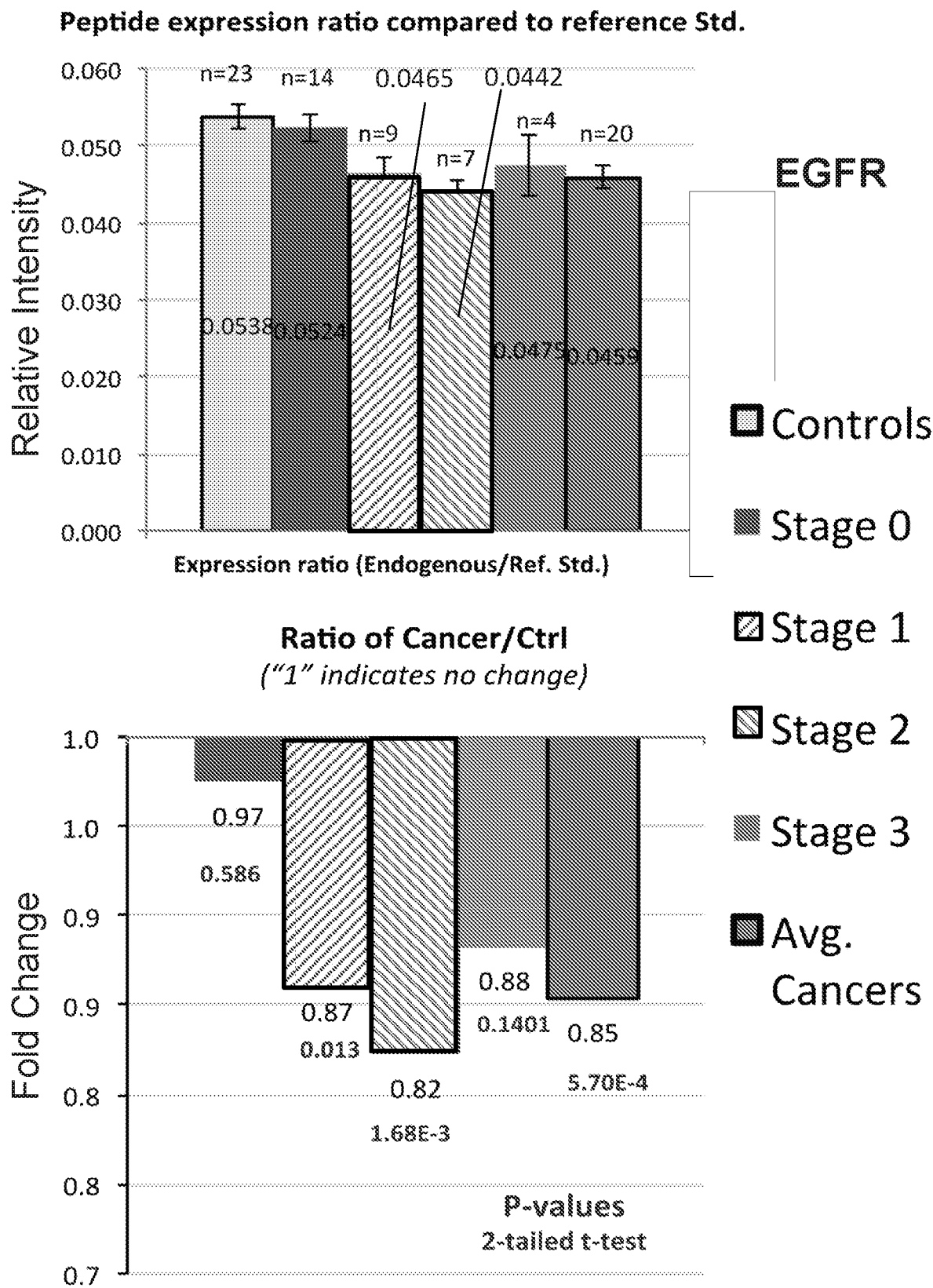
Figure 9C:
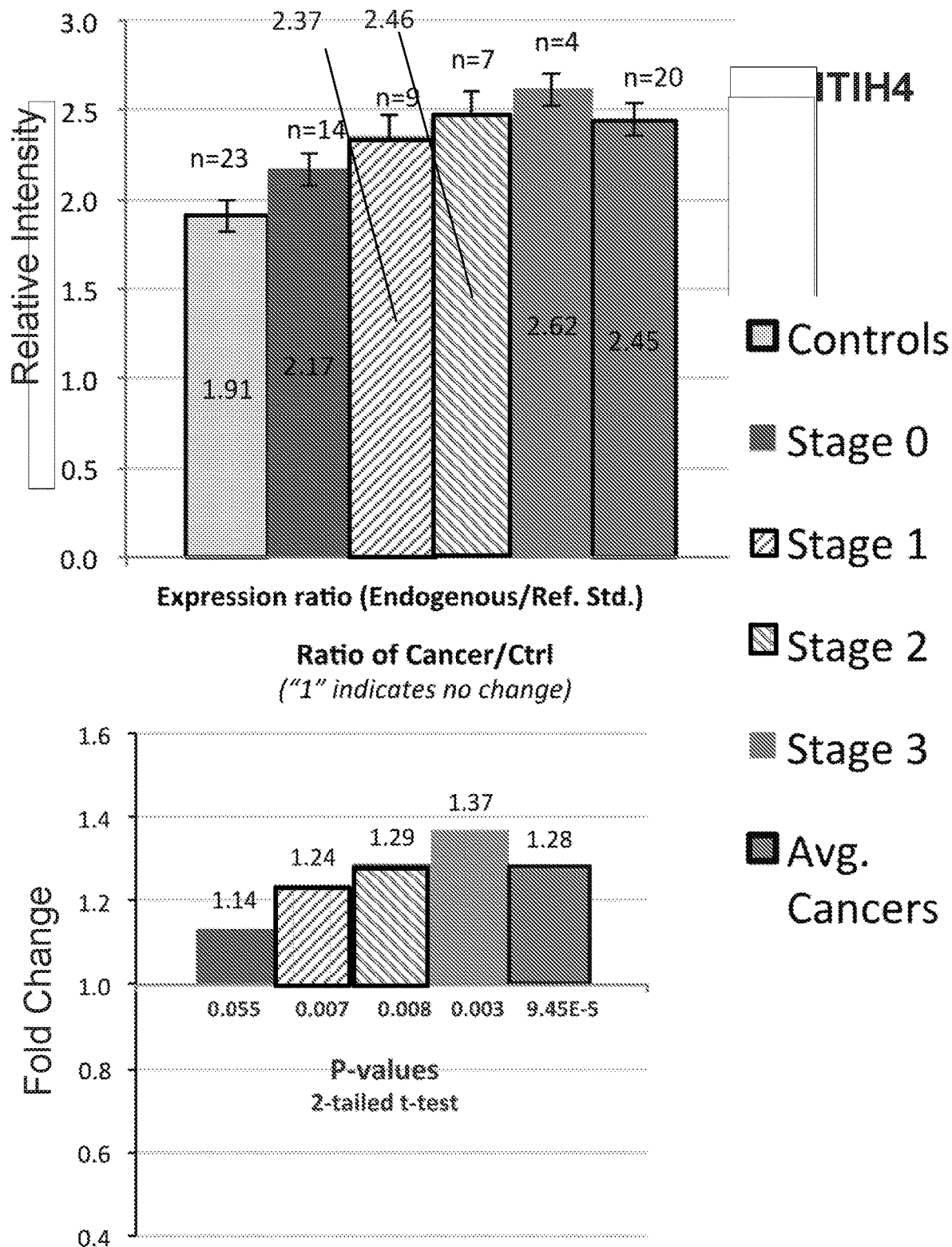
Figure 9F:
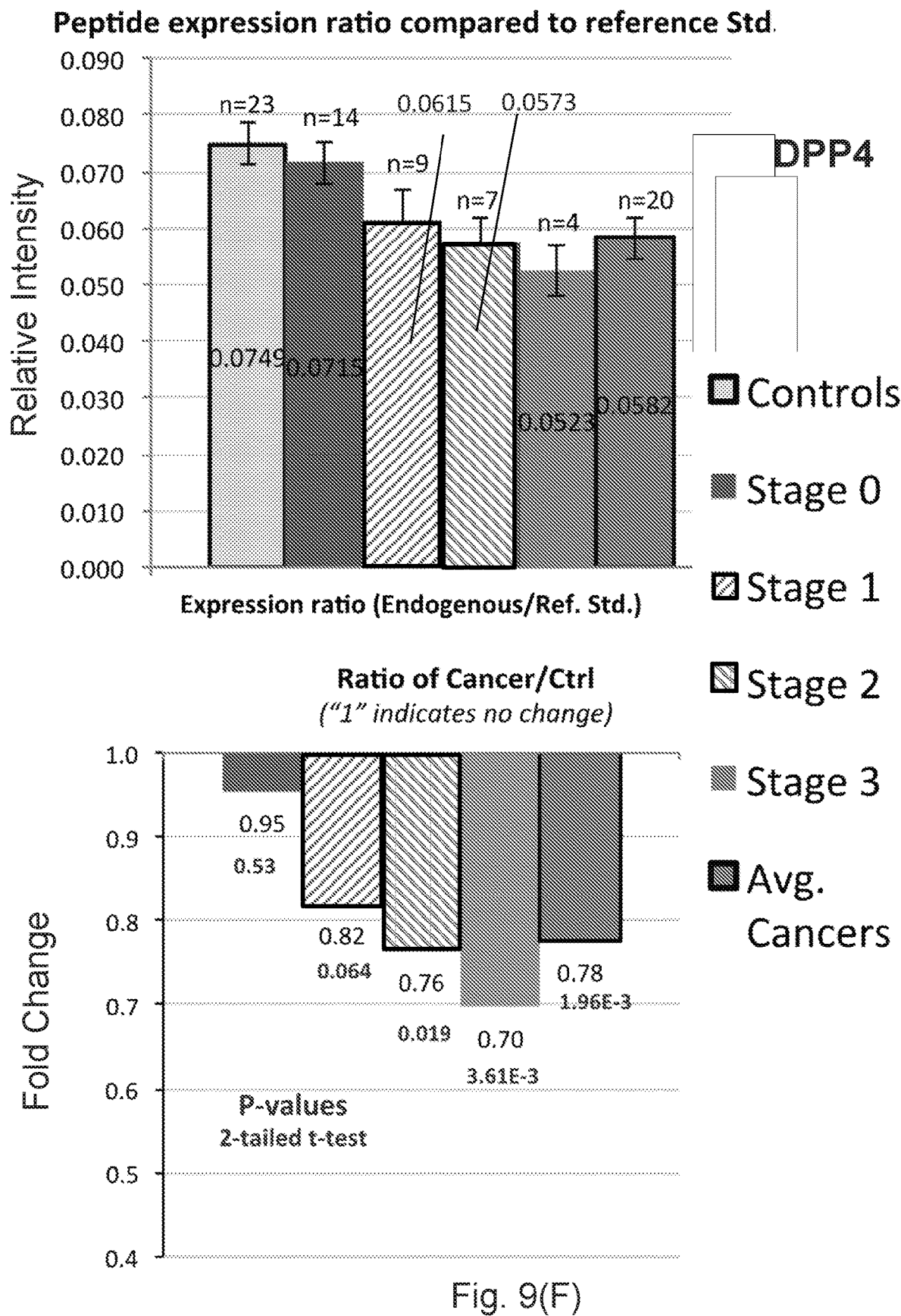
Figure 9G:
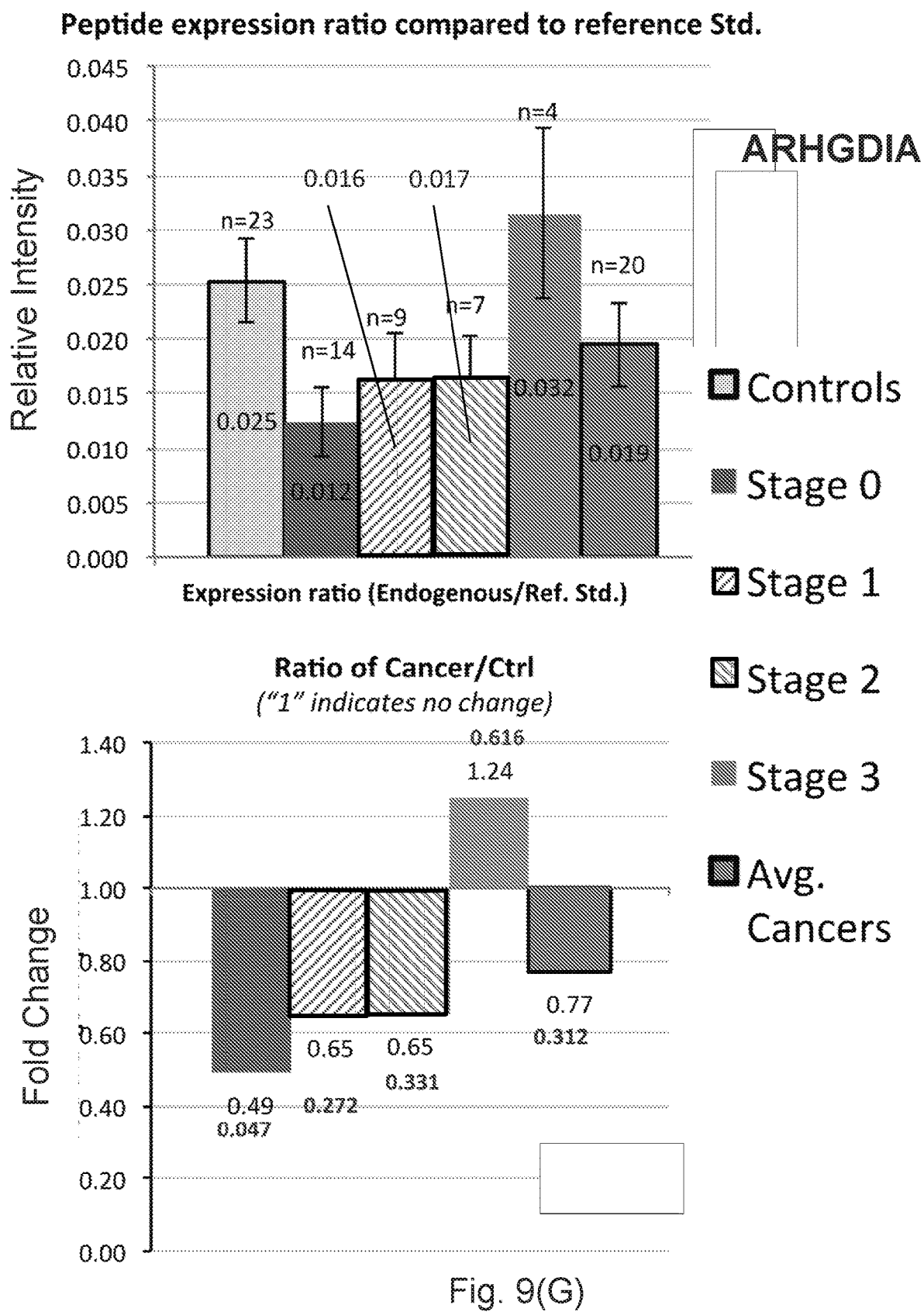
Figure 9I:
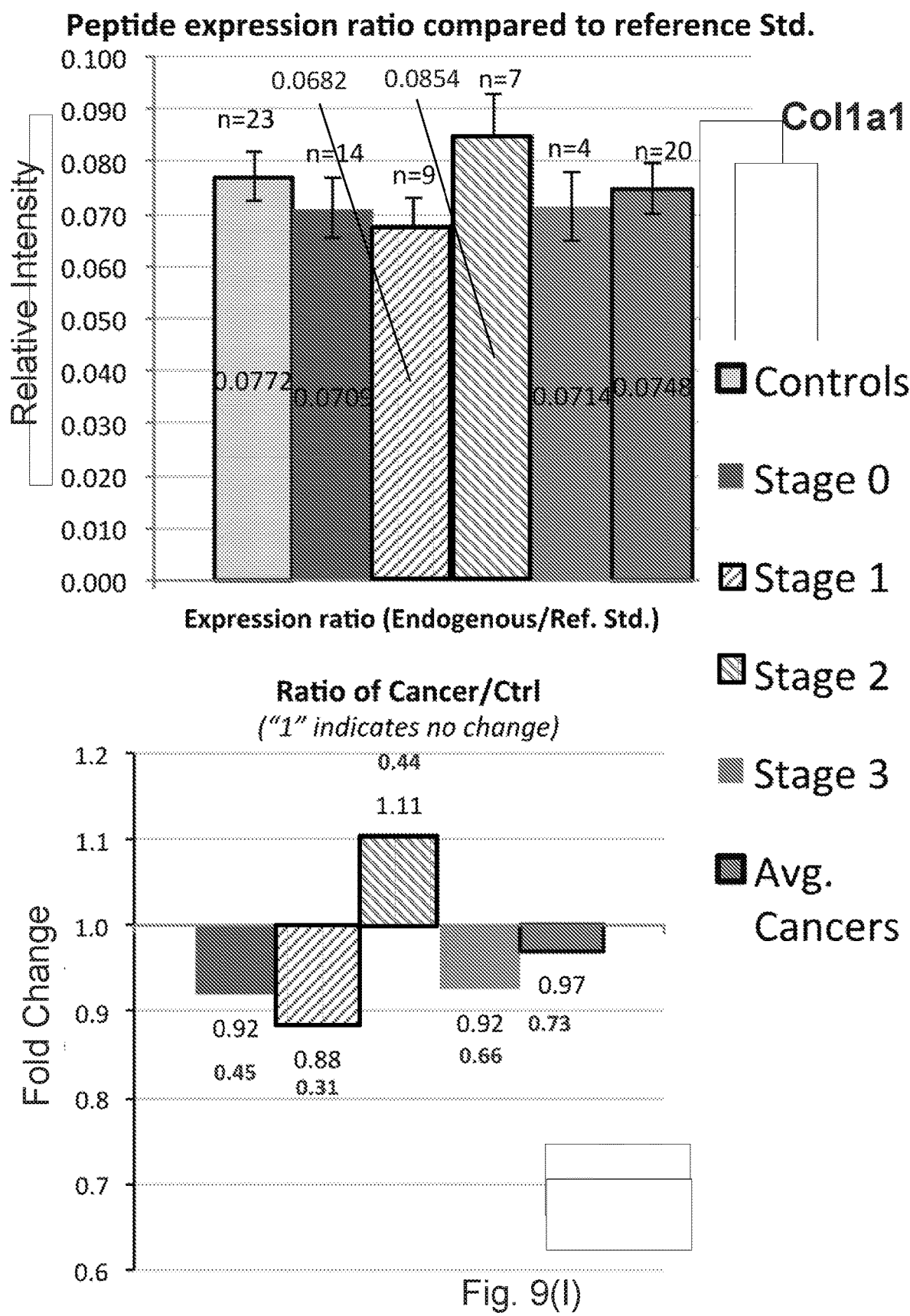

The design of the clinical study is presented in FIG. 8. Serum samples collected from human subjects were divided into four different categories: (1) polyp-free control (n=23), (2) pre- and (3) post-polypectomy from growing adenoma (n=14), and (4) non-metastatic colon cancer (stages 1-3) (n=20). Subjects with a history of inflammatory bowel disease and metastatic colon cancer were excluded from this study. Those within the polyp-free control group were verified as such by colonoscopy. Tumor staging within the non-metastatic cancer group was achieved from pathology results from tumors removed at the time of surgical resection. The subjects with known growing adenomas were identified by longitudinal analysis of their polyps using computed tomography (CT) colonography. At the first patient visit, polyps were identified and 3-dimensional size was measured. If the polyp volume was identified as growing at a 5-year follow-up visit, the patient was enrolled in the study, blood collected, and the polyp was removed. Subjects returned for a second blood-draw post-polypectomy approximately one month later. All patients undergoing blood draws prior to polypectomy or surgery were fasted following guidelines for a standard colonoscopy or colectomy preparation (Wexner, S. D. et al., *Gastrointest Endosc* 2006, 63, (7), 894-909). In the post-polypectomy group, approximately half of the patients fasted overnight before the procedure. In a study done by Hsieh et. al. evaluating different collection procedures for samples undergoing proteomic profiling, the differences between fasting and non-fasting serum were minimal (Hsieh, S. Y. et al., *Proteomics* 2006, 6, (10), 3189-98). Thus, unless non-fasted patient samples clearly behave differently from fasted samples, all will be included in the study. Patient accruals are presented in Table 12.

TABLE 12

Accruals of control, adenoma, and colon cancer subjects

| Group: | Current # of samples (Updated Dec. 11, 2014) | Sex (M/F) | Median Age, (range) | Number of Polyps (1/2/3) | Cancer Stage (1/2/3) | Average Pre-Operative CEA Level, (range) | # of samples analyzed by mass spectrometry (as of November 2014) |
|---|---|---|---|---|---|---|---|
| Polyp-free Control | 59 | 34/25 | 59.5, (50-80) | N/A | N/A | N/A | 23 |
| Colon cancer (Stages 0-3) | 20 | 10/10 | 72.5, (49-86) | N/A | 9/7/4 | 2.9, (<0.5-6.3) | 20 |
| Adenoma (Pre- and Post-polypectomy) | 29 (paired) | 17/7 | 60, (42-76) | 10/11/2 | N/A | N/A | 14 Pre/12 Post |

Sample Preparation.

Serum samples were thawed at room temperature, allowed to sit for a minimum of 30 min at room temperature, and all samples processed within a 4-hour window. Immunodepletion of the top 6 most abundant proteins (albumin, IgG, IgA, transferrin, haptoglobin and antitrypsin) was achieved using a 4.6×100 mm Agilent Multi-Affinity Removal Column according to manufacturer's instructions. Briefly, a 60 µl aliquot of serum was solubilized in 400 µl of Agilent Buffer A, was filtered and injected onto a Waters 1740 HPLC equipped with a photodiode array detector. Both the 215 nm and 280 nm wavelengths were monitored. The flow-through fraction containing low-abundance proteins and bound high abundant protein fraction were both collected. The low abundance proteins were concentrated and precipitated using a trichloroacetic acid protein precipitation as described in Example 2, supra. A Pierce™ BCA protein concentration assay was performed on resolubilized samples according to the manufacturer's instructions (Thermo Fisher Scientific). A 100 µg aliquot of serum proteins was digested with trypsin in the presence of stable isotope labeled reference standards as described in Example 2, supra, and desalted using SPEC C18 solid-phase extraction tips (Agilent) according to manufacturer instructions (Ivancic, M. M. et al., Cancer Prev Res 2014, 55, 7(11); 1160-9).

Mass Spectrometry Assay.

Chromatographic separation of a 2 µg peptide sample was achieved by reversed phase chromatography using a NanoLC Ultra 2D HPLC (Eksigent) equipped with a Nanoflex cHiPLC set to 37° C. A 90-minute gradient was used for peptide separation, as described in detail in Example 2, supra, followed by elution directly into a 5500 QTrap mass spectrometer (AbSciex). Peptide precursors were selected in quadrupole 1 (Q1), fragmented in q2, and the top 3-4 transitions were selected for monitoring in Q3. All Q1 and Q3 masses were measured at unit resolution. A 7-minute scheduling window was applied with a 2-second cycle time. Method development and peak analysis were done using Skyline software (MacLean, B. et al., Bioinformatics 2010, 26, (7), 966-8).

Data Processing and Analysis.

Mass spectrometry results were imported into Skyline and peaks integrated. All peak areas from reference standards and endogenous transitions were evaluated using the AuDIT algorithm to identify the transition with the lowest coefficient of variance (Abbatiello, S. E. et al., Clin Chem 2010, 56, (2), 291-305). Peptide quantities were assessed using the average peak area of the transition with the lowest variance over three technical replicates. Relative changes in protein expression were determined by taking a ratio of (cancer/control) for each protein. The growing adenoma samples were compared to both the polyp-free control group and their paired post-polypectomy sample. A two-tailed student's t-test assuming a normal distribution was used to assess the significance in protein expression changes. A change was considered significant if the p-value was less than or equal to 0.05.

Serum Biomarkers have Diagnostic and Prognostic Utility in Human Colon Cancer.

The serum levels of several biomarkers correlated with cancer incidence and outcomes in the patient study. (FIG. 9A-J, Table 13). EGFR, DPP4, and PI16 were down-regulated in subjects with adenomas and in stages 1-3 colon cancer, and ARHGDIA (RhoDG1) was down-regulated in patients with adenomas and early stage cancers. LRG1, ITIH3, ITIH4, F5, and CRP were up-regulated in patients with colon cancer. (Table 10, statistically significant differences indicated in bold-face.)

TABLE 13

Relative protein expression in subjects with adenomas and non-metastatic carcinomas compared to polyp-free controls (bolded data denote statistical significance)

| Protein Symbol | Avg. Cancers (stages 1-3) | Adenomas (Stage 0) | Stage 1 | Stage 2 | Stage 3 |
|---|---|---|---|---|---|
| EGFR | 0.85 | 0.97 | 0.87 | 0.82 | 0.88 |
| LRG1 | 1.67 | 1.08 | 1.41 | 1.79 | 2.03 |
| ITIH3 | 1.32 | 0.88 | 1.26 | 1.29 | 1.49 |
| ITIH4 | 1.28 | 1.14 | 1.24 | 1.29 | 1.37 |
| DPP4 | 0.78 | 0.95 | 0.82 | 0.76 | 0.7 |
| PI16 | 0.79 | 0.85 | 0.84 | 0.82 | 0.64 |
| F5 | 1.19 | 1.27 | 1.22 | 1.21 | 1.1 |
| CRP | 2.55 | 1.47 | 1.71 | 2.41 | 4.67 |
| ARHGDIA | 0.77 | 0.49 | 0.65 | 0.65 | 1.24 |
| HPX | 1.05 | 0.92 | 1.13 | 1.02 | 0.95 |
| SOD3 | 0.89 | 0.91 | 0.82 | 1.06 | 0.74 |
| THBS4 | 0.92 | 1.01 | 0.98 | 0.99 | 0.68 |
| COL1A1 | 0.97 | 0.92 | 0.88 | 1.11 | 0.92 |
| CDH2 | 1.13 | 0.93 | 1.21 | 1.15 | 0.94 |
| VTN | 1.05 | 1.05 | 1.08 | 0.98 | 1.08 |

Serum Biomarkers with Pre- and Post-Polypectomy Prognostic Relevance.

Paired pre- and post-polypectomy serum samples from patients with growing adenomas were compared to assess changes in protein expression. Two patients with three growing adenomas were used to assess the ability of these biomarkers to differentiate between pre- and post-polypectomy samples. The post-polypectomy blood draws occurred at 21 days (patient 1) and 30 days (patient 2) after polyp removal.

Figure 10:
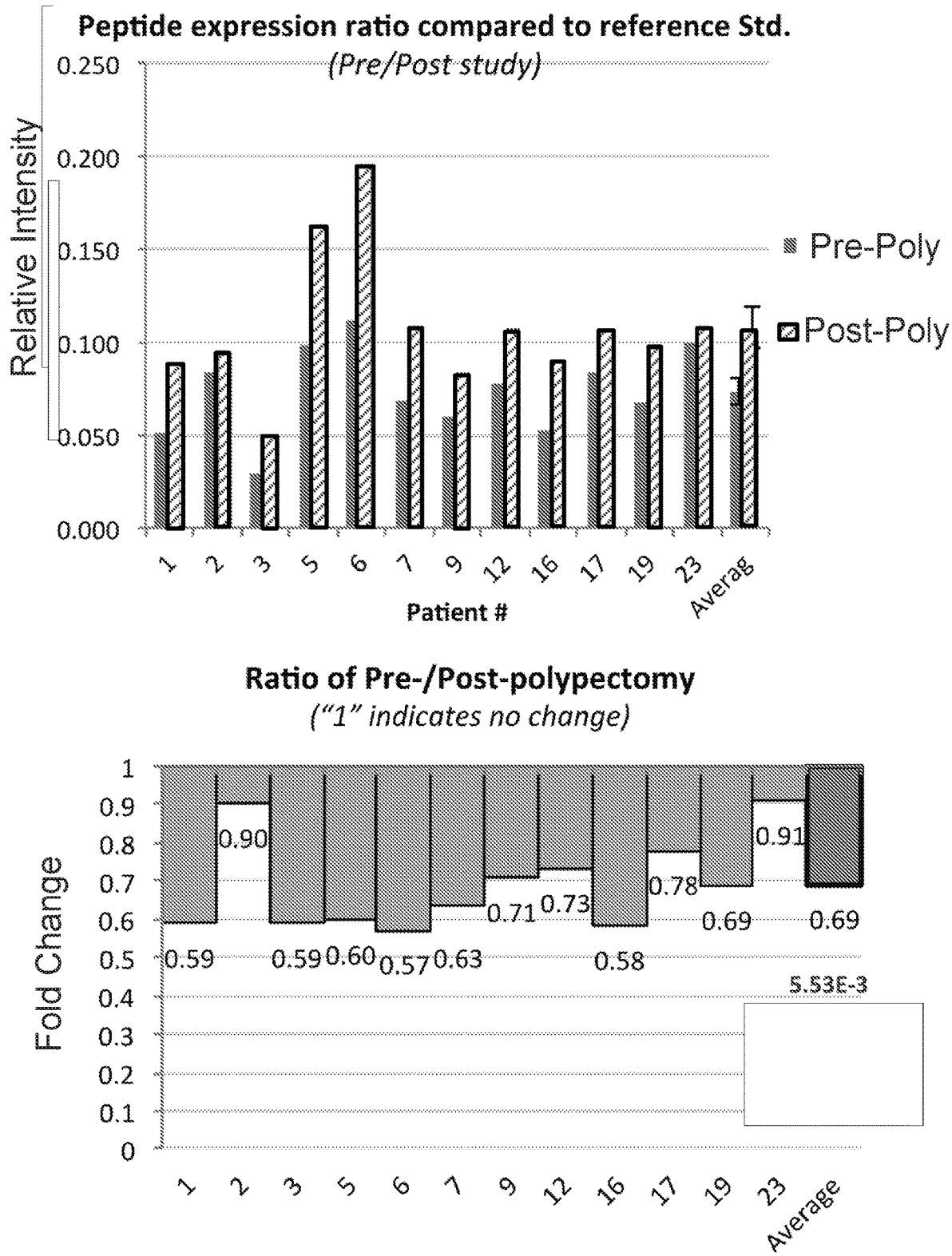
FIG. 10 shows relative Col1a1 biomaker expression levels in 12 patients with known adenomas. Top panel shows expression prior to polyp removal ("pre-poly") and 3-4 weeks after polyp removal. Bottom panel presents the same data as the fold-change in Col1a1 biomarker data after polyp removal.
Figure 11:
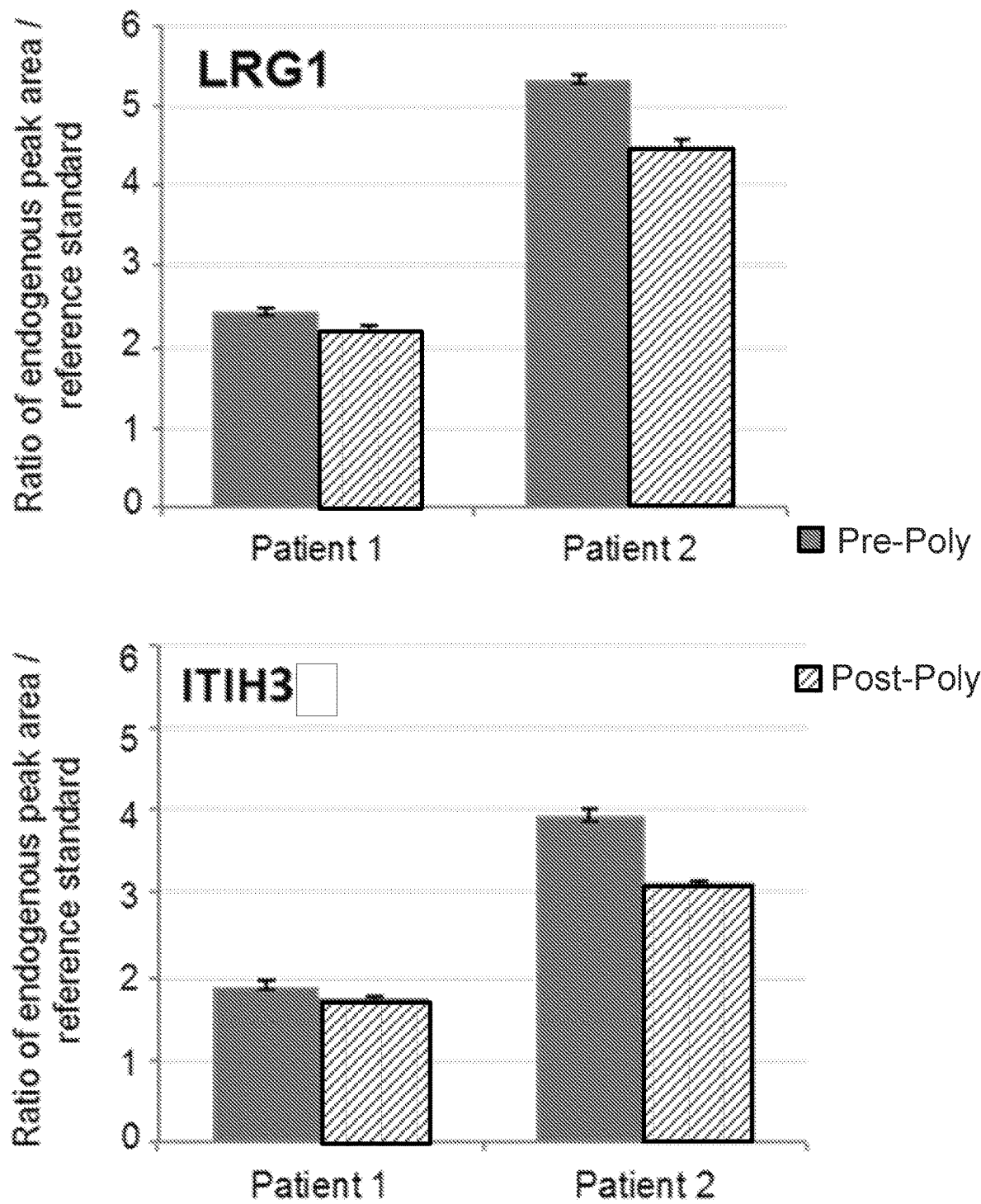
FIG. 11 presents post-polypectomy reversion toward normal expression levels for LRG1 and ITIH3. Patients 1 and 2 in these graphs each had three growing adenomas. The bar graphs display the area ratio between the internal reference standard and the endogenous serum peptide.

LRG1, ITIH3, APCS, SERPIND1, THBS4, and F5 all showed differences in expression between pre- and post-polypectomy samples. Of these six proteins, LRG1 and ITIH3 proteins are upregulated in humans with cancer (Table 13). LRG1 and ITIH3 showed reduced expression levels post-polypectomy in both patient samples (FIG. 11). In addition, Col1a1 shows consistent, statistically significant increase in this protein's expression after polyp removal (FIG. 10).

TABLE 14

Exemplary Peptide Sequences Useful in Disclosed Embodiments

| SEQ ID NO | Peptide Sequence | Protein Biomarker Name |
|---|---|---|
| 1 | TSWGLENEALIVR | Interleukin 1 receptor-like 1 |
| 2 | FTHTENGTNYIVTATR | |
| 3 | SFTVEEK | |
| 4 | AHMSYLFIDK | |
| 5 | FLVDQIVK | Matrix Metalloproteinase-7 |
| 6 | IVSYTTDLPR | (Matrilysin) |
| 80 | DLPHITVDR | |
| 7 | TYFFVGDK | Matrix Metalloproteinase-10 |
| 8 | TVTHTLK | |
| 9 | QDHSTMDLAQQYLEK | |
| 10 | LDSNTVEMMHKPR | |
| 11 | FLGLEMTGK | |
| 12 | IDAAVFEK | |
| 13 | GSQFWAVR | |
| 14 | SNSWLLC | |
| 15 | DDAFFIGSTLATIASTVYSK | CD44 antigen |
| 16 | EPTETPDQFMTADETR | |
| 17 | TQWNPIHSNPEVLLQTTTR | |
| 18 | STPEGYILHTDLPTSQPTGDR | |
| 19 | KPSELNGEASK | |
| 20 | NLQSVDMK | |
| 21 | LVINSGNGTVEDR | |
| 73 | YGFIEGHVVIPR | |
| 22 | AFPAFVLR | Wnt Inhibitory Factor 1 |
| 23 | LGTVPHK | |
| 24 | ASVVQVGFPCLGK | |
| 25 | YGASLMHAPRPAGAGLER | |
| 26 | TPQNAIFFK | |
| 27 | TCQQAECPGGCR | |
| 28 | ADAGQPPEESLYLWIDAHQAR | |
| 29 | LWSILPCLLLLR | |
| 30 | VVGGKPAEMGDYPWQVAIK | Complement Factor I |
| 31 | LPYQCPK | |
| 32 | VFCQPWQK | |
| 33 | GYPTYCHLK | |
| 34 | SFECLHPEIK | |
| 35 | FNIPVNHK | |
| 36 | INSTECLHVR | |
| 37 | FNVSLIYGSTDTEGIVQVK | |
| 81 | VFSLQWGEVK | |
| 38 | ISHELESSSSEVN | Secreted Phosphoprotein-1 |
| 39 | SISTIINVFHQYSR | S100 calcium binding protein A9 |
| 40 | YGHPDTLNK | |
| 41 | LSTSWTEEDVNDNTLFK | Follistatin |
| 42 | ATCLLGR | |
| 43 | EECCSTGR | |
| 44 | WMIFNGGAPNCIPCK | |
| 45 | SIGLAYEGK | |
| 46 | EAACSSGVLLEVK | |
| 47 | CSLCDELCPDSK | |
| 48 | SCEDIQCGGGK | |
| 49 | EACLDPEAPMVQK | Chemokine (C-X-C motif) ligand 1 |
| 50 | LDQNQVR | Chemokine (C-C motif) ligand 2 |
| 51 | MIPMSR | |
| 52 | TLFLLALLGGVSGLR | Leucine-Rich alpha-2-glycoprotein |
| 53 | SSAALNTLVLR | |
| 54 | LLDVAELGTL | |
| 55 | SLPPGLFR | |

TABLE 14-continued

Exemplary Peptide Sequences Useful in Disclosed Embodiments

| SEQ ID NO | Peptide Sequence | Protein Biomarker Name |
|---|---|---|
| 56 | DLVDLCR | |
| 57 | LHLEGNR | |
| 58 | ENQLQEASAR | |
| 76 | VAAGAFQGLR | |
| 59 | NLYLSCVMK | Interleukin-1 beta |
| 60 | CLVLSDPCELK | |
| 61 | DGTPTLQLESVDPK | |
| 62 | SLSQQIENIR | Collagen alpha-1(I) chain |
| 63 | IPLENLQIIR | Epidermal Growth Factor Receptor |
| 92 | NYVVTDHGSCVR | |
| 64 | EVSFDVELPK | Inter-alpha-trypsin inhibitor heavy chain H3 |
| 65 | AYVAFPDFFR | Maltase Glucoamylase |
| 83 | SSVYANAFPSTPVNPLR | |
| 66 | NFFNPPIISR | Coagulation factor V |
| 67 | LWWLDLK | Hemopexin |
| 68 | TIEAEAAHGTVTR | Isocitrate dehydrogenase [NADP], mitochondrial |
| 69 | EAEAAIYHLQLFEELR | Pyruvate Kinase, M2 |
| 70 | VLEPTLK | Vitamin D-binding protein |
| 71 | FEDGVLDPDYPR | Vitronectin |
| 72 | FAHTVVTSR | Inter-alpha-trypsin inhibitor, Heavy chain 4 |
| 74 | TLTLLSVTR | CEACAM5 |
| 75 | LCGTFLGGPKPPQR | Cathepsin B |
| 77 | GYVIIKPLVWV | Serum Amyloid P |
| 78 | IFFESVYGQCK | Fetuin B |
| 79 | ESDTSYVSLK | C-reactive protein |
| 82 | FTVDRPFLFLIYEHR | heparin cofactor 2 |
| 84 | LAGAPSEDPQFPK | Sulfhydryl Oxidase 1 |
| 85 | AEEYEFLTPVEEAPK | Rho-GDP Dissociation Inhibitor 1, Isoform a (ARHGDIA) |
| 86 | WDEELAAFAK | Peptidase inhibitor 16 |
| 87 | GPFPQELVR | Cadherin-2 (N-Cadherin) |
| 88 | WEYYDSVYTER | Dipeptidyl peptidase 4 |
| 89 | VTGVVLFR | extracellular superoxide dismutase [Cu-Zn] |
| 90 | DVDIDSYPDEELPCSAR | Thrombospondin-4 |
| 91 | GFGPPATNQFTTK | receptor-type tyrosine-protein phosphatase mu |

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

We claim:

1. A method for treating a subject with a cancerous colon lesion, the method comprising:
   (a) selecting a subject as having a cancerous colon lesion by
      (i) assaying a biosample from the subject for a plurality of protein biomarkers, wherein the protein biomarkers are epidermal growth factor receptor, leucine-rich alpha-2 glycoprotein, inter-alpha trypsin inhibitor heavy chain 4, hemopexin, and extracellular superoxide dismutase 3 (Cu—Zn);
      (ii) determining the level of the plurality of the protein biomarkers in the biosample;
      and
      (iii) identifying the subject as having a cancerous colon lesion when the levels of leucine-rich alpha-2 glycoprotein, inter-alpha trypsin inhibitor heavy chain 4 and hemopexin are increased and the levels of epidermal growth factor receptor and extracellular superoxide dismutase 3 (Cu—Zn) are decreased compared to levels detected in a subject without a cancerous colon lesion; and
   (b) performing a colonoscopy and thereafter treating the subject by surgical removal of the cancerous colon lesion, chemotherapy, or both, optionally after polypectomy or biopsy.

2. The method of claim 1, wherein the lesion comprises polyp formation.

3. The method of claim 2, wherein the polyp is a carcinoma.

4. The method of claim 1, wherein the biosample is blood, serum, plasma, urine, feces, or saliva.

5. The method of claim 1, wherein the biosample is assayed by a method comprising:
   (a) selecting synthetic peptides with homology to the protein biomarkers and used as reference peptide;
   (b) combining the synthetic peptides with the biosample; and
   (c) subjecting the combination to a physical separation method, wherein the synthetic peptides are labeled.

6. The method of claim 5, wherein the synthetic peptides are selected from one or more peptides according to any of SEQ ID NO. 52-58, 63, 64, 72, 78, 89, or 92.

7. The method of claim 5, wherein the physical separation method is liquid chromatography.

8. The method of claim 5, wherein the synthetic peptides areisotopically labeled.

9. The method of claim 1, wherein determining the level of of the protein biomarkers comprises absolute quantification of the concentration of protein biomarkers in the biosample.

10. The method of claim 1, wherein the assaying step comprises an immunologic assay.

11. The method of claim 10, wherein said immunologic assay comprises an enzyme-linked immunosorbent assay.

12. The method of claim 1, wherein the determining step comprises mass spectrometry.

* * * * *